(12) United States Patent
Li et al.

(10) Patent No.: US 11,306,095 B2
(45) Date of Patent: Apr. 19, 2022

(54) USE OF PTERIDINONE DERIVATIVE SERVING AS EGFR INHIBITOR

(71) Applicant: EAST CHINA UNIVERSITY OF SCIENCE AND TECHNOLOGY, Shanghai (CN)

(72) Inventors: Honglin Li, Shanghai (CN); Yufang Xu, Shanghai (CN); Zhenjiang Zhao, Shanghai (CN); Wei Zhou, Shanghai (CN); Yuqiong Xu, Shanghai (CN); Deheng Sun, Shanghai (CN); Xia Wang, Shanghai (CN); Zhuo Chen, Shanghai (CN)

(73) Assignee: EAST CHINA UNIVERSITY OF SCIENCE AND TECHNOLOGY, Shanghai (CN)

( * ) Notice: Subject to any disclaimer, the term of this patent is extended or adjusted under 35 U.S.C. 154(b) by 0 days.

(21) Appl. No.: 15/577,518

(22) PCT Filed: May 30, 2016

(86) PCT No.: PCT/CN2016/083945
§ 371 (c)(1),
(2) Date: Nov. 28, 2017

(87) PCT Pub. No.: WO2016/192609
PCT Pub. Date: Dec. 8, 2016

(65) Prior Publication Data
US 2018/0148454 A1 May 31, 2018

(30) Foreign Application Priority Data
May 29, 2015 (CN) .......... 201510289399.4

(51) Int. Cl.
C07D 487/04 (2006.01)
A61P 35/00 (2006.01)
A61P 35/02 (2006.01)
A61K 31/519 (2006.01)
C07D 475/00 (2006.01)

(52) U.S. Cl.
CPC .......... *C07D 487/04* (2013.01); *A61K 31/519* (2013.01); *A61P 35/00* (2018.01); *A61P 35/02* (2018.01); *C07D 475/00* (2013.01)

(58) Field of Classification Search
None
See application file for complete search history.

(56) References Cited

U.S. PATENT DOCUMENTS

| 7,169,778 | B2 | 1/2007 | Denny et al. |
| 9,670,213 | B2 * | 6/2017 | Li .......... C07D 475/00 |
| 2015/0126508 | A1 | 5/2015 | Li et al. |

FOREIGN PATENT DOCUMENTS

| CN | 1373763 A | 10/2002 |
| WO | 2006/002367 A1 | 1/2006 |
| WO | 2013/170671 A1 | 11/2013 |

OTHER PUBLICATIONS

Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Harari, P. Epidermal growth factor receptor inhibition strategy in oncology. Endocrine-Related Cancer, 2004, 11, 689-708.*
English Translation of the International Search Report corresponding to PCT/CN2015/083945 dated Aug. 22, 2016, 3 pages.

* cited by examiner

*Primary Examiner* — Po-Chih Chen
(74) *Attorney, Agent, or Firm* — Mintz Levin Cohn Ferris Glovsky and Popeo, P.C.

(57) ABSTRACT

The present invention relates to a pteridinone derivative serving as an EGFR inhibitor and use thereof. Specifically, the present invention relates to a compound represented by the following formula I, pharmaceutical composition comprising the compound of the following formula I, and use of the compound in preparation of drugs for treating EGFR-mediated diseases or inhibiting EGFR.

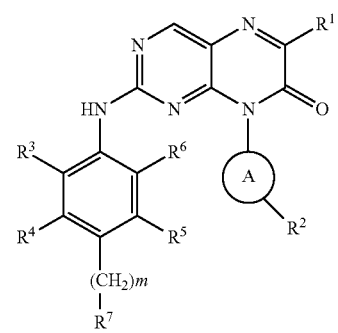

I

11 Claims, 6 Drawing Sheets

Intestine

Lung

Liver

Tumor

Brain

Kidney

USE OF PTERIDINONE DERIVATIVE SERVING AS EGFR INHIBITOR

TECHNICAL FIELD

The present invention relates to the field of medicinal chemistry; and in particular, the present invention relates to novel pteridine derivatives, synthesis methods and uses thereof as inhibitors of epidermal growth factor receptor tyrosine kinase (EGFR) for treating EGFR-mediated diseases (tumors).

BACKGROUND

Cancer, also known as malignant tumor, is a group of diseases characterized by abnormal cell proliferation, metastasis, high incidence and high mortality, and is one of the malignant diseases that threaten human health and cause death. Research data show that in 2008, there were 12.7 million cancer patients, in which the number of death was up to 700 million. And 20% of new cases of tumor in the world occur in China, and 24% of tumor-caused death occurs in China. Without effective prevention or better treatment options, it is estimated that by 2030 there will be 26 million new cases of cancer worldwide each year and the number of cancer-caused deaths will reach 17 million. Among the existing cancers, lung cancer is the malignant tumor with the highest morbidity and mortality in the world, wherein non-small cell lung cancer (NSCLC) accounts for more than 80% of lung cancer patients. According to World Health Organization (WHO), it is predicted that by 2025, annual increase of new cases of lung cancer will be more than 1 million in China. Once diagnosed as having lung cancer, patients have only little prospect for survival, and 5-year survival rate of less than 15%.

Since the 1980s, molecular mechanisms of tumorigenesis and development have been clear with deep researches on tumor molecular biology. Among many cancer-inducing factors, some of highly expressed protein kinases in cancer cells caused by gene mutations are one of major factors leading to abnormal signal transduction pathways. Protein, tyrosine kinase is an important factor in signal transmission process, involved in a series of cell activities, and closely related to cell growth, differentiation, and proliferation. It catalyzes the transfer of γ-phosphate group of ATP to tyrosine residues of many important proteins and phosphorylates phenolic hydroxyl, thereby transferring signals. Therefore, for developing anti-tumor drugs, it is an effective research strategy to develop selective protein kinase inhibitors to block or regulate diseases caused by these abnormal signaling pathways. Among many tyrosine kinases, epidermal growth factor receptor tyrosine kinase (EGFR) is an indispensable and important part. EGFR consists of 1186 amino acids and encodes a transmembrane glycoprotein with a molecular weight of 170-kDa. EGFR can mediate multiple signal transduction pathways and transmit extracellular signals into cells, which plays an important regulatory role in the proliferation, differentiation and apoptosis of normal and tumor cells (Cell, 2000, 100, 113-127). EGFR is a constitutively expressed component in many normal epithelial tissues, such as the skin and hair follicles, while overexpressed or highly expressed in most solid tumors. For example, in lung cancer, the expression rate of EGFR reaches 40 to 80%. Therefore, the purpose of treating lung cancer can be achieved by selectively inhibiting EGFR and interfering with its signal transduction pathways, which will open up a feasible way for targeted treatment of lung cancer.

In clinical practice, EGFR-targeting drugs such as Iressa, Tarceva, etc in combination with traditional radiotherapy and chemotherapy were proved to be very effective in the treatment of lung cancer. However, clinical practice shows that most patients with non-small cell lung cancer develop acquired resistance within 6-12 months after treatment with Gefitinib or Erlotinib. Approximately 50% of cases of resistance are related to mutation in one amino acid residue in EGFR kinase domain (mutation of threonine residue at position 790 to methionine, T790M) (The New England Journal of Medicine, 2005, 352, 786-792). T790M mutation results in steric hindrance when an inhibitor binds to EGFR or increases the affinity of EGFR to ATP, so that the anticancer effects of such reversibly-binding competitive inhibitors are greatly reduced. Drug resistance not only reduces the patient's sensitivity to drugs, but also greatly reduces the quality of lives of cancer patients. For overcoming the resistance induced by T790M mutation, a series of irreversible ATP competitive inhibitors (such as CI-1033, HKI-272, PF00299804, etc.) have entered the clinical research stage. The irreversible inhibitors contain a Michael acceptor fragment that forms a covalent bond with a conserved amino acid residue (Cys797) at the ATP binding site of EGFR, thereby resulting in stronger EGFR-binding affinity as compared with the reversible inhibitor. However, this type of drugs exhibit poor selectivity to both wild-type and mutant EGFR, therefore maximal tolerated dose (MTD) thereof is low, and clinical effects are less effective. In addition, some compounds exhibit poor druggability despite good activity, which limits their clinical application.

Therefore, it is of great clinical significance and application prospects for studying and developing EGFR-targeted drugs that can selectively inhibit T790M mutation and overcome clinical resistance

SUMMARY OF THE INVENTION

An object of the present invention is to provide a derivative of pteridinone with novel structure, which is capable of selectively inhibiting EGFR T790M mutation and possessing good druggability.

In the first aspect of the present invention, a compound of formula I or a pharmaceutical acceptable salt thereof is provided:

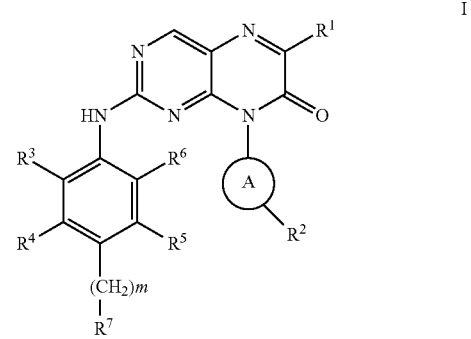

wherein
$R^1$ is independently selected from a group consisting of a hydrogen, substituted or unsubstituted $C_1$-$C_{10}$ alkyl, $C_2$-$C_6$ alkenyl, $C_2$-$C_6$ alkynyl, optionally substituted $C_3$-$C_8$ cycloalkyl, substituted or unsubstituted aryl, substituted or unsubstituted benzyl, substituted or unsubstituted heterocyclyl, substituted or unsubstituted aromatic heterocyclyl;

A is a divalent radical —(CR$_a$R$_b$)$_n$-A'— or absent, wherein R$_a$ and R$_b$ are independently selected from a group consisting of H, a C$_{1-3}$ alkyl, a halogen, and n is an integer from 0 to 3;

A' is a benzene ring, a five- or six-membered heterocycle or a C$_3$-C$_8$ cycloalkyl;

R$^2$ is independently selected from a group consisting of a hydrogen, unsubstituted or halogen-substituted C$_1$-C$_4$ alkyl, nitro, amino, halogen, C$_1$-C$_6$ alkoxy, optionally substituted acyloxy, optionally substituted acylamino, optionally substituted acyl; wherein, when A' is a benzene ring, R$^2$ is meta-substituted;

m is an integer from 0 to 3;

R$^7$ is independently selected from a substituted or unsubstituted NH$_2$, a substituted or unsubstituted heterocyclyl, a substituted or unsubstituted aromatic heterocyclyl, a substituted or unsubstituted C$_1$-C$_{10}$ alkyl;

R$^3$, R$^4$, R$^5$ and R$^6$ are independently selected from a group consisting of H, a halogen, a substituted or unsubstituted C$_1$-C$_6$ (preferably C$_1$-C$_3$)alkoxy, a substituted or unsubstituted C$_1$-C$_6$ (preferably C$_1$-C$_3$)alkyl, NR$_c$R$_d$; wherein each of R$_c$ and R$_d$ is independently selected from C$_1$-C$_3$ alkyl;

wherein, when R$^1$ is H and m is 0, R$^3$, R$^4$, R$^5$ and R$^6$ are not H at the same time;

when R$^1$ is H, m is 0, A' is a benzene ring and R$^7$ is

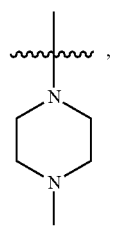, if one of R$^3$ and R$^6$ is a methoxy, the other can not be H.

In a particular embodiment, R$^1$ is independently selected from a hydrogen, substituted or unsubstituted C$_1$-C$_{10}$ alkyl (preferably C$_1$-C$_6$ alkyl), substituted or unsubstituted phenyl, substituted or unsubstituted benzyl, optionally substituted C$_3$-C$_8$ cycloalkyl;

A' is a benzene ring, a five- or six-membered nitrogen-containing heterocycle;

R$^2$ is independently selected from a C$_1$-C$_3$ alkyl, C$_2$-C$_4$ alkenyl substituted acylamino, substituted or unsubstituted C$_2$-C$_4$ alkenyl substituted acyl;

R$^7$ is selected from a group consisting of:

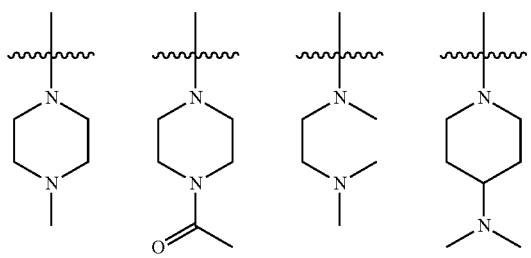

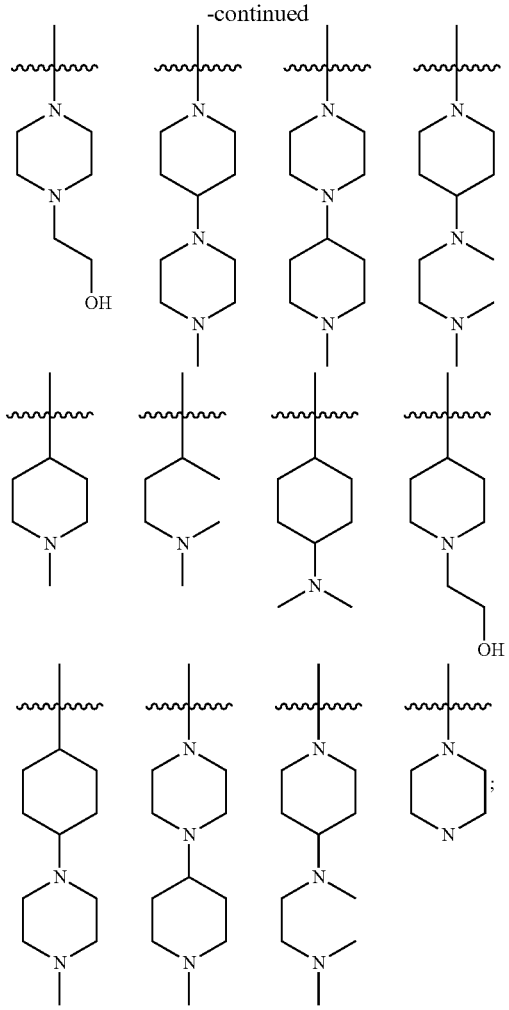

R$^3$, R$^4$, R$^5$ and R$^6$ are independently selected from a group consisting of H, a substituted or unsubstituted C$_1$-C$_6$ (preferably C$_1$-C$_3$)alkoxy, a substituted or unsubstituted C$_1$-C$_6$ (preferably C$_1$-C$_3$)alkyl.

In a particular embodiment,

R$^1$ is independently selected from a group consisting of a hydrogen, substituted or unsubstituted C$_1$-C$_6$ alkyl, or substituted or unsubstituted phenyl;

n=0;

A' is a benzene ring, or a five-membered nitrogen-containing heterocycle;

R$^2$ is independently selected from a C$_2$-C$_4$ alkenyl substituted acylamino, or C$_2$-C$_4$ alkenyl substituted acyl;

m is an integer from 0 to 2;

R$^7$ is selected from:

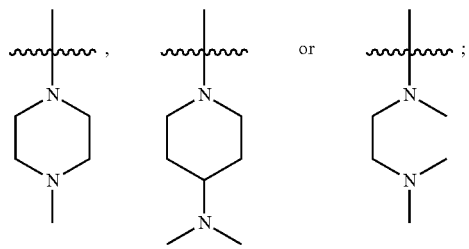

R[3], R[4], R[5] and R[6] are independently selected from a group consisting of H, a substituted or unsubstituted $C_1$-$C_3$ alkoxy, a substituted or unsubstituted $C_1$-$C_3$ alkyl.
In the second aspect of the present invention, a compound of formula I or a pharmaceutical acceptable salt thereof selected from the following group is provided:
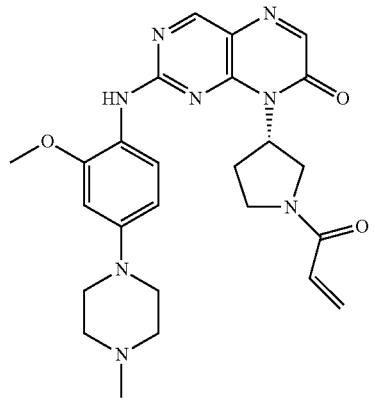
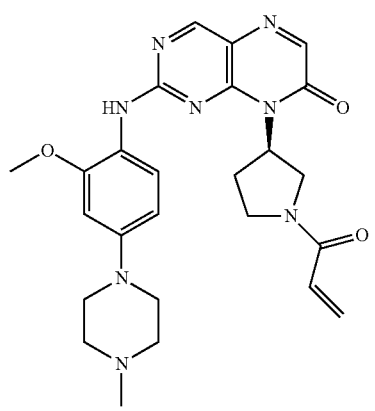
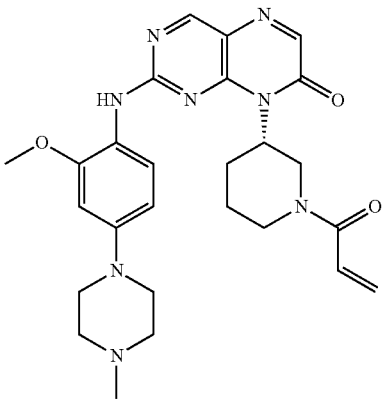
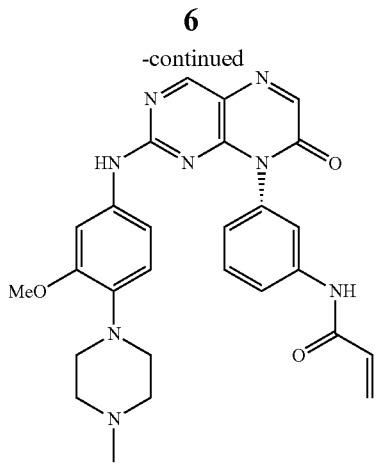
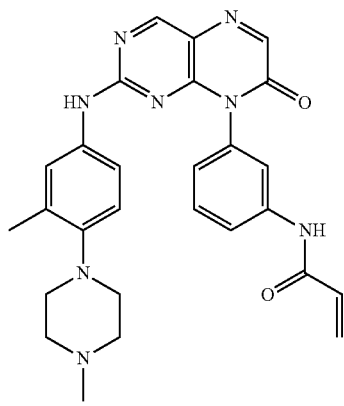
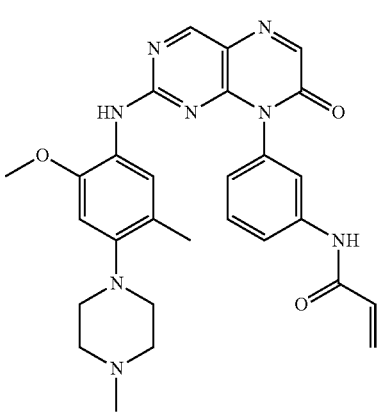
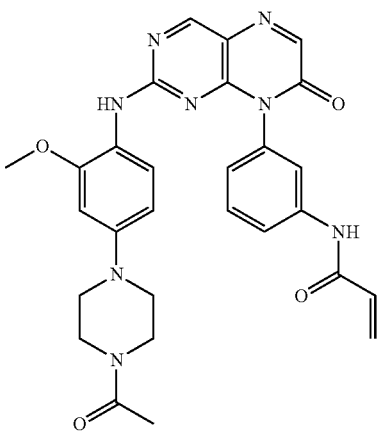

7
-continued
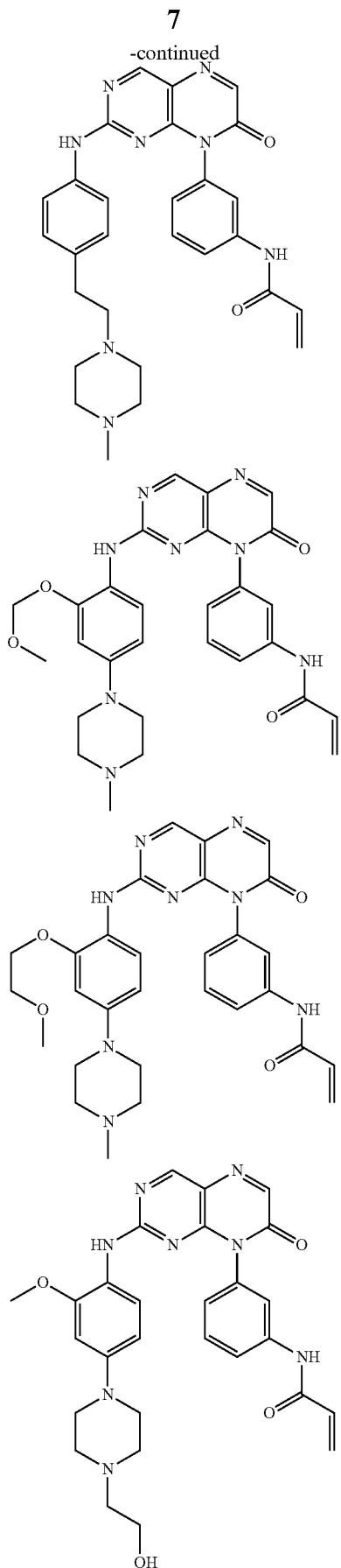
8
-continued
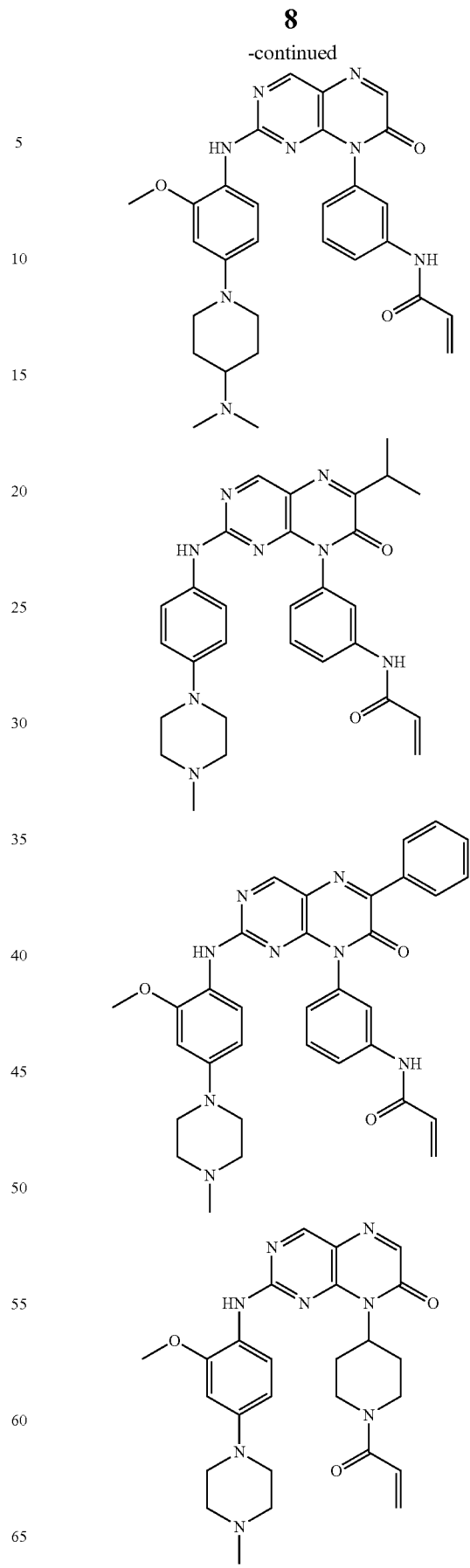

-continued
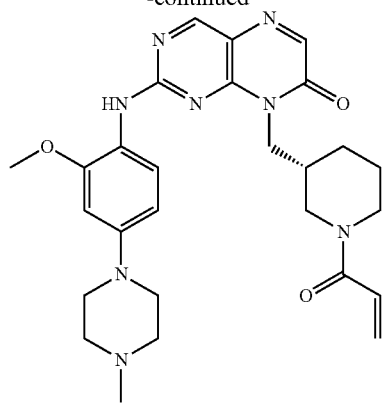
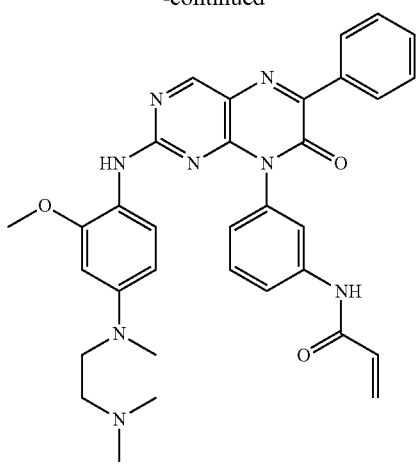
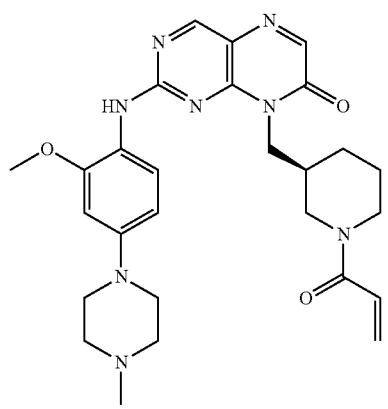
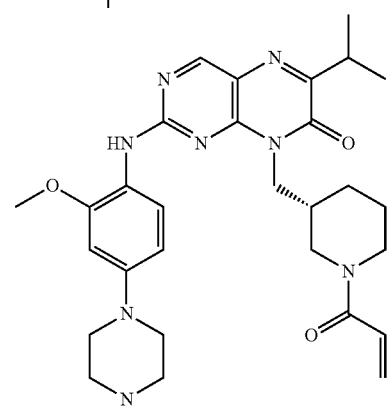
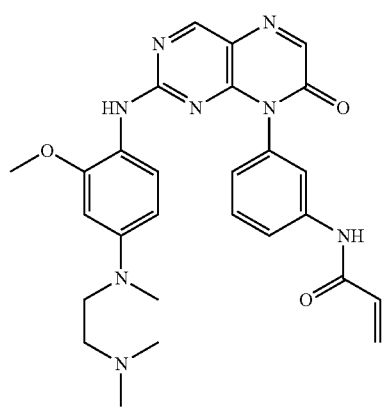
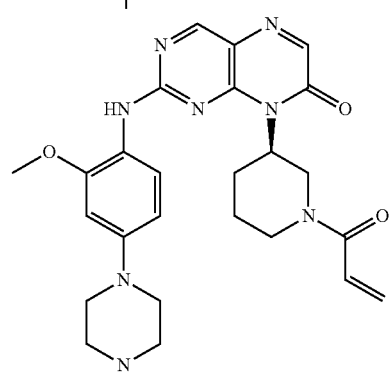
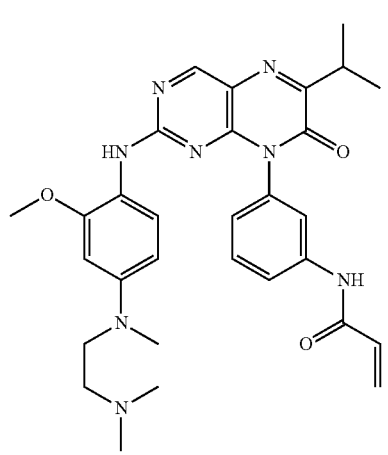
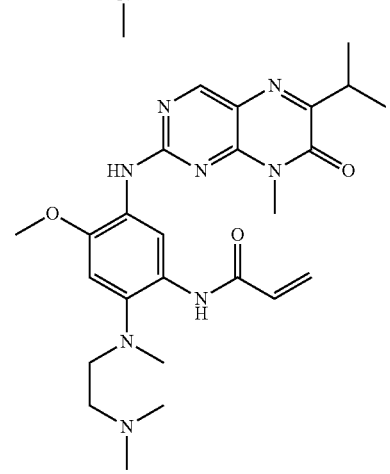

11
-continued
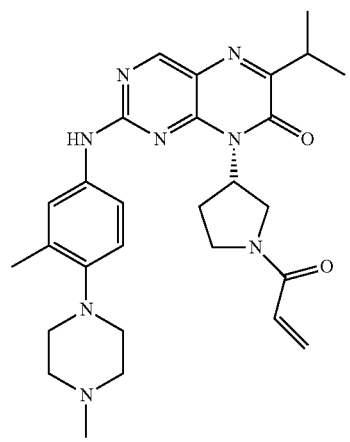
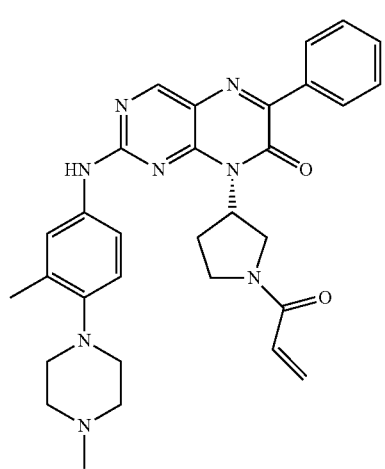
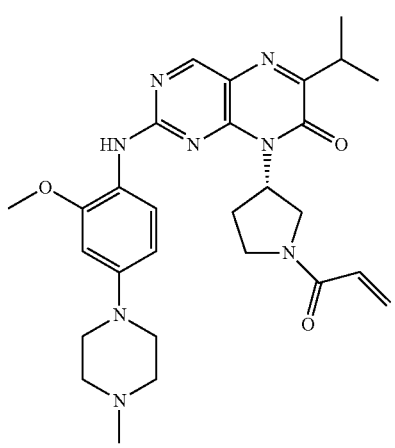
12
-continued
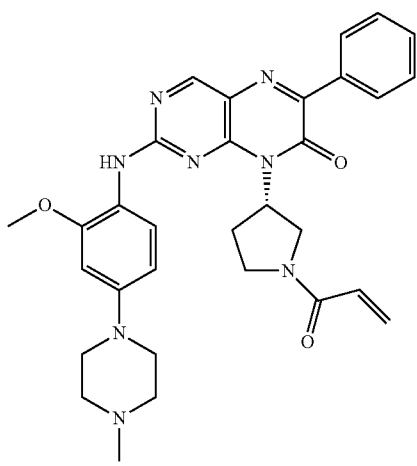
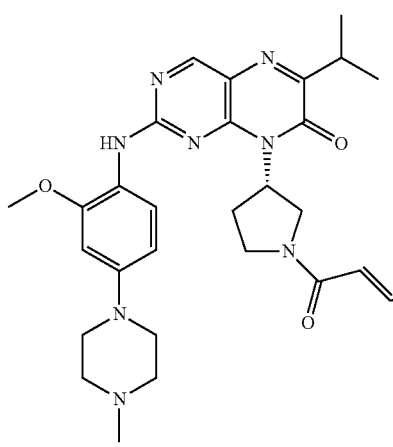
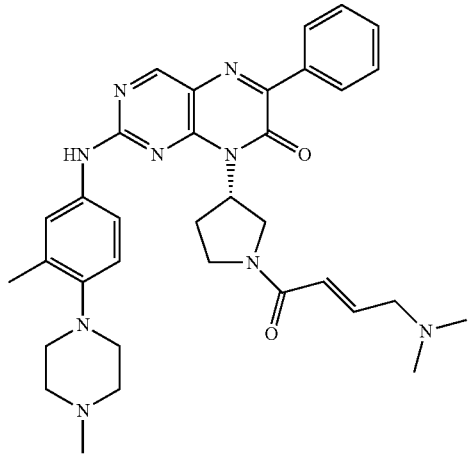

13
-continued
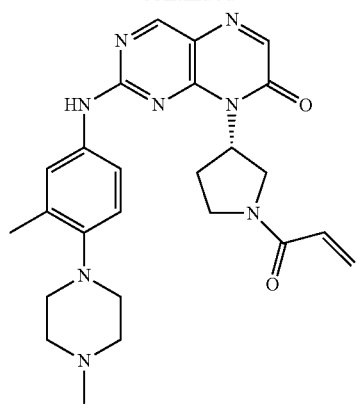
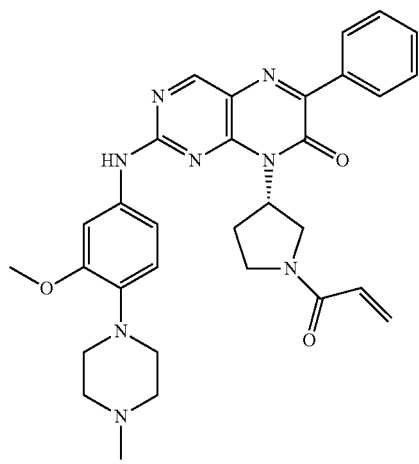
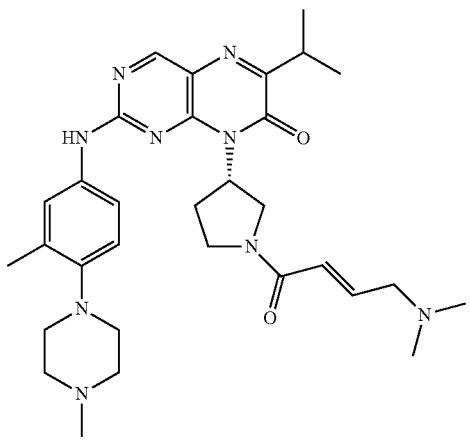
14
-continued
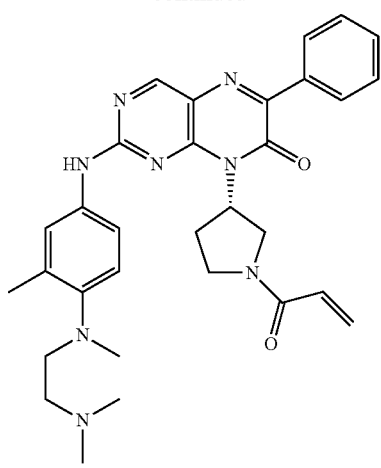
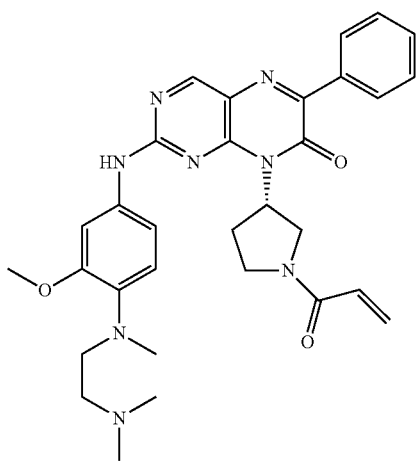
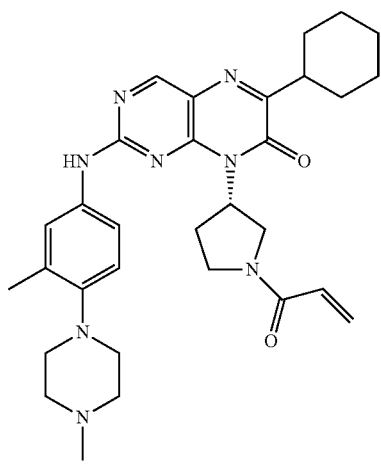

15
-continued
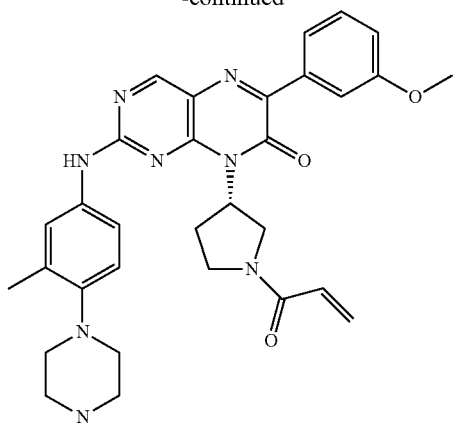
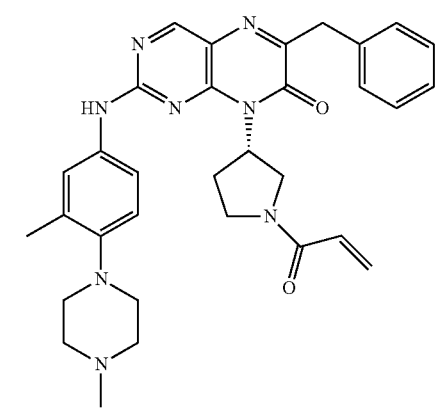
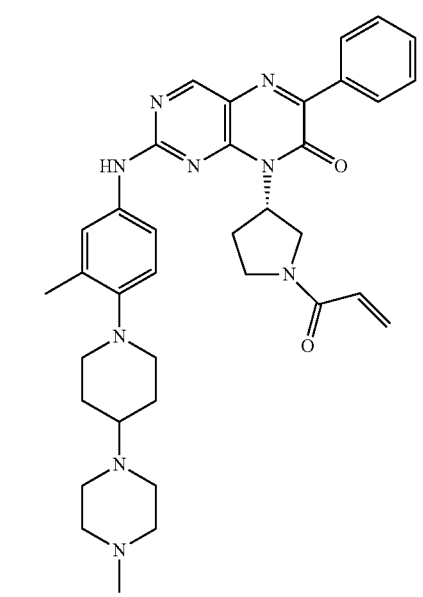
16
-continued
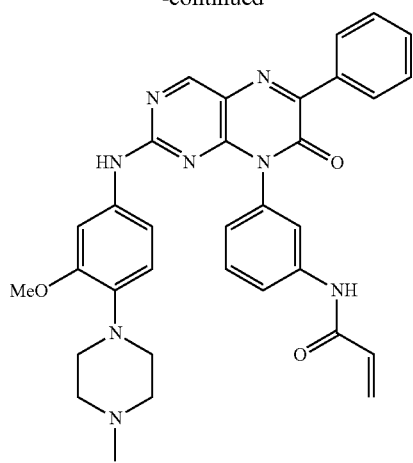
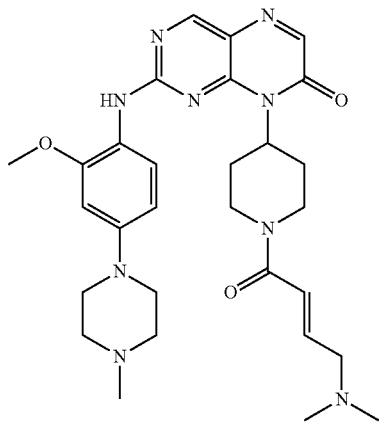
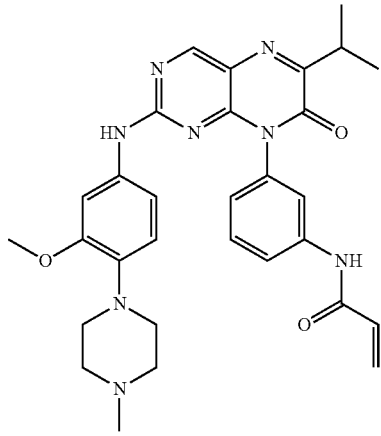
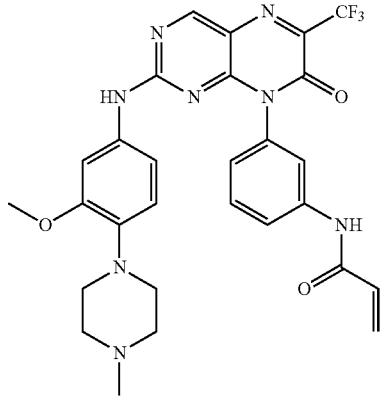

-continued
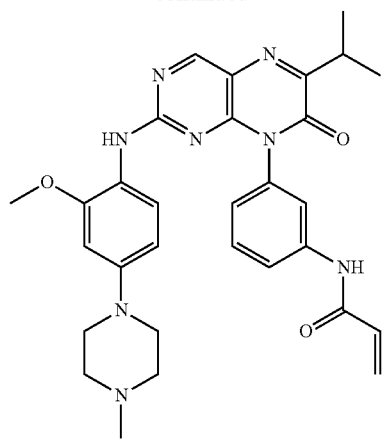
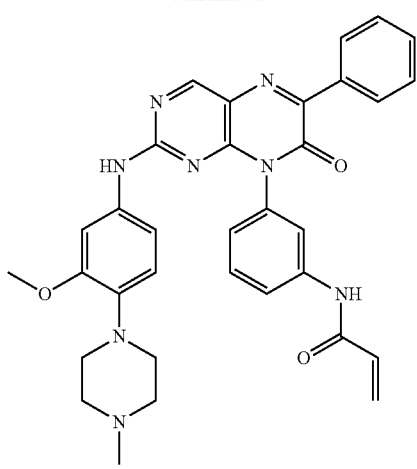
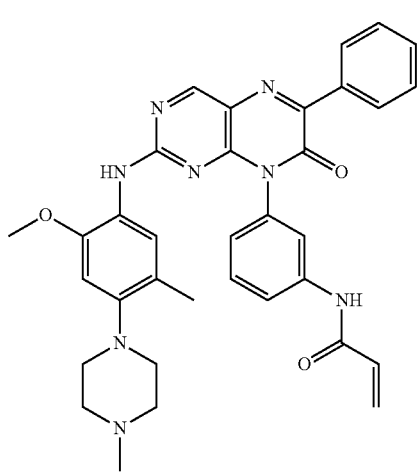
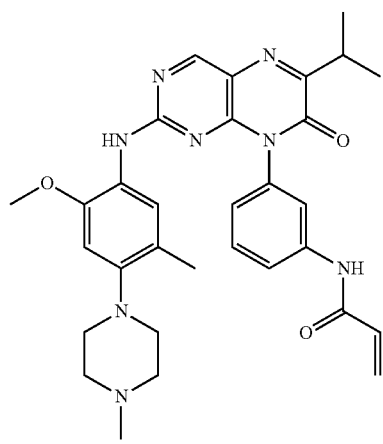
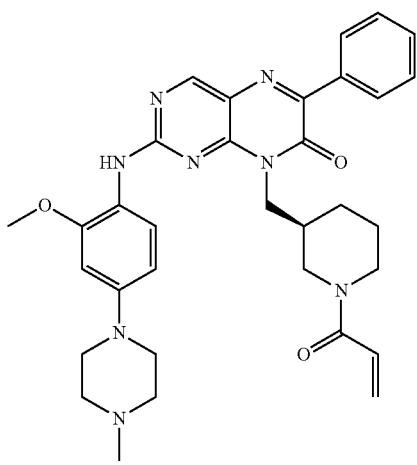

19
-continued
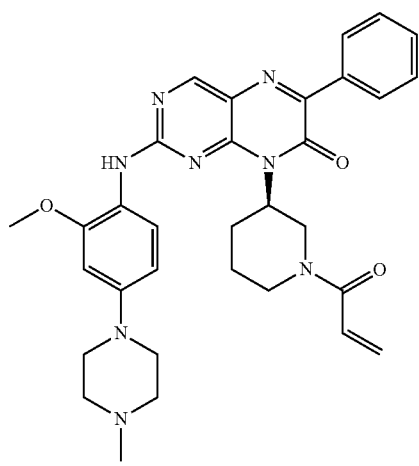
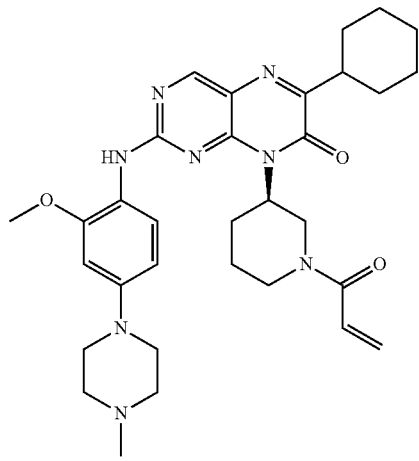
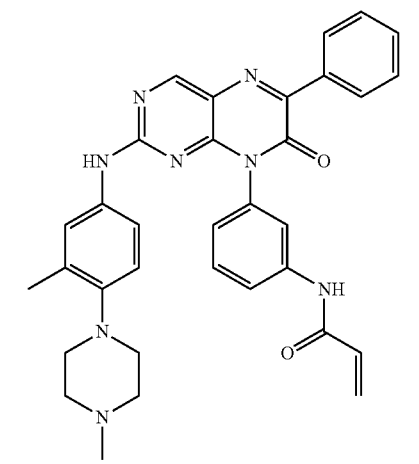
20
-continued
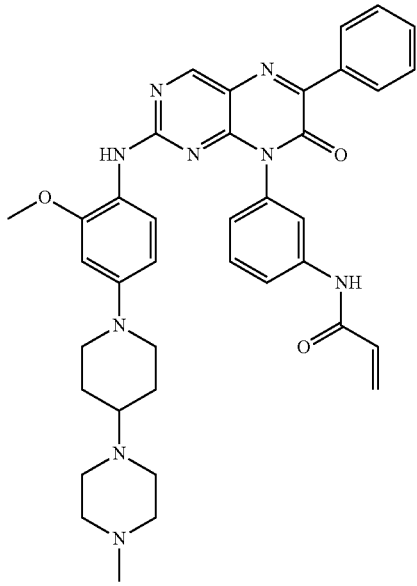
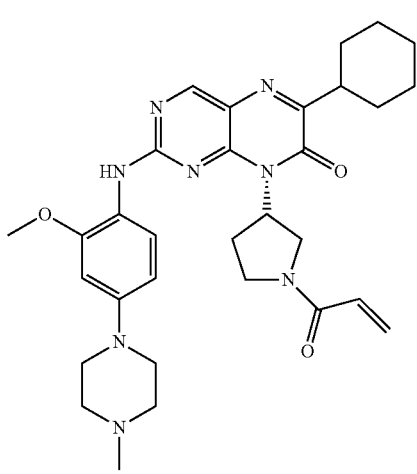

21
-continued
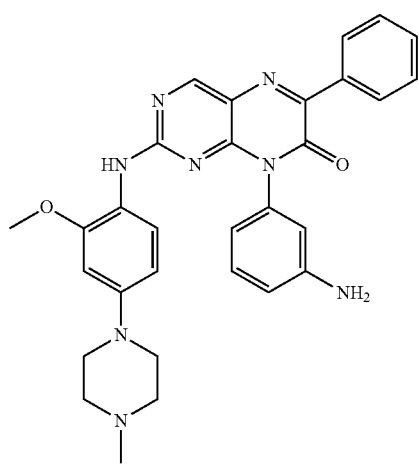
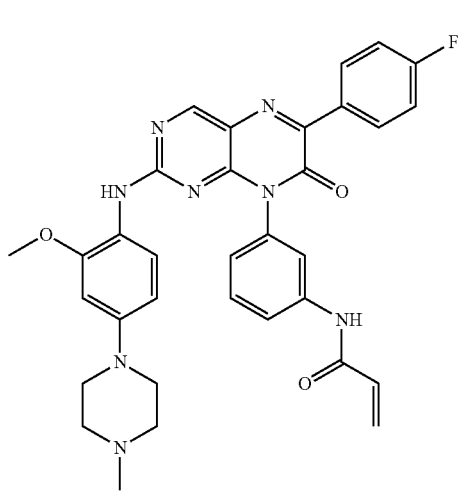
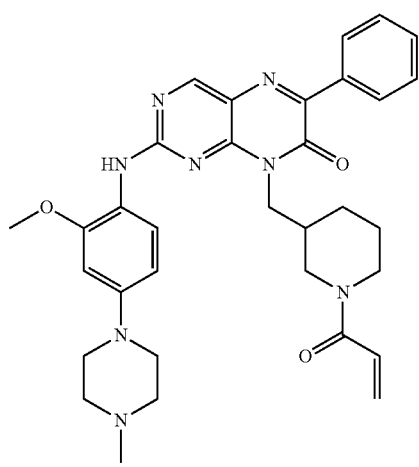
22
-continued
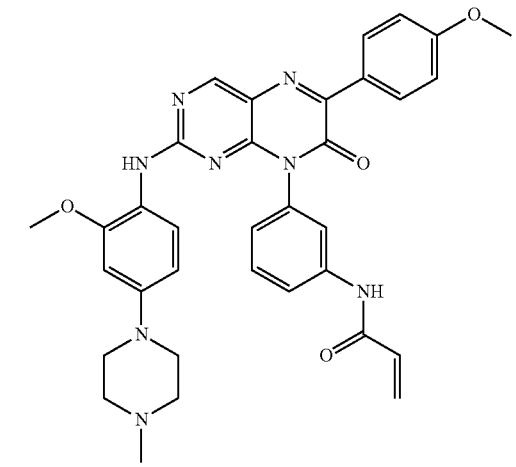
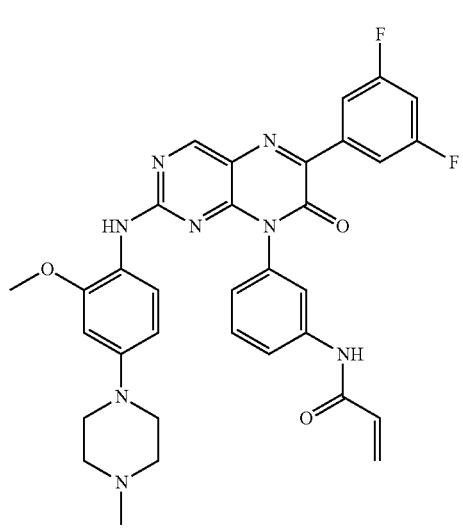
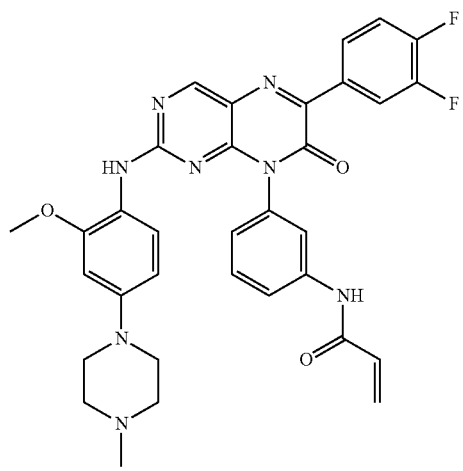

-continued
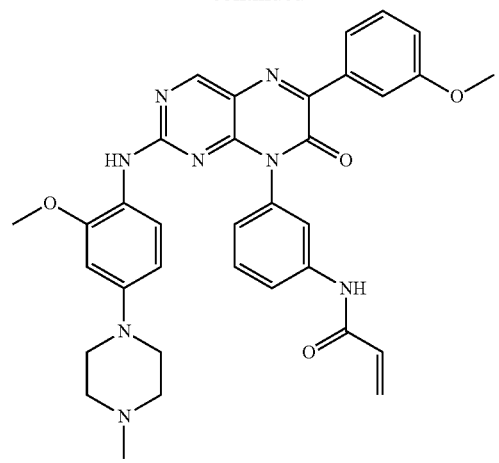
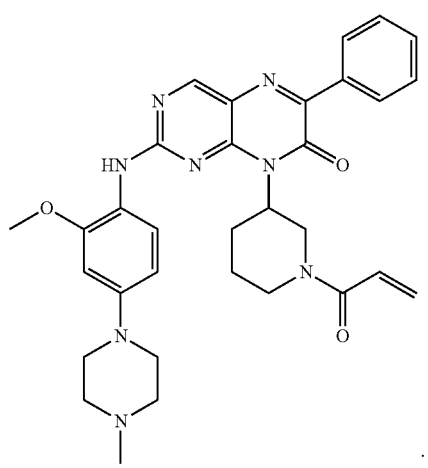
In the third aspect of the present invention, a compound of formula I or a pharmaceutical acceptable salt thereof selected from the following group is provided:
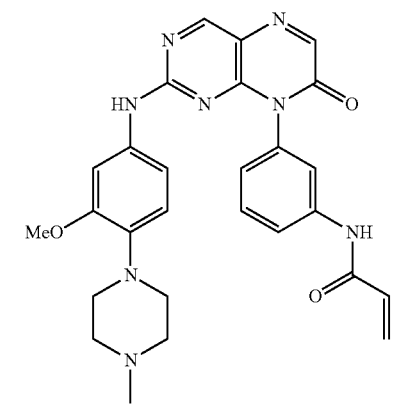
-continued
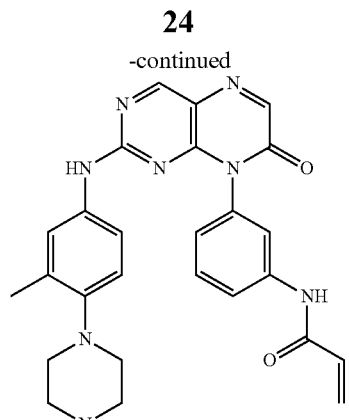
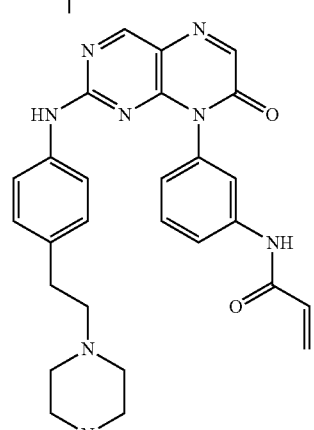
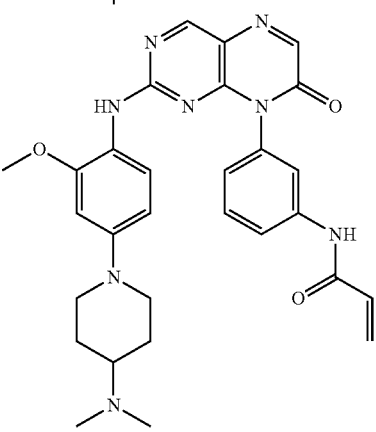
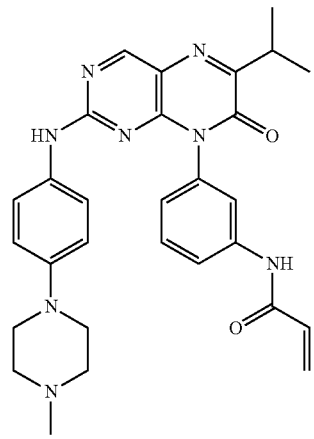

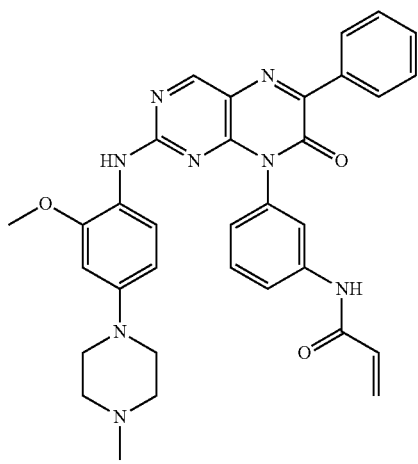

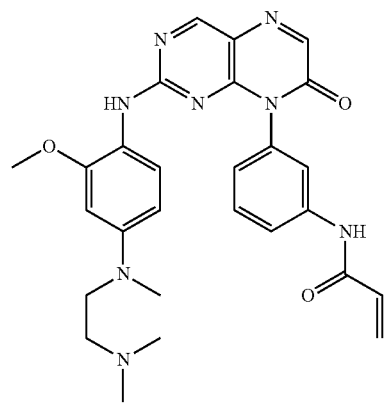

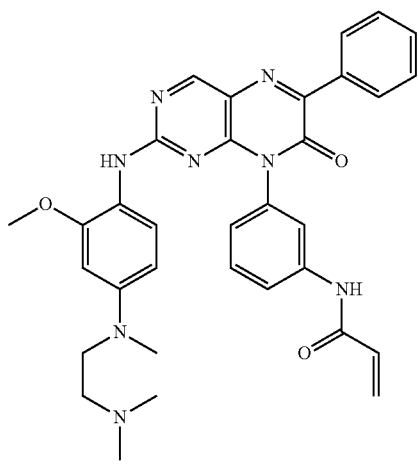

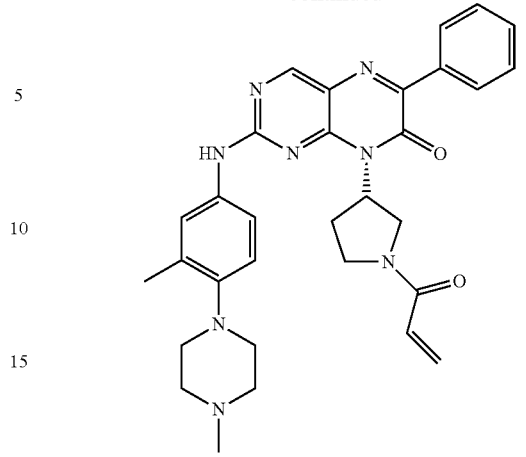

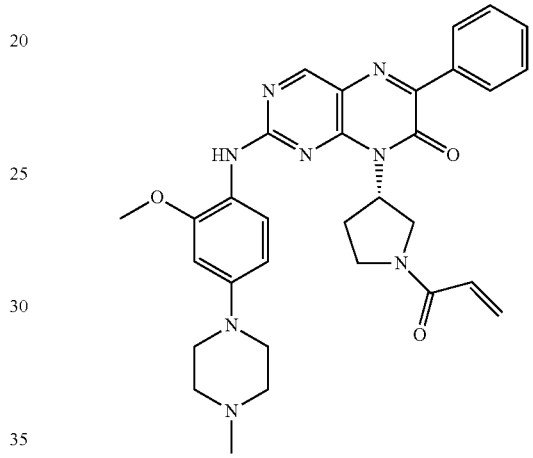

In the fourth aspect, a pharmaceutical composition is provided in the present invention, comprising a compound or a pharmaceutical acceptable salt thereof of the first to the third aspect and a pharmaceutically acceptable carrier or excipient.

In a preferred embodiment, the pharmaceutical composition is in a form suitable for oral administration, including but not limited to tablets, solutions, suspensions, capsules, granules, powders.

In the fifth aspect, use of the compound of the first aspect to third aspect for preparation of a medicament for treating or preventing EGFR-mediated diseases, or inhibiting EGFR is provided in the present invention.

In a particular embodiment, the EGFR-mediated disease is cancer.

In a particular embodiment, the cancer is selected from a group consisting of non-small cell lung cancer, small cell lung cancer, lung adenocarcinoma, lung squamous cell carcinoma, breast cancer, prostate cancer, glioblastoma, ovarian cancer, squamous cell carcinoma of head and neck, cervical cancer, esophageal cancer, liver cancer, kidney cancer, pancreas cancer, colon cancer, skin cancer, leukemia, lymphoma, stomach cancer, multiple myeloma and solid tumors.

In the sixth aspect, a method for treating or preventing EGFR-mediated diseases by using the compound of the first aspect to third aspect is provided in the present invention.

In a preferred embodiment, the EGFR-mediated disease is cancer; preferably, the cancer is selected from a group consisting of non-small cell lung cancer, small cell lung cancer, lung adenocarcinoma, lung squamous cell carcinoma, breast cancer, prostate cancer, glioblastoma, ovarian cancer, squamous cell carcinoma of head and neck, cervical cancer, esophageal cancer, liver cancer, kidney cancer, pancreas cancer, colon cancer, skin cancer, leukemia, lymphoma, stomach cancer, multiple myeloma and solid tumors.

It should be understood that in the present invention, the technical features specifically mentioned above and below (such as in the Examples) can be combined with each other, thereby constituting a new or preferred technical solution which needs not be individually described.

DESCRIPTION OF DRAWINGS

FIG. 5 shows the pathological analysis of tumor-bearing mice after 14 consecutive days of administration, as follows:

MODES FOR CARRYING OUT THE INVENTION

Figure 1:
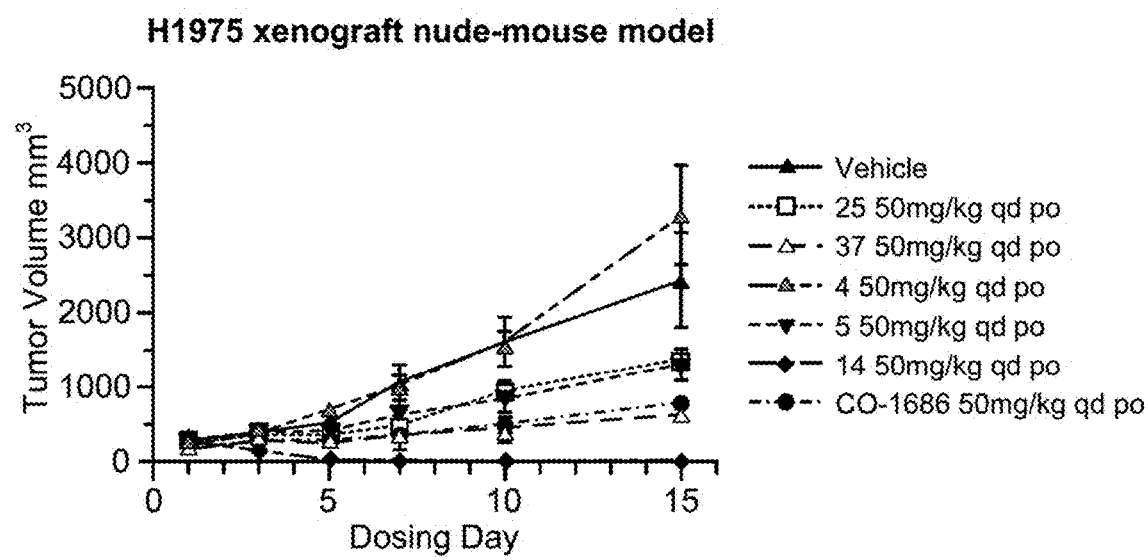
FIG. 1 shows pharmacodynamic evaluation of a series of compounds: after orally administered to nude mice of H1975 cell xenograft model for 14 days, Compound 14 exhibited superior efficacy over CO-1686.

Through comprehensive and intensive research, the inventors have unexpectedly found derivatives of pteridinone with novel structure, which are capable of selectively inhibiting EGFR T790M mutation and possessing good druggability. For these compounds, $IC_{50}$ values of inhibitory activity on EGFR-T790M/L858R kinase and $IC_{50}$ values of inhibiting proliferation of H1975 cells (non-small cell lung cancer cells, EGFR-T790M/L858R) reached nM levels and these compounds exhibited excellent solubility. Based on the above findings, the present invention is completed.

Definition on Terms

The terms mentioned herein are further defined as follows:

As used herein, "alkyl" refers to a saturated straight chain or branched chain alkyl having 1 to 10 carbon atoms, and preferably alkyl includes an alkyl with 2-8 carbon atoms, 1-6 carbon atoms, 1-4 carbon atoms, 1-3 carbon atoms in length. Examples of alkyl include, but not limited to, methyl, ethyl, n-propyl, iso-propyl, n-butyl, iso-butyl, heptyl, and the like. Alkyl can be substituted by one or more substituents, for example substituted by a halogen or a haloalkyl. For example, alkyl may be an alkyl substituted by 1-4 fluorine atoms, or an alkyl substituted by fluorinated alkyl.

As used herein, "cycloalkyl" refers to a saturated cyclic alkyl having 3-10, preferably 3-8 ring carbon atoms. Exemplary cycloalkyl includes, but not limited to, cyclopropyl, cyclobutyl, cyclohexyl, cycloheptyl, and the like. Cycloalkyl can be substituted by one or more substituents, for example substituted by a halogen or a haloalkyl. For example, cycloalkyl may be substituted by 1-4 fluorine atoms. In a preferred embodiment, the cycloalkyl is cyclohexyl.

As used herein, "alkoxyl" refers to an oxy substituted by alkyl. A preferred alkoxyl is an alkoxyl with 1-6 carbon atoms in length, more preferably an alkoxyl with 1-4 carbon atoms in length. Examples of alkoxyl include, but not limited to, methoxyl, ethoxyl, propoxyl and the like. In a particular embodiment, alkoxy can be a substituted alkoxy group, for example, an alkoxy-substituted alkoxy. In a particular embodiment, a $C_1$-$C_3$ alkoxy-substituted $C_1$-$C_3$ alkoxy is preferable.

As used herein, "alkenyl" generally means a monovalent hydrocarbon group with at least one double bond, generally comprises 2-8 carbon atoms, preferably 2-6 carbon atoms and may be of straight or branched chain. Examples of alkenyl include, but not limited to, ethenyl, propenyl, isopropenyl, butenyl, iso-butenyl, hexenyl, and the like.

As used herein, "halogen" refers to fluorine, chlorine, bromine and iodine.

As used herein, "aryl" means a monocyclic, bicyclic or tricyclic aromatic group with 6 to 14 carbon atoms, and includes phenyl, naphthyl, phenanthryl, anthryl, indenyl, fluorenyl, tetralin, indanyl and the like. Aryl can be optionally substituted with 1-5 (e.g., 1, 2, 3, 4, or 5) substituents selected from: a halogen, a $C_{1-4}$ aldehyde group, a $C_{1-6}$ alkyl, a cyano, a nitro, an amino, a hydroxyl, a hydroxymethyl, a halogen-substituted alkyl (e.g., trifluoromethyl), halogen-substituted alkoxyl (e.g., trifluoromethoxyl), a carboxyl, a $C_{1-4}$ alkoxyl, a ethoxyformyl, $N(CH_3)$ and a $C_{1-4}$ acyl, a heterocyclyl or a heteroaryl, and the like.

As used herein, "heterocycle group" includes, but not limited to, 5- or 6-member heterocyclic groups comprising 1-3 heteroatoms selected from O, S or N, including (but not limited to) a furyl, a thienyl, a pyrrolyl, a pyrrolidinyl, a pyrazolyl, an imidazolyl, a triazolyl, an oxazolyl, a pyranyl, a pyridyl, a pyrimidinyl, a pyrazinyl, a piperidinyl, a morpholinyl and the like.

As used herein, "aromatic heterocycle group" means that the group comprises 5 to 14 ring atoms, and 6, 10, or 14 electrons are shared in the ring system. And the contained ring atoms are carbon atoms and 1-3 heteroatoms optionally selected from O, N, S. Useful aromatic heterocycle group includes a piperazinyl, a morpholinyl, a piperidinyl, a pyrrolidinyl, a thienyl, a furyl, a pyranyl, a pyrrolyl, an imidazolyl, a pyrazolyl, a pyridyl, including, but not limited to, 2-pyridyl, 3-pyridyl and 4-pyridyl, a pyrazinyl, a pyrimidinyl and the like.

Aromatic heterocycle group may be optionally substituted by 1-5 (e.g., 1, 2, 3, 4 or 5) substituents selected from: a halogen, a $C_{1-4}$ aldehyde group, a $C_{1-6}$ a straight chain or branched chain alkyl, a cyano, a nitro, an amino, a hydroxyl, a hydroxymethyl, a halogen-substituted alkyl (e.g., trifluoromethyl), a halogen-substituted alkoxyl (e.g., trifluoromethoxyl), a carboxyl, a $C_{1-4}$ alkoxyl, a ethoxyformyl, $N(CH_3)$ and a $C_{1-4}$ acyl.

As used herein, "acyl" refers to a group with the structure of formula "—C—(O)—R", wherein R can be selected from an alkyl, an alkenyl or an alkynyl. And R can be optionally substituted. In a particular embodiment, R in "acyl" described herein is substituted with an optionally substituted alkenyl. In a preferred embodiment, R in "acyl" described herein is substituted with optionally substituted $C_2$-$C_4$ alkenyl. In a preferred embodiment, "acyl" according to the present invention is formyl substituted with optionally substituted alkenyl, for example, formyl substituted with vinyl, formyl substituted with $NR_xR_y$-substituted propenyl, wherein $R_x$ and $R_y$ can independently selected from alkyl or H.

As used herein, "acylamino" refers to a group with the structure of formula "—NH—C(O)—R", wherein R can be selected from an alkyl, an alkenyl, an alkynyl, a $NR_xR_y$-substituted alkyl, a $NR_xR_y$-substituted alkenyl, a $NR_xR_y$-substituted alkynyl, a halogen-substituted alkyl, a cyano-substituted alkenyl, wherein $R_x$ and $R_y$ are independently selected from an alkyl or an alkenyl. In a particular embodiment, R in "acylamino" described herein is substituted with an alkenyl. In a preferred embodiment, R in "acylamino" described herein is substituted with $C_2$-$C_4$ alkenyl. In a preferred embodiment, "acylamino" according to the present invention is formylamino substituted with vinyl.

As used herein, "optionally substituted" means that the group modified by the term can be optionally substituted by 1-5 (e.g., 1, 2, 3, 4, or 5) substituents selected from: a halogen, a $C_{1-4}$ aldehyde group, a $C_{1-6}$ straight chain or branched chain alkyl, a cyano, a nitro, an amino, a hydroxyl, a hydroxymethyl, a halogen-substituted alkyl (e.g., trifluoromethyl), a halogen-substituted alkoxyl (e.g., trifluoromethoxyl), a carboxyl, a $C_{1-4}$ alkoxyl, an ethoxyformyl, $N(CH_3)$ and a $C_{1-4}$ acyl.

Compounds of the Present Invention

The inventors have synthesized a series of candidates possessing EGFR inhibitory activity. A series of 7(8H)-pteridinone compounds with novel structure were designed and synthesized through optimization of structure of the obtained candidate compounds, and structurally characterized. Biological activities and physical-chemical properties of this series of compounds were tested, and a series of compounds capable of selectively inhibiting EGFR T790M mutation and possessing good druggability were obtained. Among these compounds, $IC_{50}$ values of inhibitory activity of compound ZW-39 on EGFR-T790M/L858R kinase was 3.9 nM, $IC_{50}$ values of inhibiting proliferation of H1975 cells (non-small cell lung cancer cells, EGFR-T790M/L858R) was 9 nM, and its solubility in water (20 mM phosphate buffer, pH 6.8) was 1367 μg/mL.

After further research, the inventors found that when judging a candidate compound, not only the absolute activity but also the solubility of the candidate compound should be taken into consideration, that is, the druggability of a candidate compound. For evaluating a candidate compounds as a whole, ratio of the solubility of a candidate compound to $IC_{50}$ value of EGFR-T790M/L858R kinase inhibitory activity (ratio 1) and ratio of the solubility of the candidate compound to $IC_{50}$ value of inhibiting proliferation of H1975 cell (ratio 2) was creatively adopted by the inventors as criteria, and selective EGFR inhibitor AZD9291 of the third generation, which is currently in Phase II clinical trials, was used as a positive control, thereby identifying a series of excellent candidate compounds.

In a particular embodiment, the compound of the present invention is a compound of the following general formula I or a pharmaceutically acceptable salt thereof:

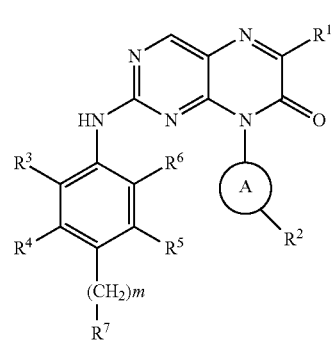

I wherein $R_1$ is independently selected from a group consisting of a hydrogen, substituted or unsubstituted $C_1$-$C_{10}$ alkyl, $C_2$-$C_6$ alkenyl, $C_2$-$C_6$ alkynyl, optionally substituted $C_3$-$C_8$ cycloalkyl, substituted or unsubstituted aryl, substituted or unsubstituted benzyl, substituted or unsubstituted heterocyclyl, substituted or unsubstituted aromatic heterocyclyl;

A is a divalent radical —$(CR_aR_b)_n$-A'— or absent, wherein $R_a$ and $R_b$ are independently selected from a group consisting of H, a $C_{1-3}$ alkyl, a halogen, and n is an integer from 0 to 3;

A' is a benzene ring, a five- or six-membered heterocycle or a $C_3$-$C_8$ cycloalkyl;

$R^2$ is independently selected from a group consisting of a hydrogen, unsubstituted or halogen-substituted $C_1$-$C_4$ alkyl, nitro, amino, halogen, $C_1$-$C_6$ alkoxy, optionally substituted acyloxy, optionally substituted acylamino, optionally substituted acyl; wherein, when A' is a benzene ring, $R^2$ is meta-substituted;

m is an integer from 0 to 3;

$R^7$ is independently selected from a substituted or unsubstituted $NH_2$, a substituted or unsubstituted heterocyclyl, a substituted or unsubstituted aromatic heterocyclyl, a substituted or unsubstituted $C_1$-$C_{10}$ alkyl;

$R^3$, $R^4$, $R^5$ and $R^6$ are independently selected from a group consisting of H, a halogen, a substituted or unsubstituted $C_1$-$C_6$ (preferably $C_1$-$C_3$)alkoxy, a substituted or unsubstituted $C_1$-$C_6$ (preferably $C_1$-$C_3$)alkyl, $NR_cR_d$; wherein each of $R_c$ and $R_d$ is independently selected from $C_1$-$C_3$ alkyl;

wherein, when $R^1$ is H and m is 0, $R^3$, $R^4$, $R^5$ and $R^6$ are not H at the same time;

when $R^1$ is H, m is 0, A' is a benzene ring and $R^7$ is

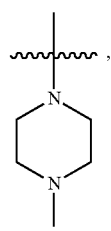

if one of $R^3$ and $R^6$ is a methoxy, the other can not be H.

In a preferred embodiment, $R^1$ is independently selected from a hydrogen, substituted or unsubstituted $C_1$-$C_{10}$ alkyl (preferably $C_1$-$C_6$ alkyl), substituted or unsubstituted phenyl, substituted or unsubstituted benzyl, optionally substituted $C_3$-$C_8$ cycloalkyl; A' is a benzene ring, a five- or six-membered nitrogen-containing heterocycle; $R^2$ is independently selected from a $C_1$-$C_3$ alkyl, $C_2$-$C_4$ alkenyl substituted acylamino, substituted or unsubstituted $C_2$-$C_4$ alkenyl substituted acyl; $R^7$ is selected from a group consisting of:

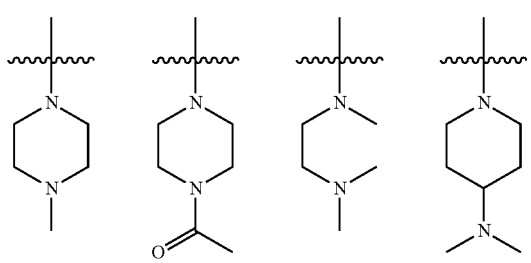

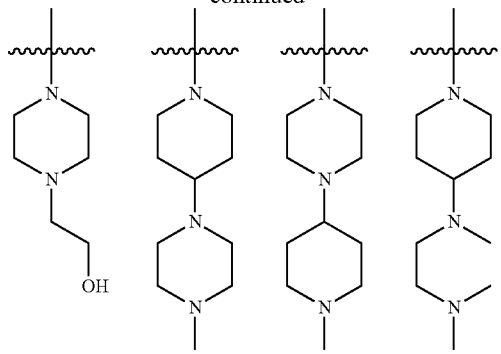

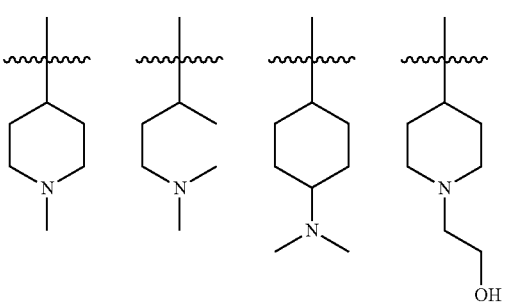

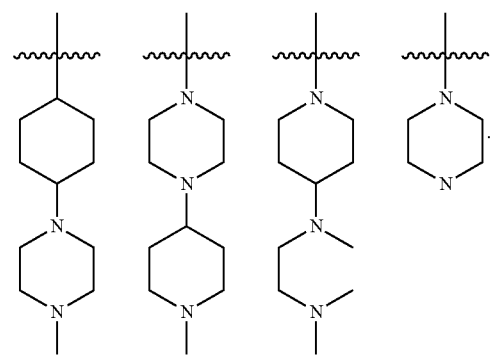

$R^3$, $R^4$, $R^5$ and $R^6$ are independently selected from a group consisting of H, a substituted or unsubstituted $C_1$-$C_6$ (preferably $C_1$-$C_3$) alkoxy, a substituted or unsubstituted $C_1$-$C_6$ (preferably $C_1$-$C_3$) alkyl.

In a particular embodiment, following compounds are provided in the present invention:

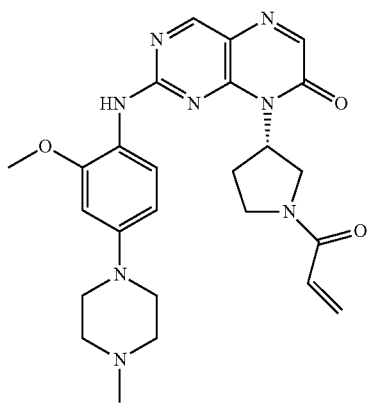

33
-continued
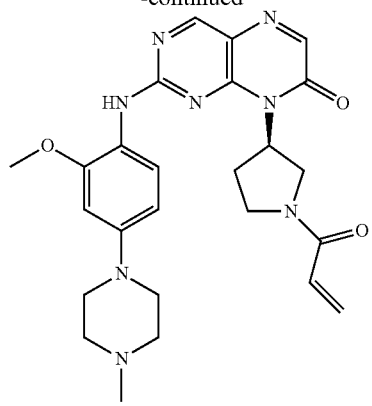
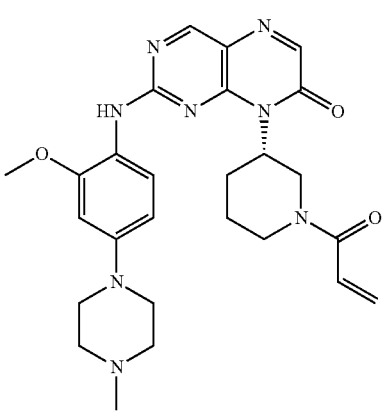
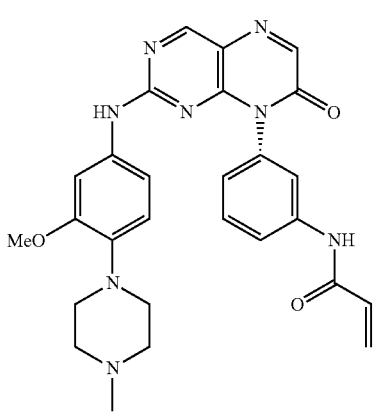
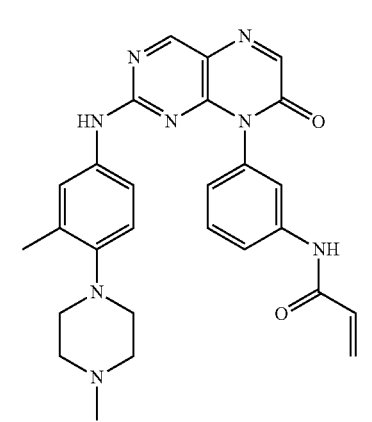
34
-continued
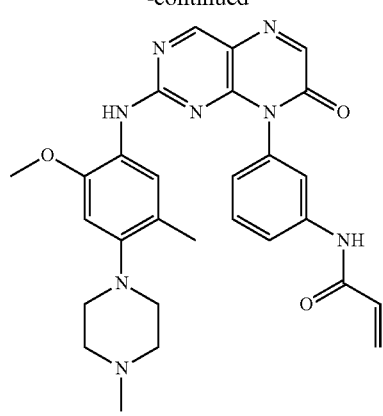
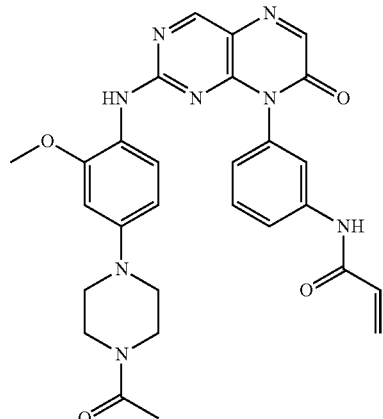
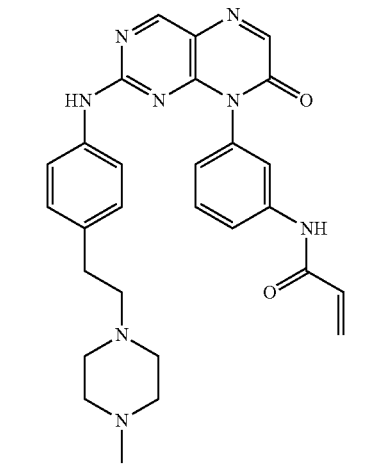
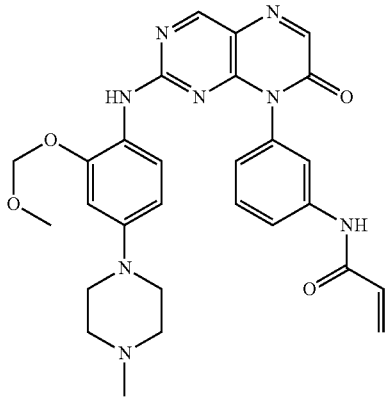

35
-continued
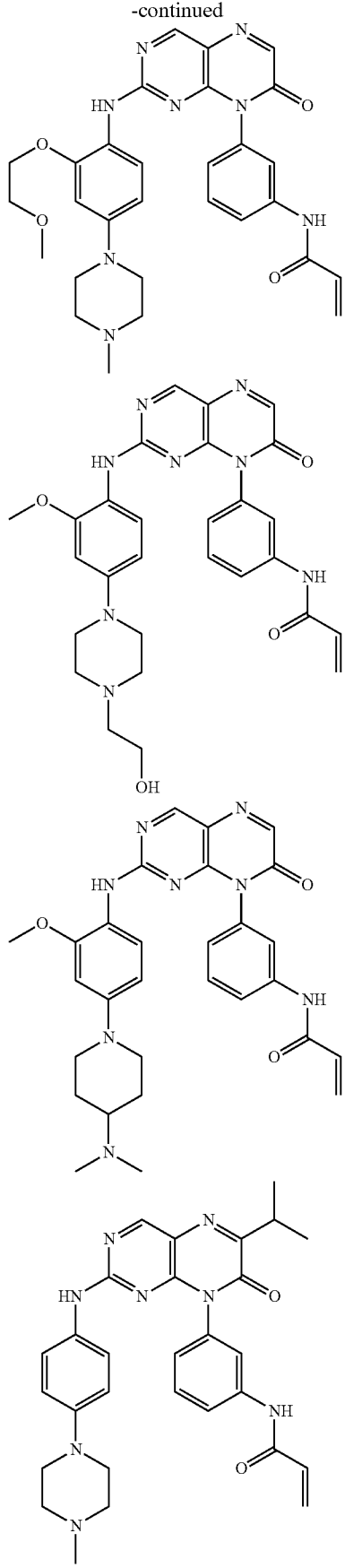
36
-continued
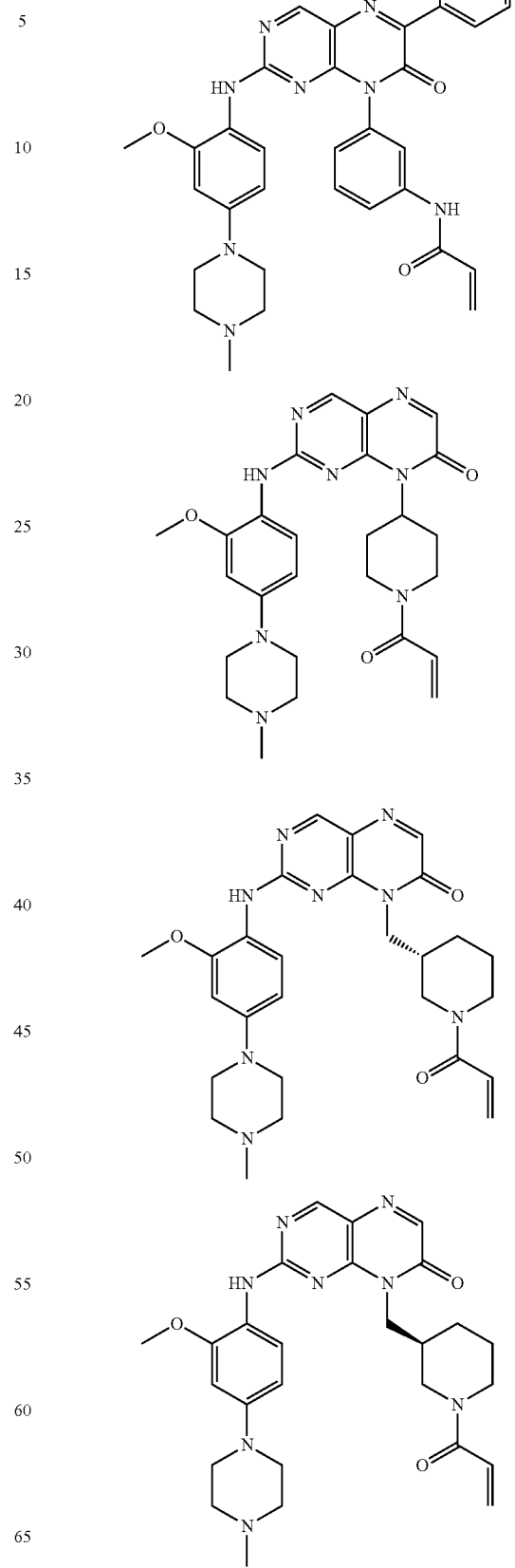

| 37 | 38 |
|---|---|
| -continued | -continued |
| 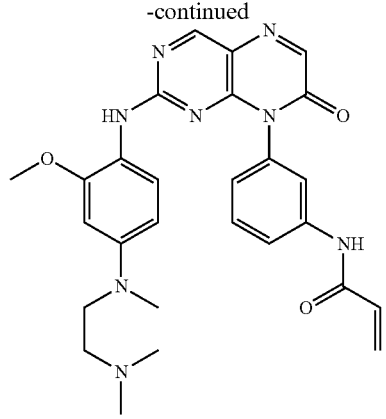 | 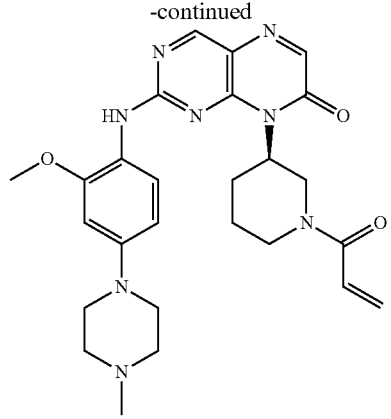 |
| 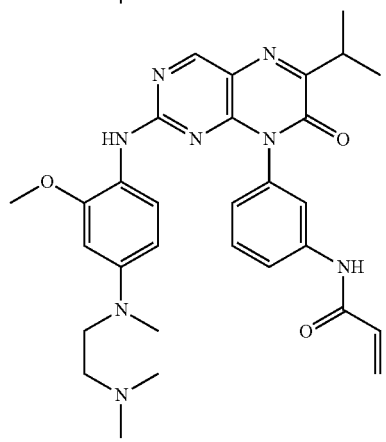 | 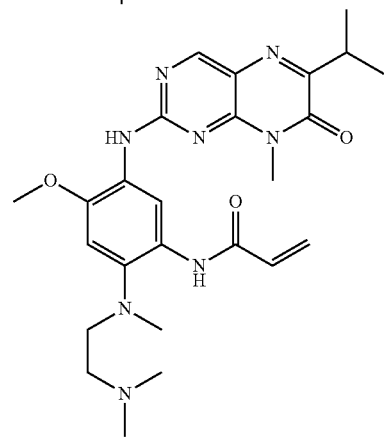 |
| 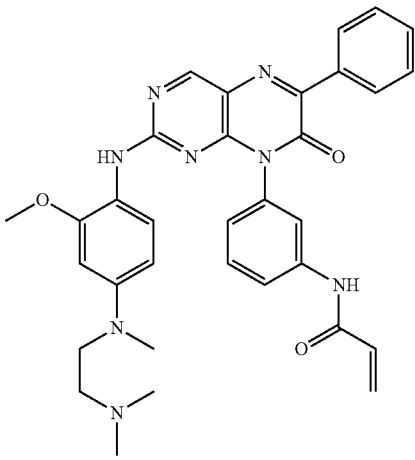 | 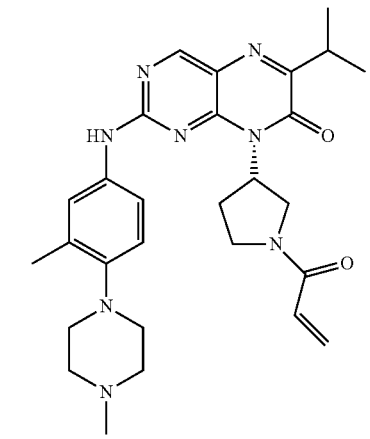 |
| 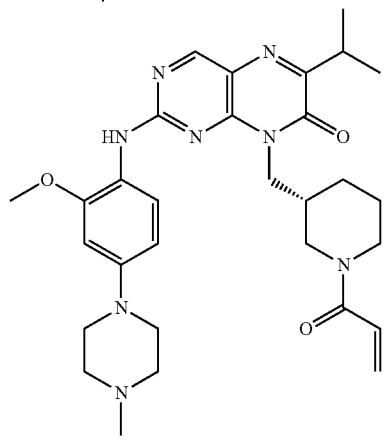 | 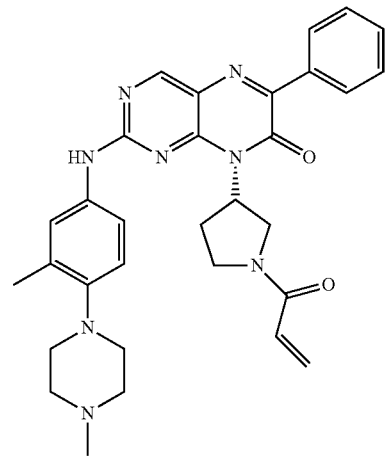 |

39
-continued
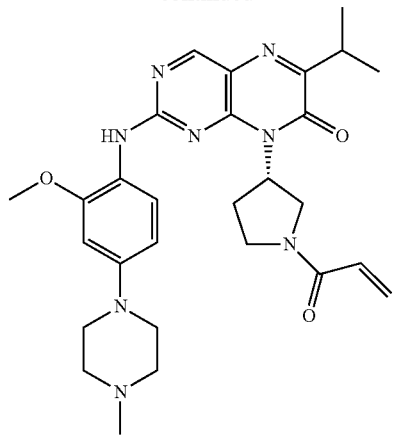
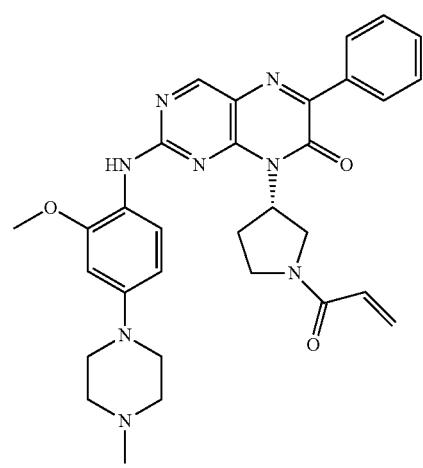
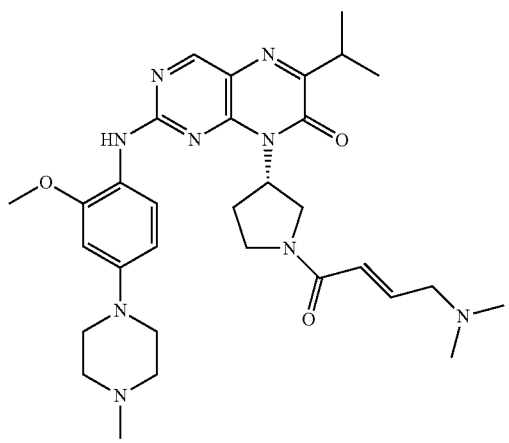
40
-continued
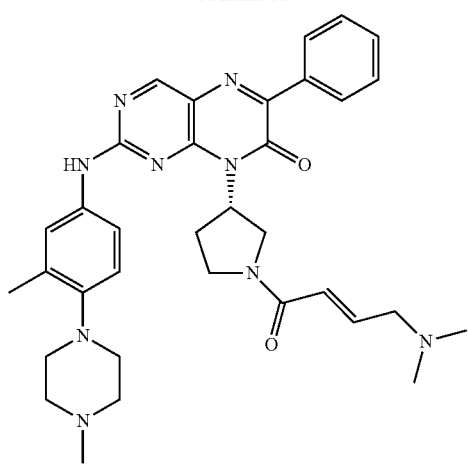
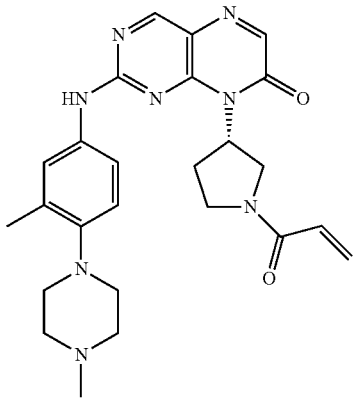
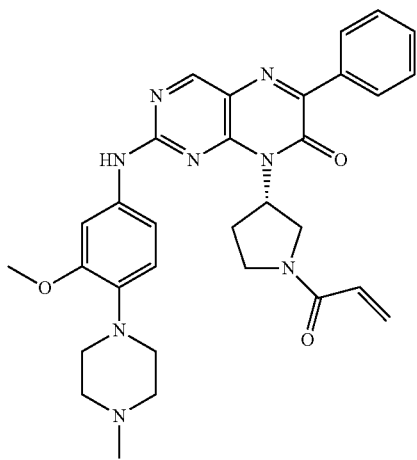

41
-continued
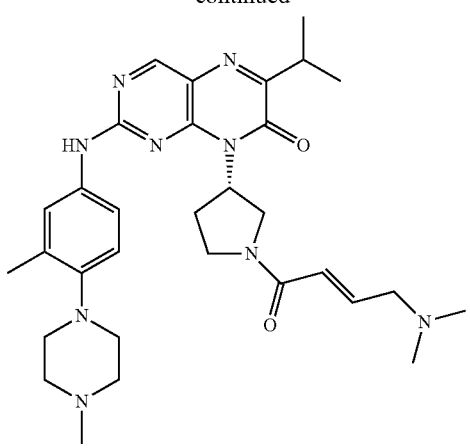
42
-continued
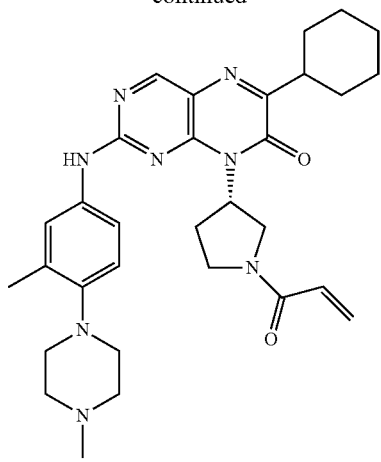
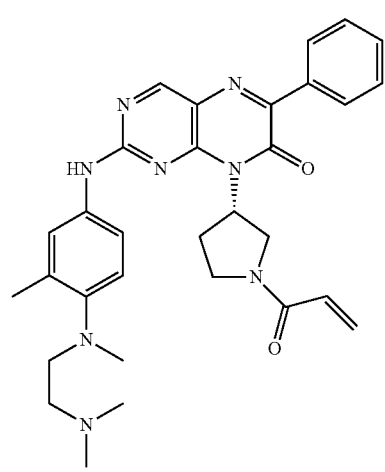
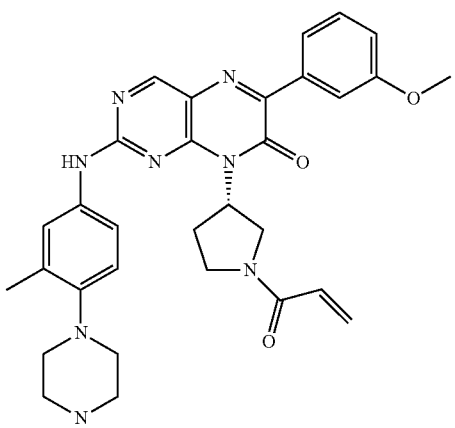
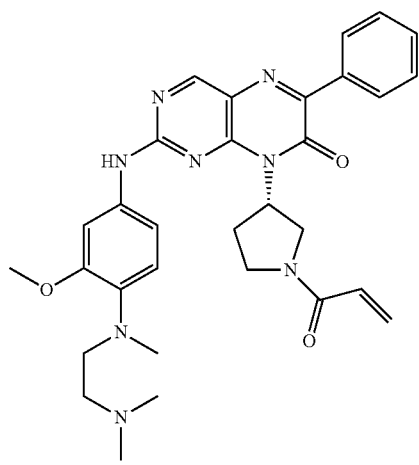
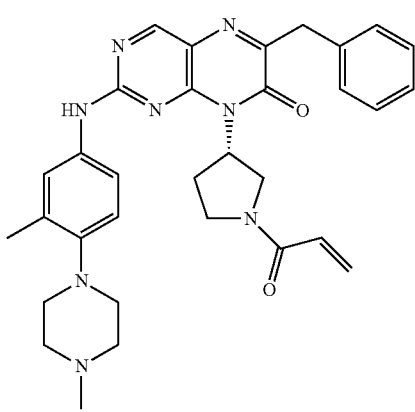

43
-continued
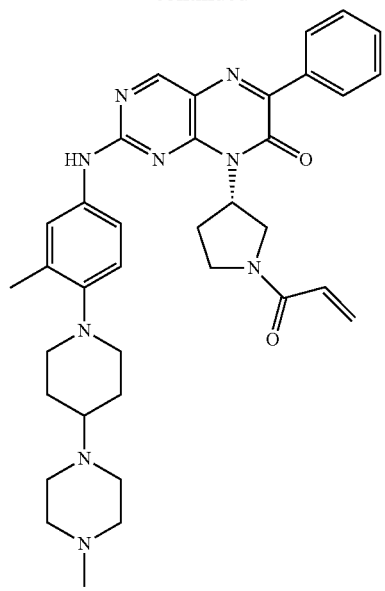
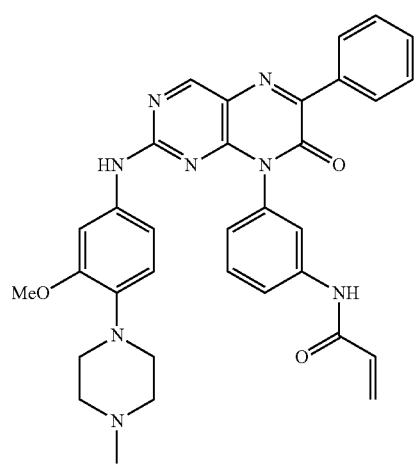
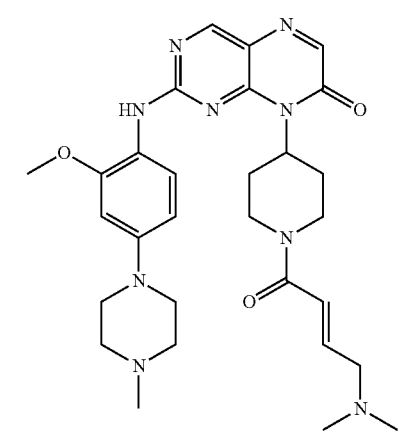
44
-continued
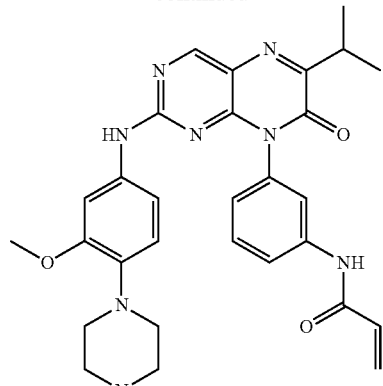
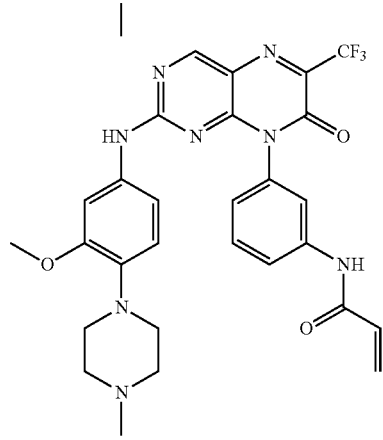
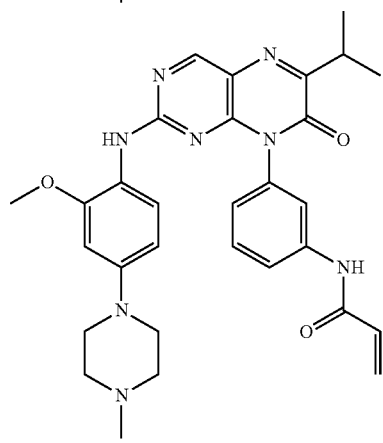
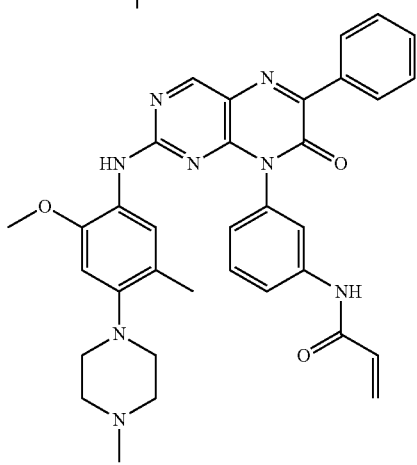

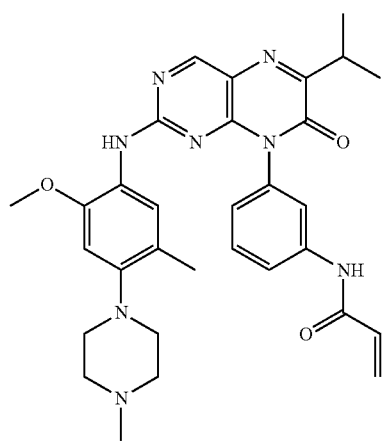
45
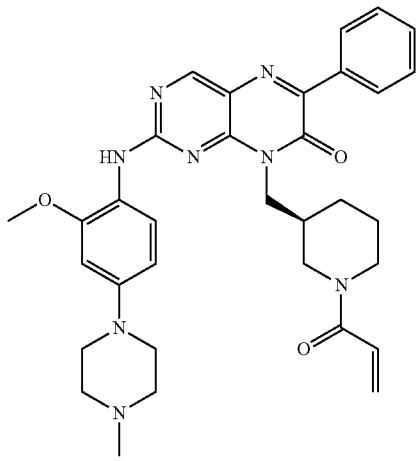
46
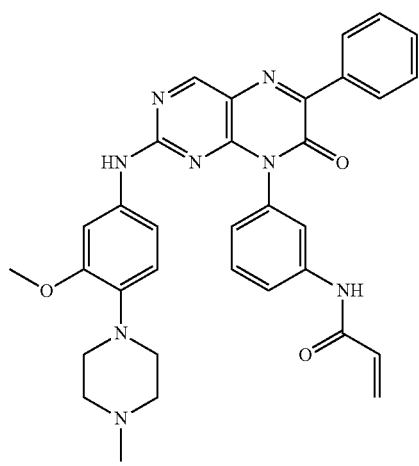
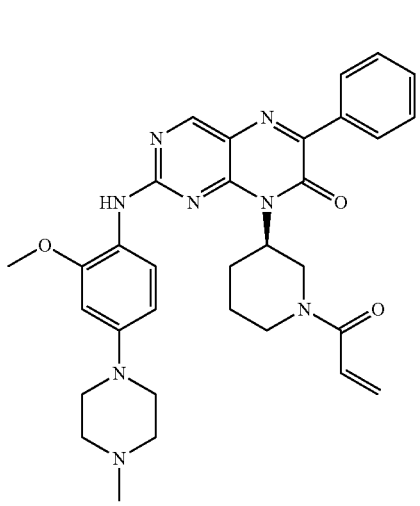
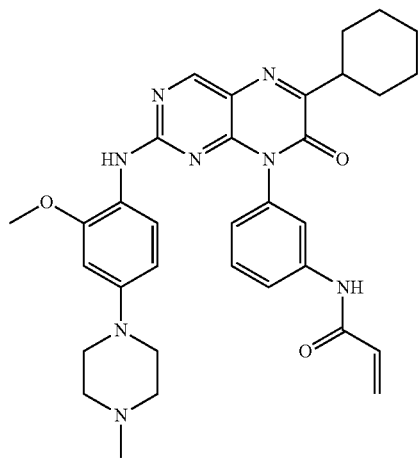

47
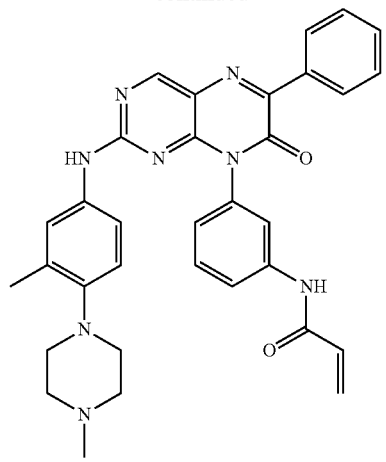
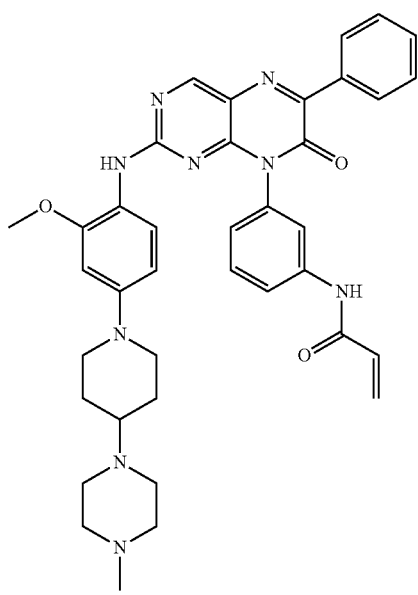
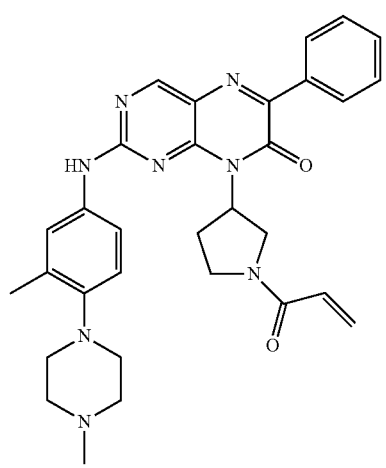
48
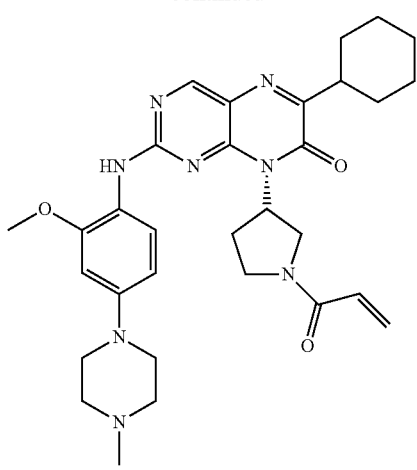
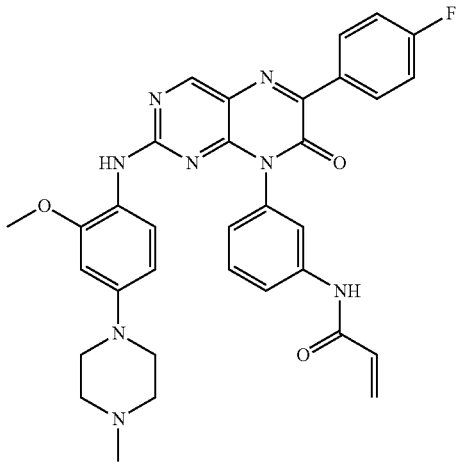

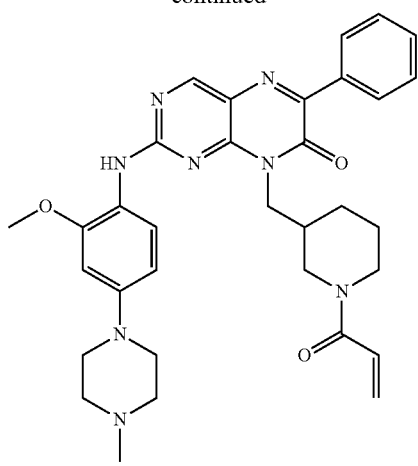

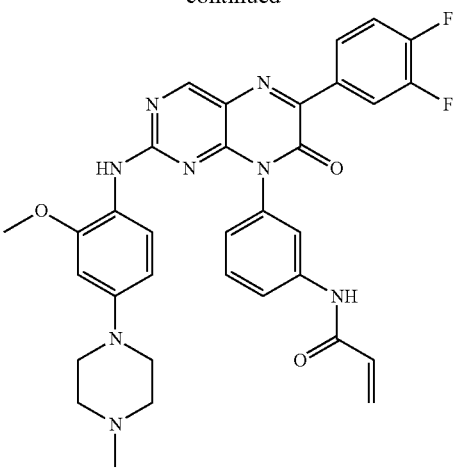

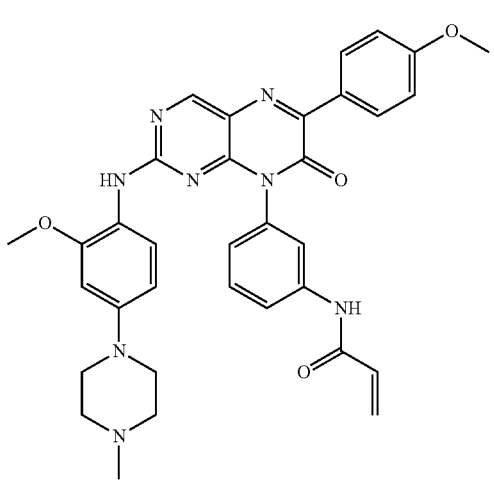

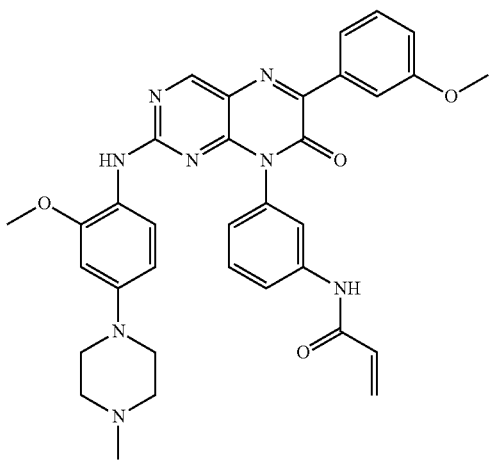

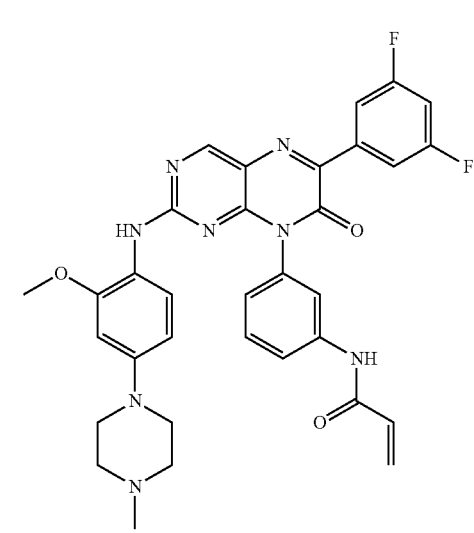

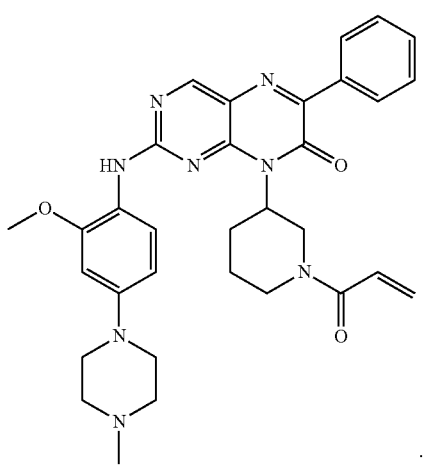

In a further preferred embodiment, $R^1$ is independently selected from a hydrogen, substituted or unsubstituted $C_1$-$C_6$ alkyl, or substituted or unsubstituted phenyl; n=0; A' is a benzene ring, or a five-membered nitrogen-containing heterocycle; $R^2$ is independently selected from a $C_2$-$C_4$ alkenyl substituted acylamino, or $C_2$-$C_4$ alkenyl substituted acyl; m is an integer from 0 to 2; $R^7$ is selected from:

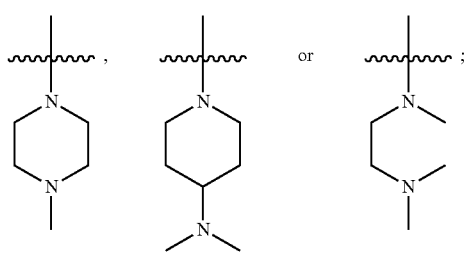
$R^3$, $R^4$, $R^5$ and $R^6$ are independently selected from a group consisting of H, a substituted or unsubstituted $C_1$-$C_3$ alkoxy, a substituted or unsubstituted $C_1$-$C_3$ alkyl.
In a preferred embodiment, following compounds are provided in the present invention:
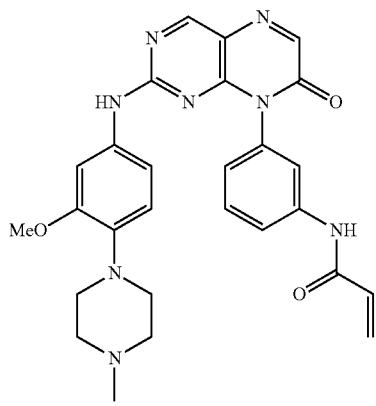
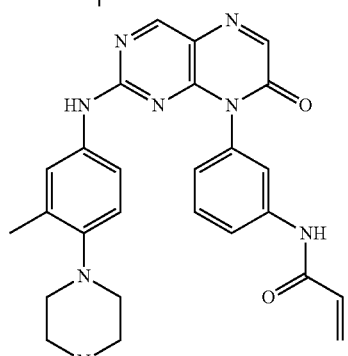
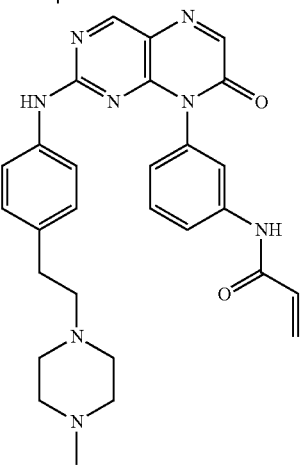
-continued
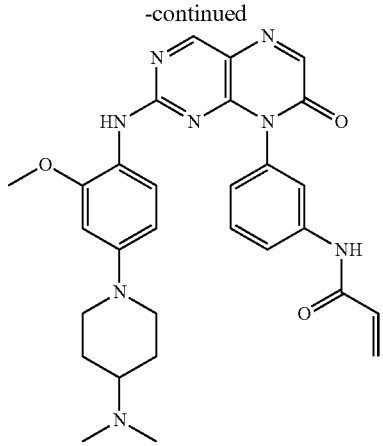
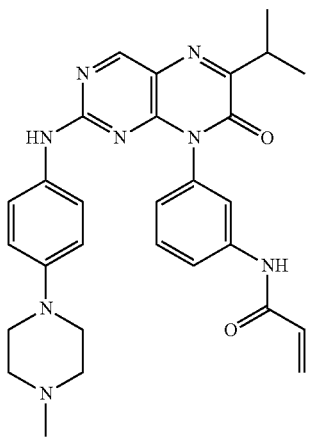
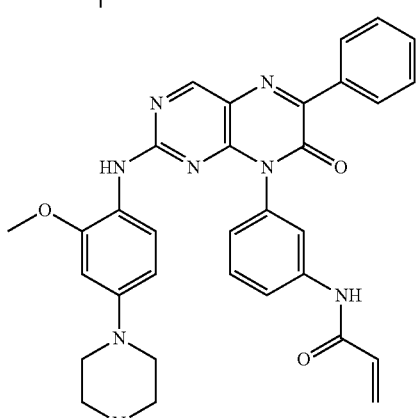
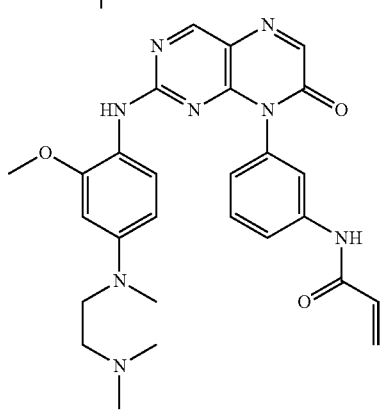

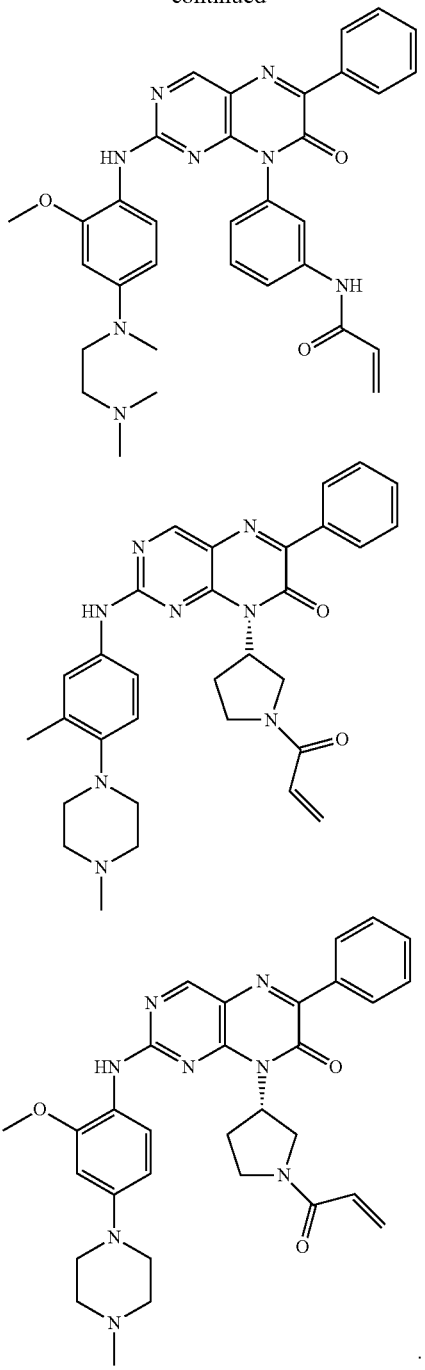

Based on the above compounds, a pharmaceutical composition is provided in the present invention, wherein the composition comprises a compound of formula I or a pharmaceutical acceptable salt thereof of the present invention and a pharmaceutically acceptable carrier or excipient.

The example of the pharmaceutically acceptable salt of the compound of the invention includes, but not limited to, inorganic salts and organic salts, for example, hydrochloride, hydrobromide, sulfate, citrate, lactate, tartrate, maleate, fumarate, mandelate and oxalate; and inorganic and organic salts formed with base, such as sodium hydroxyl, tri(hydroxymethyl) aminomethane (TRIS, tromethamine) and N-methyl glucamine.

The skilled in the art can determine the optimal dosage of each active ingredient in the pharmaceutical compositions of the invention, although the individual's need differs. Generally, the compounds of the present invention or a pharmaceutically acceptable salt thereof are administered orally to a mammal in a daily dose of about 0.0025 to 50 mg/kg body weight, preferably, administered orally about 0.01 to 10 mg per kg. For example, a unit oral dose may comprise about 0.01 to 50 mg, preferably about 0.1 to 10 mg of compounds of the invention. A unit dose may be administered once or more times, one or more tablets a day, with each tablet containing about 0.1 to 50 mg, preferably about 0.25 to 10 mg of the compounds of the invention or a solvate thereof.

The pharmaceutical composition of the invention may be formulated into forms suitably for various administration routes, including, but not limited to, parenteral, subcutaneous, intravenous, intramuscular, intraperitoneal, transdermal, buccal, intrathecal, intracranial, intranasal or topical administration, for treating cancer and other diseases. The administration amount is the amount effective to ameliorate or eliminate one or more diseases. For treating a specific disease, the effective amount is the amount sufficient for ameliorating or alleviating disease relevant symptoms. Such amount can be administered in a single dose or according to the effective therapeutic schedule. The administration amount may be effective in curing diseases, but usually the purpose is to ameliorate symptoms of diseases. Generally, administration needs to be repeated for achieving the amelioration of symptoms. The dose can be determined according to the age, healthy status and weigh of the patient, concurrent treatment, frequency of treatment, and the desired therapeutic benefit.

The pharmaceutical formulations of the invention may be administered to any mammal, as long as the compounds of the present invention are effective to them. In the mammals, human being is the most important.

The compound or pharmaceutical composition of the present invention may be useful in the treatment or prevention of various diseases mediated by epidermal growth factor receptor kinase (EGFR). Herein, the EGFR-mediated disease is various cancers. The cancers include, but are not limited to, non-small cell lung cancer, breast cancer, prostate cancer, glial cell tumors, ovarian cancer, head and neck squamous cell carcinoma, cervical cancer, esophageal cancer, liver cancer, kidney cancer, pancreatic cancer, colon cancer, skin cancer, leukemia, lymphoma, gastric cancer, multiple myeloma, and solid tumors.

The pharmaceutical formulations of the invention can be prepared in a known manner, e.g. by conventional mixing, granulating, tableting, dissolving, or lyophilizing processes. When manufacturing oral formulation, a solid excipient and an active compound can be combined, and the mixture can be ground optionally. If necessary, appropriate additives can be added, and the mixture can be processed into particles for obtaining tablets or troche cores.

Suitable excipients, particularly fillers, include for example, sugars, such as lactose or sucrose, mannitol or sorbitol; cellulose preparations or calcium phosphates, such as tricalcium phosphate or calcium hydrogen phosphate; and a binder, such as starch paste, including corn starch, wheat starch, rice starch, potato starch, gelatin, tragacanth, methyl cellulose, hydroxypropyl methyl cellulose, sodium carboxymethyl cellulose, or polyvinyl pyrrolidone. If desired, is integrating agent, such as, the above-mentioned starches as well as carboxymethyl starch, cross-linked polyvinyl pyrrolidone, agar, or alginic acid or a salt thereof such as sodium alginate, can be added. Adjuvants especially includes flow modifier and lubricants, such as silica, talc, stearates such as magnesium and calcium stearate, stearic acid or polyethylene glycol. If necessary, the troche core can be coated suitably to be resistant to gastric juices. For this purpose, concentrated saccharide solutions may be applied, which may contain gum arabic, talc, polyvinylpyrrolidone, polyethylene glycol and/or titanium dioxide, lacquer solutions, and suitable organic solvents or solvent mixtures. For preparing gastric juice-resistant coatings, suitable cellulose solutions may be used, such as cellulose acetate phthalate or hydroxypropylmethyl cellulose phthalate. Dyestuffs or pigments may be added to the tablets or troche cores coating, for example, for identifying or characterizing the dosage combinations of active ingredients.

Accordingly, a method for treating EGFR mediated diseases is provided, comprising administering the compound of the invention or the pharmaceutical composition comprising the compound of the invention to a object in need thereof.

The administration methods include, but not limited to, those methods known in the art, which can be determined according to the condition of the patient, including, but not limited to, parenteral, subcutaneous, intravenous, intramuscular, intraperitoneal, transdermal, buccal, intrathecal, intracranial, intranasal or topical administration.

Use of the compound of the present invention for manufacturing a medicament for treating EGFR mediated diseases is also included in the present invention.

The technical solutions of the present invention are further described below with reference to specific implementation examples. However, the following embodiments are not intended to limit the present invention. All the application methods adopted according to the principles and technical solutions of the present invention fall within the scope of the present invention. In the following examples, experimental methods with no specific conditions are specified, usually according to the usual conditions or according to the manufacturer's suggested conditions. Unless otherwise indicated, percentages and parts are by weight.

Material and Method

Synthesis of 7(8H)-pteridinone Compounds of the Present Invention

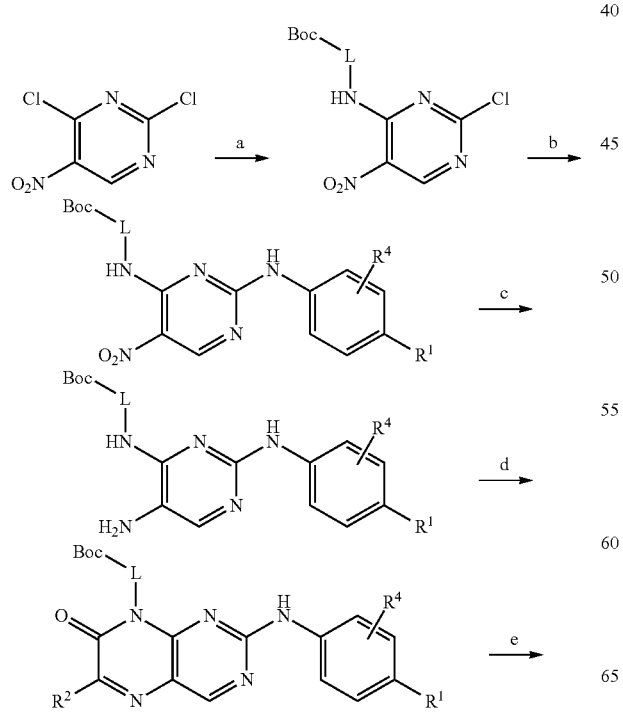

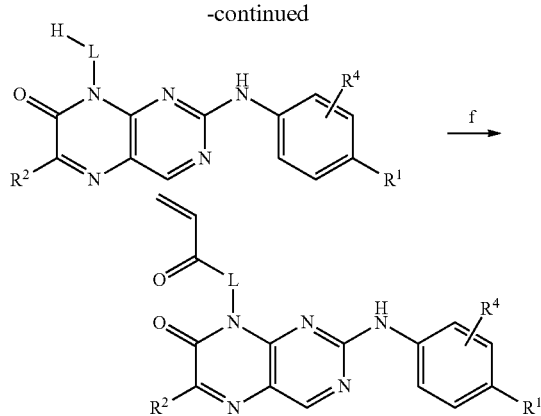

Reagents and conditions: (a) amine, DIPEA, 1,4-dioxane, r.t.; (b) ArNH$_2$, DIPEA, 1,4-dioxane, r.t.; (c) Pd/C, H$_2$, EtOH; (d) R$^2$COCOOEt, HOAc, EtOH, reflux; (e) trifluoroacetic acid, CH$_2$Cl$_2$, 0° C.-r.t.; (f) acid chloride, Et$_3$N, CH$_2$Cl$_2$, 0° C.-r.t. or acid chloride, 1-methyl-2-pyrrolidone, CH$_3$CN, 0° C.-r.t.

In the above preparation procedure, R$^1$, R$^2$, R$^3$, R$^4$ are defined as described above. Various starting compounds routinely obtained in the art as raw material can be used by a skilled person in the art according to actual needs to prepare the compound of the present invention.

EXAMPLE

Example 1

The particular method for steps a-f as said above is shown as follows:

Synthesis of tert-butyl (3-(2-chloro-5-nitropyrimidyl-4-amino)phenyl)carbamate

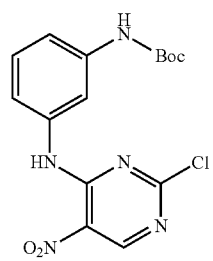 [SMILES: CC(C)(C)OC(=O)Nc1cccc(Nc2nc(Cl)ncc2[N+](=O)[O-])c1]

2,4-dichloro-5-nitro-pyrimidine (3.80 g, 19.59 mmol) was placed into a 100 mL round bottom flask, 80 mL of 1,4-dioxane was added, and stirred at room temperature. Tert-butyl (3-aminophenyl) carbamate (4 g, 19.21 mmol) and N,N-diisopropylethylamine (2.98 g, 23.05 mmol) were dissolved in 20 mL of 1,4-dioxane. The resulting solution was added dropwise into the reaction solution as said above. Upon completion of addition, the resulting mixture was stirred at room temperature for 0.5 h, and TLC showed that the raw material was completely conversed. The solvent was removed by rotary evaporation, and the crude product was separated through silica gel column chromatography (petroleum ether/ethyl acetate=10:1, v/v) to obtain tert-butyl (3-(2-chloro-5-nitropyrimidyl-4-amino)phenyl)carbamate as orange solids (5.9 g, yield 84%). $^1$H NMR (400 MHz, DMSO-d$_6$): δ10.37 (s, 1H), 9.48 (s, 1H), 9.13 (s, 1H), 7.67 (s, 1H), 7.31 (m, 2H), 7.15 (m, 1H), 1.48 (s, 9H).

Synthesis of tert-butyl (3-((2-(methoxymethoxy)-4-(4-methyl-1-piperazinyl) phenyl)amino)-5-nitro-4-pyrimidinyl)amino)phenyl)carbamate

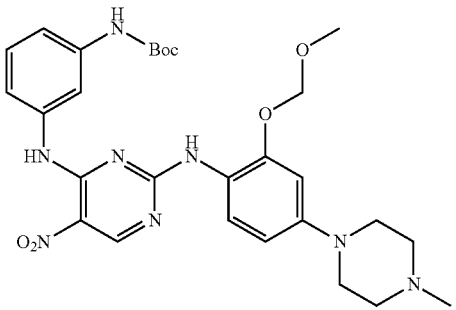 [SMILES: COCOc1cc(N2CCN(C)CC2)ccc1Nc1ncc([N+](=O)[O-])c(Nc2cccc(NC(=O)OC(C)(C)C)c2)n1]

tert-butyl-3-(2-chloro-5-nitropyrimidin-4-amino)phenyl-carbamate (902 mg, 2.47 mmol), 2-(methoxymethoxy)-4-(4-methyl-1-piperazinyl)-aniline (775 mg, 2.47 mmol) and DIPEA (956 mg, 7.40 mmol) were weighed into a 100 ml of round bottom flask. 50 ml of tetrahydrofuran was added, heated to reflux and mixed overnight. After the reaction was completed, the solvent was removed by rotary evaporation, diluted with water and extracted with ethyl acetate (100 mL×2). The organic phase was washed with saturated ammonium chloride solution (50 mL×2) and saturated sodium chloride solution, and dried over sodium sulfate. The solvent was removed by rotary evaporation and the crude product was purified by column chromatography on silica gel (dichloromethane/methanol=30:1, v/v) to give tert-butyl (3-((2-(methoxymethoxy)-4-(4-methyl-1-piperazinyl)phenyl)amino)-5-nitro-4-pyrimidinyl)amino)phenyl)carbamate as orange-red solid, 945 mg, yield 66%. $^1$H NMR (400 MHz, DMSO-$d_6$): δ10.25 (s, 1H), 9.44 (s, 1H), 9.28 (s, 1H), 9.04 (s, 1H), 7.54 (s, 1H), 7.42 (d, J=8.8 Hz, 1H), 7.23-7.20 (m, 2H), 7.08 (t, J=8.0 Hz, 1H), 6.70 (s, 1H), 6.43 (d, J=8.8 Hz, 1H), 5.15 (s, 2H), 3.32 (s, 3H), 3.11 (br, 4H), 2.46 (br, 4H), 2.23 (s, 3H), 1.46 (s, 9H).

Synthesis of tert-butyl (3-(2-((2-(methoxymethoxy)-4-(4-methyl-1-piperazinyl) phenyl)amino)-7-oxo-8(7H)-pteridinyl)phenyl)carbamate

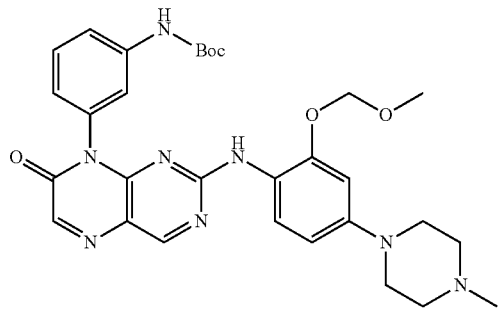 [SMILES: COCOc1cc(N2CCN(C)CC2)ccc1Nc1ncc2ncc(=O)n(-c3cccc(NC(=O)OC(C)(C)C)c3)c2n1]

tert-butyl (3-((2-((2-(methoxymethoxy)-4-(4-methyl-1-piperazinyl)phenyl)amino)-5-nitro-4-pyrimidinyl)amino)phenyl)carbamate (940 mg, 1.62 mmol) was weighed into a 400 mL round bottom flask. 120 mL of ethanol, 100 mL of methylene chloride and 250 mg of palladium on carbon (10% Pd) were added. Hydrogen was ventilated and the reaction system was stirred for 8 hours at room temperature. After the reaction was completed, the reaction mixture was suction-filtered, the filtrate was spin-dried, and the product was directly used in the next reaction without purification.

The product from the previous reaction was placed in a 50 mL round bottom flask and 1.45 mL of glacial acetic acid and 25 mL of absolute ethanol were added followed by ethyl glyoxylate (50% in toluene) (0.495 mL, 2.43 mmol), heated to reflux and stirred overnight. After the reaction was completed, the solvent was removed by rotary evaporation and 15 mL of ethanol was added for recrystallization. Solids precipitated and were suction-filtered. The filter cake was washed with ethanol, aqueous ammonia and deionized water and dried to give tert-butyl (3-(2-((2-(methoxymethoxy)-4-(4-methyl-1-piperazinyl)phenyl)amino)-7-oxo-8(7H)-pteridinyl)phenyl)carbamate as orange-red solids 452 mg, yield 47%. $^1$H NMR (400 MHz, DMSO-$d_6$): δ9.65 (s, 1H), 8.80 (s, 1H), 8.55 (br, 1H), 8.02 (s, 1H), 7.59 (s, 1H), 7.52 (d, J=8.0 Hz, 1H), 7.43 (t, J=8.0 Hz, 1H), 7.36-7.33 (m, 1H), 6.97 (d, J=8.0 Hz, 1H), 6.65 (d, J=2.0 Hz, 1H), 6.16 (br, 1H), 5.17 (s, 2H), 3.36 (s, 3H), 3.03 (br, 4H), 2.44 (t, J=3.6 Hz, 4H), 2.22 (s, 3H), 1.46 (s, 9H).

Synthesis of 8-(3-aminophenyl)-2-((2-(methoxymethoxy)-4-(4-methyl-1-piperazinyl)phenyl)amino)-7(8H)pteridinone

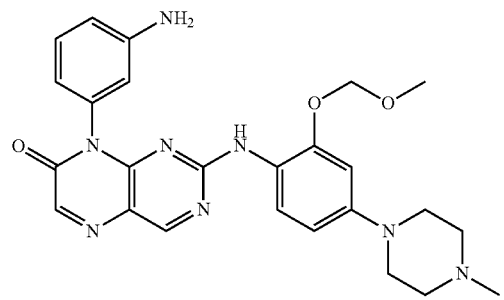 [SMILES: COCOc1cc(N2CCN(C)CC2)ccc1Nc1ncc2ncc(=O)n(-c3cccc(N)c3)c2n1]

tert-butyl (3-((2-((2-(methoxymethoxy)-4-(4-methyl-1-piperazinyl)phenyl)amino)-7-oxo-8(7H)-pteridinyl)phenyl)carbamate (452 mg, 0.77 mmol) was weighed into a 25 mL round bottom flask. 7 mL of methylene chloride was added and 2 mL of trifluoroacetic acid was added in an ice-bath with stirring. The reaction system was stirred for another 1 hour in an ice bath and for 1 hour at room temperature. After the reaction was completed, saturated sodium bicarbonate solution was added to neutralize the solution to pH=9. The filtrate was extracted with dichloromethane. The organic phase was washed with deionized water and saturated sodium chloride solution, and dried, and the solvent was spin-dried. The crude product was purified by column chromatography on silica gel (dichloromethane/methanol=20:1, v/v) to obtain 8-(3-aminophenyl)-2-((2-(methoxymethoxy)-4-(4-methyl-1-piperazinyl)phenyl)amino)-7(8H)pteridinone, orange-red solids 132 mg, yield 35%. MS (ESI) m/z 489.2 [M+H]$^+$.

Synthesis of N-(3-(2-((2-(methoxymethoxy)-4-(4-methyl-1-piperazinyl)phenyl) amino)-7-oxo-8(7H)pteridinyl)phenyl)acrylamide (Compound 9)

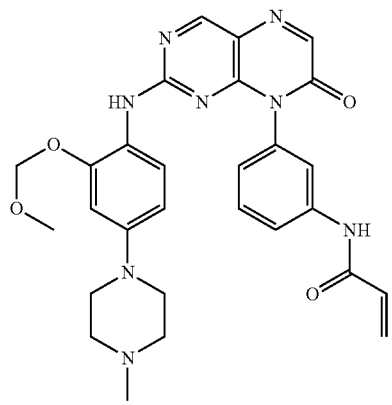 [SMILES: C=CC(=O)Nc1cccc(-n2c(=O)cnc3cnc(Nc4ccc(N5CCN(C)CC5)cc4OCOC)nc32)c1]

8-(3-aminophenyl)-2-(2-(methoxymethoxy)-4-(4-methyl-1-piperazinyl)phenyl)amino)-7(8H)pteridinone (132 mg, 0.270 mmol) was weighed into a 25 mL round bottom flask. 4 mL of N-methylpyrrolidone was added and stirred in an ice bath. Acryloyl chloride (25 μL, 0.297 mmol) was dissolved in 2 mL of acetonitrile and added dropwise to the reaction mixture with a constant pressure dropping funnel. Upon addition, the mixture was stirred for half an hour in an ice bath and then for 2 hours at room temperature. After the reaction was completed, saturated sodium bicarbonate solution was added to the reaction liquid and stirred for another 15 minutes. The reaction mixture was diluted with water and extracted with ethyl acetate. The organic phase was washed with deionized water and saturated sodium chloride solution. After concentration, the residue was purified by column chromatography on silica gel (methylene chloride/methanol/aqueous ammonia=100:5:0.5, v/v) to obtain N-(3-(2-((2-(methoxymethoxy)-4-(4-methyl-1-piperazinyl) phenyl)amino)-7-oxo-8(7H)pteridinyl)phenyl)acrylamide, orange solids 101 mg, yield 69%. $^1$H NMR (400 MHz, DMSO-d$_6$): δ10.40 (s, 1H), 8.81 (s, 1H), 8.53 (br, 1H), 8.03 (s, 1H), 7.85 (d, J=6.4 Hz, 1H), 7.72 (s, 1H), 7.53 (t, J=8.0 Hz, 1H), 7.34-7.33 (m, 1H), 7.10 (d, J=8.0 Hz, 1H), 6.64 (s, 1H), 6.46 (dd, J=16.8, 10.0 Hz, 1H), 6.27 (dd, J=16.8, 1.6 Hz, 1H), 6.13-6.09 (m, 1H), 5.78 (dd, J=10.0, 1.6 Hz, 1H), 5.16 (s, 2H), 3.35 (s, 3H), 3.00 (br, 4H), 2.43 (t, J=4.4 Hz, 4H), 2.22 (s, 3H). HRMS (ESI) (m/z): [M+H]$^+$ calcd for C$_{28}$H$_{31}$N$_8$O$_4$, 543.2468; found, 543.2476.

Following compounds were synthesized using the same or similar synthesis route as described above:

(S)-8-(1-acryloyl-3-pyrrolidinyl)-2-((2-methoxy)-4-(4-methyl-1-piperazinyl)phenyl)amino)-7(8H)pteridinone (Compound 1)

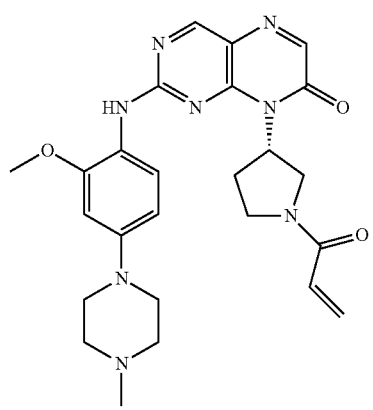 [SMILES: C=CC(=O)N1CC[C@H](n2c(=O)cnc3cnc(Nc4ccc(N5CCN(C)CC5)cc4OC)nc32)C1]

orange-red solids, yield 40%. $^1$H NMR (400 MHz, DMSO-d$_6$): δ8.96 (s, 1H), 8.73 (s, 0.5H), 8.72 (s, 0.5H), 7.86 (s, 0.5H), 7.84 (s, 0.5H), 7.32 (m, 1H), 6.57 (s, 1H), 6.43-6.42 (m, 1H), 6.16 (ddd, J=16.8, 10.0, 2.4 Hz, 1H), 5.72 (dd, J=10.0, 2.4 Hz, 1H), 5.65 (dd, J=10.0, 2.4 Hz, 1H), 4.08 (t, J=10.2 Hz, 0.5H), 3.88-3.82 (m, 0.5H), 3.76 (s, 3H), 3.67-3.62 (m, 1H), 3.58-3.55 (m, 1H), 3.21-3.17 (m, 4H), 2.81-2.71 (m, 1H), 2.68-2.61 (m, 4H), 2.38 (s, 1.4H), 2.34 (s, 1.6H), 2.04-1.96 (m, 2H). HRMS (ESI) (m/z): [M+H]$^+$ calcd for C$_{25}$H$_{31}$N$_8$O$_3$, 491.2519; found, 491.2520. HPLC purity: 95.7%, retention time=9.43 min.

(R)-8-(1-acryloyl-3-pyrrolidinyl)-2-((2-methoxy)-4-(4-methyl-1-piperazinyl)phenyl)amino)-7(8H)pteridinone (Compound 2)

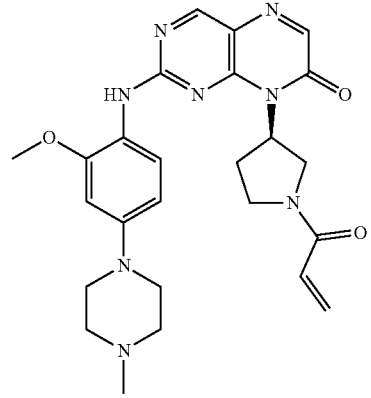 [SMILES: C=CC(=O)N1CC[C@@H](n2c(=O)cnc3cnc(Nc4ccc(N5CCN(C)CC5)cc4OC)nc32)C1]

orange-red solids, yield 40%. $^1$H NMR (400 MHz, DMSO-d$_6$): δ8.94 (s, 1H), 8.72-8.71 (m, 1H), 7.86-7.84 (m, 1H), 7.33 (t, J=8.4 Hz, 1H), 6.56 (s, 1H), 6.42-6.40 (m, 1H), 6.16 (ddd, J=16.8, 10.4, 2.4 Hz, 1H), 5.70 (dd, J=10.4, 2.4 Hz, 1H), 5.65 (dd, J=10.4, 2.4 Hz, 1H), 4.10 (t, J=10.2 Hz, 0.5H), 3.88-3.83 (m, 0.6H), 3.76 (s, 3H), 3.67-3.62 (m, 1H), 3.58-3.55 (m, 1H), 3.15-3.10 (m, 4H), 2.82-2.64 (m, 1H), 2.45 (br, 4H), 2.23 (s, 3H), 2.06-1.96 (m, 1H). HRMS (ESI) (m/z): [M+H]$^+$ calcd for C$_{25}$H$_{31}$N$_8$O$_3$, 491.2519; found, 491.2473.

(S)-8-(1-acryloyl-3-piperidinyl)-2-((2-methoxy)-4-(4-methyl-1-piperazinyl)phenyl)amino)-7(8H)pteridinone (Compound 3)

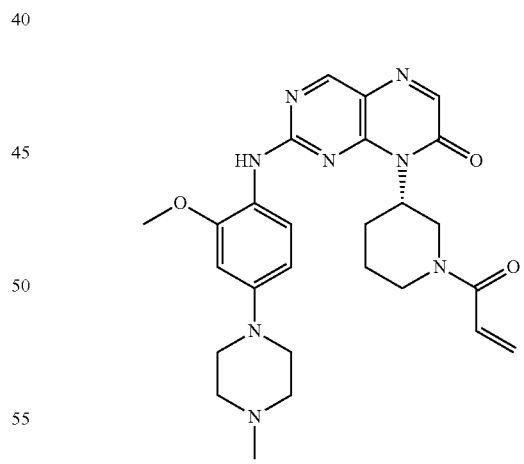

orange-red solids, yield 38%. $^1$H NMR (400 MHz, DMSO-d$_6$): δ9.14 (br, 1H), 8.71 (s, 1H), 7.83 (s, 1H), 7.22-7.21 (m, 1H), 6.80-6.62 (m, 2H), 6.48-6.47 (m, 1H), 6.15-6.08 (m, 1H), 5.71-5.60 (m, 1H), 4.82-4.76 (m, 0.6H), 4.34-4.24 (m, 1H), 3.95-3.92 (m, 1H), 3.74 (s, 3H), 3.14 (br, 4H), 2.46 (br, 4H), 1.64 (br, 2H), 1.34-1.30 (m, 1H). HRMS (ESI) (m/z): [M+H]$^+$ calcd for C$_{26}$H$_{33}$N$_8$O$_3$, 505.2676; found, 505.2676.

61

N-(3-(2-((3-methoxy-4-(methyl-1-piperazinyl)phenyl)amino)-7-oxo-8(7H)-pteridinyl)phenyl)acrylamide (Compound 4)

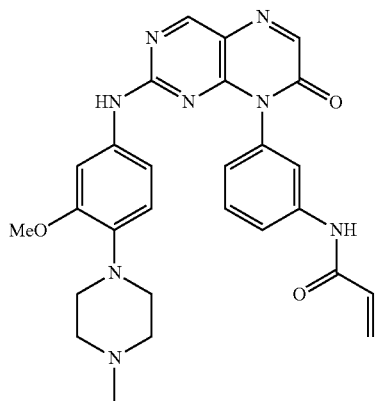 [SMILES: C=CC(=O)Nc1cccc(-n2c(=O)cnc3cnc(Nc4ccc(N5CCN(C)CC5)c(OC)c4)nc32)c1]

red solids, yield 55%. $^1$H NMR (400 MHz, DMSO-d$_6$): δ10.41 (s, 1H), 10.00 (br, 1H), 8.86 (s, 1H), 8.04 (s, 1H), 7.87 (d, J=8.0 Hz, 1H), 7.73 (s, 1H), 7.54 (t, J=8.0 Hz, 1H), 7.11 (d, J=8.0 Hz, 1H), 7.04-6.95 (m, 2H), 6.48-6.42 (m, 2H), 6.27 (dd, J=17.2, 2.0 Hz, 1H), 5.77 (dd, J=10.0, 2.0 Hz, 1H), 3.55 (s, 3H), 2.83 (br, 4H), 2.43 (br, 4H), 2.22 (s, 3H). HRMS (ESI) (m/z): [M+H]$^+$ calcd for C$_{27}$H$_{29}$N$_8$O$_3$, 513.2363; found, 513.2362.

N-(3-(2-((3-methoxy-4-(4-methyl-1-piperazinyl)phenyl)amino)-7-oxo)-8(7H)pteridinyl)phenyl)acrylamide (Compound 5)

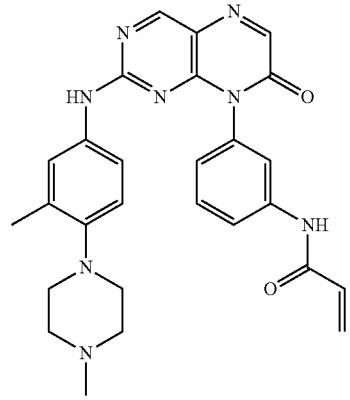 [SMILES: C=CC(=O)Nc1cccc(-n2c(=O)cnc3cnc(Nc4ccc(N5CCN(C)CC5)c(C)c4)nc32)c1]

yellow solids, yield 63%. $^1$H NMR (400 MHz, DMSO-d$_6$): δ10.41 (s, 1H), 10.04 (s, 1H), 8.86 (s, 1H), 8.04 (s, 1H), 7.87 (d, J=8.0 Hz, 1H), 7.76 (s, 1H), 7.55 (t, J=8.0 Hz, 1H), 7.22 (s, 1H), 7.13-7.10 (m, 2H), 6.70-6.69 (m, 1H), 6.45 (dd, J=17.0, 10.2 Hz, 1H), 6.26 (dd, J=17.0, 2.0 Hz, 1H), 5.76 (dd, J=10.2, 2.0 Hz, 1H), 2.70 (br, 4H), 2.44 (br, 4H), 2.23 (s, 3H), 1.97 (s, 3H). HRMS (ESI) (m/z): [M+H]$^+$ calcd for C$_{27}$H$_{29}$N$_8$O$_2$, 497.2413; found, 497.2428.

62

N-(3-(2-4-((2-methoxy-5-methyl-4-(4-methyl-1-piperazinyl)phenyl)amino)-7-oxo-8(7H)-pteridinyl)phenyl)acrylamide (Compound 6)

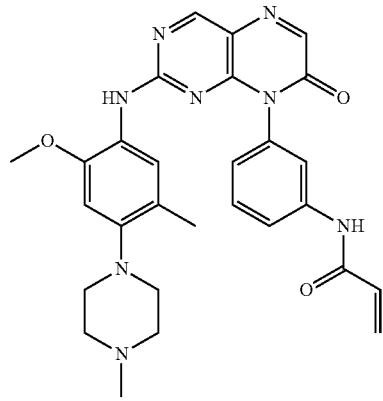 [SMILES: C=CC(=O)Nc1cccc(-n2c(=O)cnc3cnc(Nc4cc(C)c(N5CCN(C)CC5)cc4OC)nc32)c1]

red solids, yield 50%. $^1$H NMR (400 MHz, DMSO-d$_6$): δ10.38 (s, 1H), 8.82 (s, 1H), 8.37 (s, 1H), 8.04 (s, 1H), 7.82 (d, J=8.0 Hz, 1H), 7.74 (s, 1H), 7.53 (t, J=8.0 Hz, 1H), 7.29 (s, 1H), 7.10 (d, J=8.8 Hz, 1H), 6.62 (s, 1H), 6.45 (dd, J=16.8, 2.0 Hz, 1H), 6.25 (dd, J=16.8, 2.0 Hz, 1H), 5.77-5.76 (m, 1H), 3.78 (s, 1H), 2.76 (br, 4H), 2.46 (br, 4H), 2.24 (s, 3H), 1.85 (s, 3H). HRMS (ESI) (m/z): [M+H]$^+$ calcd for C$_{28}$H$_{31}$N$_8$O$_3$, 527.2519; found, 527.2518.

N-(3-(2-((4-(4-acetyl-1-piperazinyl)-2-methoxyphenyl)amino)-7-oxo-8(7H)-pteridinyl)phenyl)acrylamide (Compound 7)

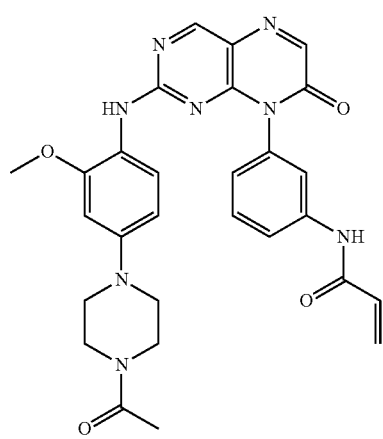 [SMILES: C=CC(=O)Nc1cccc(-n2c(=O)cnc3cnc(Nc4ccc(N5CCN(C(C)=O)CC5)cc4OC)nc32)c1]

red solids, yield 50%. $^1$H NMR (400 MHz, DMSO-d$_6$): δ10.36 (s, 1H), 8.80 (s, 1H), 8.44 (s, 1H), 8.03 (s, 1H), 7.86 (d, J=8.0 Hz, 1H), 7.69 (t, J=2.0 Hz, 1H), 7.52 (t, J=8.0 Hz, 1H), 7.32 (d, J=8.8 Hz, 1H), 7.09 (d, J=8.0 Hz, 1H), 6.57 (d, J=2.4 Hz, 1H), 6.45 (dd, J=17.0, 2.0 Hz, 1H), 6.27 (dd, J=17.0, 10.0 Hz, 1H), 6.09 (br, 1H), 5.77 (dd, J=10.0, 2.0 Hz, 1H), 3.77 (s, 1H), 3.58-3.54 (m, 4H), 3.06-3.00 (m, 4H), 2.05 (s, 3H). HRMS (ESI) (m/z): [M+H]$^+$ calcd for C$_{28}$H$_{29}$N$_8$O$_4$, 541.2312; found, 541.2312.

63

N-(3-(2-((4-(2-(4-methyl-1-piperazinyl)ethyl)phenyl)amino)-7-oxo-8(7H)-pteridinyl)phenyl)acrylamide (Compound 8)

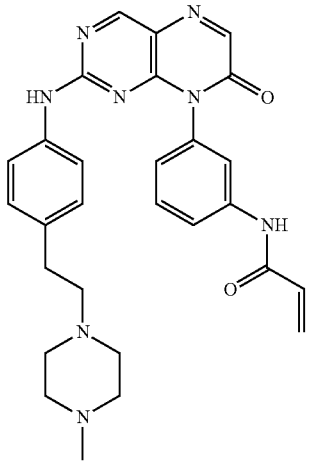 [SMILES: C=CC(=O)Nc1cccc(-n2c(=O)cnc3cnc(Nc4ccc(CCN5CCN(C)CC5)cc4)nc32)c1]

yellow solids, yield 50%. ¹H NMR (400 MHz, DMSO-$d_6$): δ10.41 (s, 1H), 10.13 (s, 1H), 8.88 (s, 1H), 8.07 (s, 1H), 7.88 (d, J=8.0 Hz, 1H), 7.77 (s, 1H), 7.57 (t, J=8.0 Hz, 1H), 7.31-7.30 (m, 2H), 7.14 (d, J=8.0 Hz, 1H), 6.86 (br, 2H), 6.45 (dd, J=16.8, 10.0 Hz, 1H), 6.26 (dd, J=16.8, 2.0 Hz, 1H), 5.77 (dd, J=10.0, 2.0 Hz, 1H), 2.56 (t, J=7.6 Hz, 2H), 2.39-2.31 (m, 9H), 2.15 (s, 3H). HRMS (ESI) (m/z): [M+H]⁺ calcd for $C_{28}H_{31}N_8O_2$, 511.2570; found, 511.2571.

N-(3-(2-((2-(methoxymethoxy)-4-(4-methyl-1-piperazinyl)phenyl)amino)-7-oxo-8(7H)-pteridinyl)phenyl)acrylamide (Compound 9)

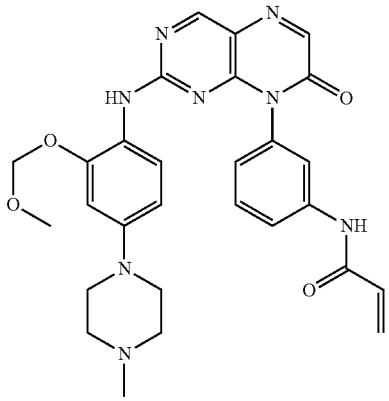 [SMILES: C=CC(=O)Nc1cccc(-n2c(=O)cnc3cnc(Nc4ccc(N5CCN(C)CC5)cc4OCOC)nc32)c1]

orange solids, yield 69%. mp 187.3-188.1° C. ¹H NMR (400 MHz, DMSO-$d_6$): δ10.40 (s, 1H), 8.81 (s, 1H), 8.53 (br, 1H), 8.03 (s, 1H), 7.85 (d, J=6.4 Hz, 1H), 7.72 (s, 1H), 7.53 (t, J=8.0 Hz, 1H), 7.34-7.33 (m, 1H), 7.10 (d, J=8.0 Hz, 1H), 6.64 (s, 1H), 6.46 (dd, J=16.8, 10.0 Hz, 1H), 6.27 (dd, J=16.8, 1.6 Hz, 1H), 6.13-6.09 (m, 1H), 5.78 (dd, J=10.0, 1.6 Hz, 1H), 5.16 (s, 2H), 3.35 (s, 3H), 3.00 (br, 4H), 2.43 (t, J=4.4 Hz, 4H), 2.22 (s, 3H). HRMS (ESI) (m/z): [M+H]⁺ calcd for $C_{28}H_{31}N_8O_4$, 543.2468; found, 543.2476.

64

N-(3-(2-((2-(methoxyethoxy)-4-(4-methyl-1-piperazinyl)phenyl)amino)-7-oxo-8(7H)-pteridinyl)phenyl)acrylamide (Compound 10)

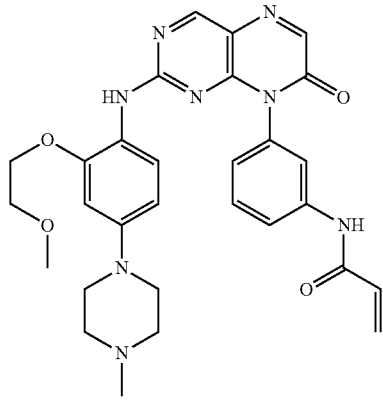 [SMILES: C=CC(=O)Nc1cccc(-n2c(=O)cnc3cnc(Nc4ccc(N5CCN(C)CC5)cc4OCCOC)nc32)c1]

orange-red solids, yield 61%. ¹H NMR (400 MHz, CDCl₃): δ8.78 (s, 1H), 8.65-8.62 (m, 1H), 8.24 (s, 1H), 8.07 (s, 1H), 7.85 (s, 1H), 7.41 (br, 3H), 6.93 (d, J=5.6 Hz, 1H), 6.44 (s, 1H), 6.33 (d, J=17.0 Hz, 1H), 6.10 (dd, J=17.0, 10.4 Hz, 1H), 5.78 (d, J=10.4 Hz, 1H), 4.10 (br, 2H), 3.69 (br, 2H), 3.43 (s, 3H), 3.08 (br, 4H), 2.54 (br, 4H), 2.34 (s, 3H). HRMS (ESI) (m/z): [M+H]⁺ calcd for $C_{29}H_{33}N_8O_4$, 557.2625; found, 557.2621.

N-(3-(2-((4-(4-(2-hydroxyethyl)-1-piperazinyl)-2-methoxyphenyl)amino)-7-oxo-8 (7H)-pteridinyl) phenyl)acrylamide (Compound 11)

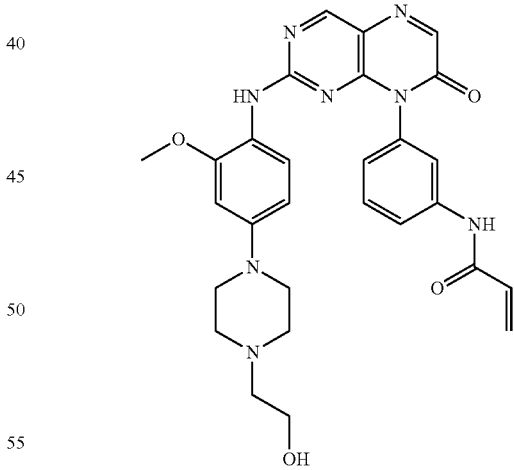

orange solids, yield 53%. ¹H NMR (400 MHz, DMSO-$d_6$): δ10.39 (s, 1H), 8.79 (s, 1H), 8.43 (s, 1H), 8.02 (s, 1H), 7.85 (d, J=7.6 Hz, 1H), 7.71 (s, 1H), 7.52 (t, J=8.0 Hz, 1H), 7.30 (d, J=7.6 Hz, 1H), 7.09 (d, J=8.0 Hz, 1H), 6.52 (s, 1H), 6.45 (dd, J=16.8, 10.0 Hz, 1H), 6.27 (dd, J=16.8, 2.0 Hz, 1H), 6.02 (br, 1H), 5.78 (dd, J=10.0, 2.0 Hz, 1H), 4.43 (t, J=5.2 Hz, 1H), 3.76 (s, 3H), 3.56-3.52 (m, 2H), 3.04 (br, 4H), 2.53 (t, J=4.8 Hz, 4H), 2.44 (t, J=6.0 Hz, 1H). HRMS (ESI) (m/z): [M+H]⁺ calcd for $C_{29}H_{33}N_8O_3$, 543.2468; found, 543.2466.

65

N-(3-(2-((4-(2-(4-methyl-1-piperazinyl)ethyl)phenyl)amino)-7-oxo-8(7H)-pteridinyl)phenyl)acrylamide (Compound 12)

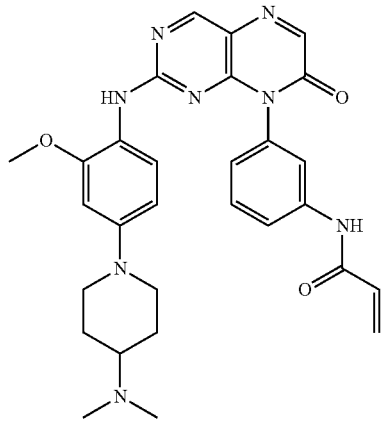 [SMILES: C=CC(=O)Nc1cccc(-n2c(=O)cnc3cnc(Nc4ccc(N5CCC(N(C)C)CC5)cc4OC)nc32)c1]

red solids, yield 50%. ¹H NMR (400 MHz, DMSO-d₆): δ10.41 (s, 1H), 8.80 (s, 1H), 8.43 (s, 1H), 8.03 (s, 1H), 7.88-7.87 (m, 1H), 7.70 (s, 1H), 7.52 (t, J=8.0 Hz, 1H), 7.29 (d, J=8.0 Hz, 1H), 7.09 (d, J=8.0 Hz, 1H), 6.52 (s, 1H), 6.46 (dd, J=17.2, 10.0 Hz, 1H), 6.27 (dd, J=17.2, 2.0 Hz, 1H), 6.04 (br, 1H), 5.78 (dd, J=10.0, 2.0 Hz, 1H), 3.76 (s, 3H), 3.60-3.58 (m, 2H), 2.58 (t, J=10.8 Hz, 2H), 2.20-2.18 (m, 7H), 1.82-1.79 (d, J=12 Hz, 2H), 1.48-1.40 (m, 2H). HRMS (ESI) (m/z): [M+H]⁺ calcd for $C_{29}H_{33}N_8O_3$, 541.2676; found, 541.2674.

N-(3-(6-isopropyl-2-((4-(4-methyl-1-piperazinyl)phenyl)amino)-7-oxo-8(7H)-pteridinyl)phenyl)acrylamide (Compound 13)

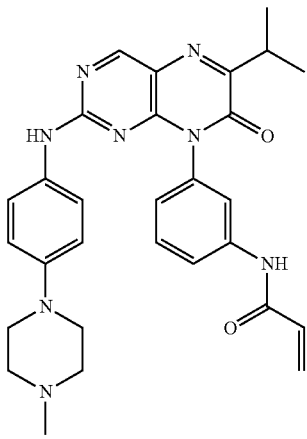 [SMILES: C=CC(=O)Nc1cccc(-n2c(=O)c(C(C)C)nc3cnc(Nc4ccc(N5CCN(C)CC5)cc4)nc32)c1]

Red solids 163 mg, yield 75%. ¹H NMR (400 MHz, DMSO-d₆): δ10.42 (s, 1H), 9.85 (br, 1H), 8.79 (s, 1H), 7.91 (d, J=6.4 Hz, 1H), 7.71 (s, 1H), 7.55 (t, J=8.0 Hz, 1H), 7.25 (s, 2H), 7.11 (d, J=8.0 Hz, 1H), 6.59-6.58 (m, 2H), 6.45 (dd, J=17.0, 10.2 Hz, 1H), 6.26 (dd, J=17.0, 2.0 Hz, 1H), 5.78 (dd, J=10.2, 2.0 Hz, 1H), 3.45-3.38 (m, 1H), 2.97 (br, 4H), 2.42 (br, 4H), 2.21 (s, 3H), 1.25 (d, J=6.8 Hz, 6H). HRMS (ESI) (m/z): [M+H]⁺ calcd for $C_{29}H_{33}N_8O_3$, 525.2726; found, 525.2728.

66

N-(3-(2-((2-methoxy-4-(4-methyl-1-piperazinyl)phenyl)amino)-7-oxo-6-phenyl-8(7H)-pteridinyl)phenyl)acrylamide (Compound 14)

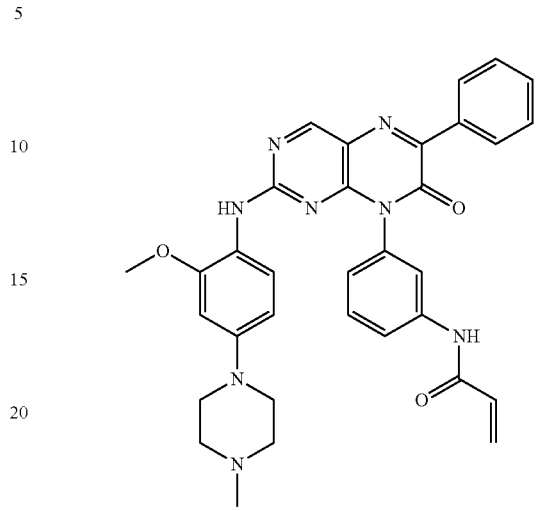

red solids, yield 75%. ¹H NMR (400 MHz, DMSO-d₆): δ10.41 (s, 1H), 8.87 (s, 1H), 8.41 (s, 1H), 8.21-8.19 (m, 2H), 7.89-7.88 (m, 1H), 7.75 (t, J=2.0 Hz, 1H), 7.54 (t, J=8.0 Hz, 1H), 7.50-7.48 (m, 3H), 7.35 (d, J=8.8 Hz, 1H), 7.17-7.14 (m, 1H), 6.54 (d, J=2.0 Hz, 1H), 6.46 (dd, J=17.0, 10.2 Hz, 1H), 6.27 (dd, J=17.0, 2.0 Hz, 1H), 6.05 (br, 1H), 5.78 (dd, J=10.2, 2.0 Hz, 1H), 3.78 (s, 3H), 3.05 (br, 4H), 2.45 (br, 4H), 2.23 (s, 3H). HRMS (ESI) (m/z): [M+H]⁺ calcd for $C_{33}H_{33}N_8O_3$, 589.2676; found, 589.2676.

8-(1-acryloyl-4-piperidinyl)-2-((2-methoxy-4-(4-methyl-1-piperazinyl)phenyl)amino)-7(8H)-pteridinone (Compound 15)

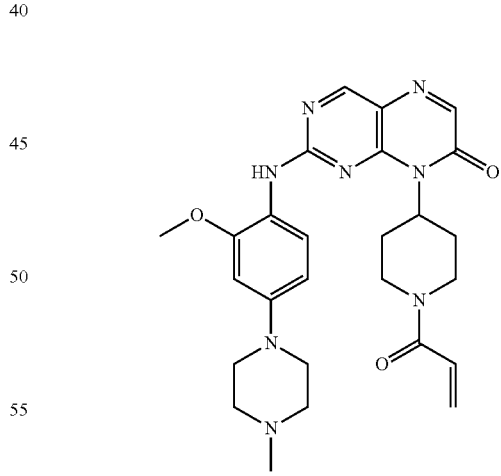

orange solids, yield 53%. ¹H NMR (400 MHz, DMSO-d₆): δ8.83 (s, 1H), 8.71 (s, 1H), 7.83 (s, 1H), 7.53 (br, 1H), 6.85 (dd, J=17.2, 10.4 Hz, 1H), 6.61 (d, J=2.4 Hz, 1H), 6.47 (d, J=8.0 Hz, 1H), 6.13 (dd, J=17.2, 2.4 Hz, 1H), 5.70 (dd, J=10.4, 2.4 Hz, 1H), 5.29 (br, 1H), 4.60 (d, J=10.4 Hz, 1H), 4.20 (d, J=12.8 Hz, 1H), 3.80 (s, 3H), 3.13 (t, J=4.8 Hz, 4H), 2.59-2.53 (m, 3H), 2.45 (t, J=4.8 Hz, 4H), 2.22 (s, 3H), 1.67 (d, J=10.0 Hz, 2H), 1.23 (s, 1H).

67

(R)-8-((1-acryloyl-3-piperidinyl)methyl)-2-((2-methoxy-4-(4-methyl-1-piperazinyl)phenyl)amino)-7(8H)-pteridinone (Compound 16)

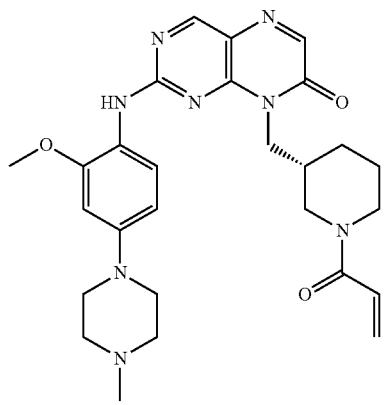 [SMILES: C=CC(=O)N1CCC[C@@H](Cn2c(=O)cnc3cnc(Nc4ccc(N5CCN(C)CC5)cc4OC)nc32)C1]

orange solids, yield 61%. $^1$H NMR (400 MHz, DMSO-$d_6$): δ8.92 (s, 1H), 8.74 (s, 1H), 7.91-7.89 (m, 1H), 7.50-7.44 (m, 1H), 6.75 (dd, J=16.8, 10.4 Hz, 1H), 6.64 (s, 1H), 6.56-6.51 (m, 1H), 6.02 (d, J=16.8 Hz, 1H), 5.64-5.54 (m, 1H), 4.13-4.10 (m, 1H), 3.94-3.83 (m, 3H), 3.76 (s, 3H), 3.16 (br, 4H), 3.03-2.98 (m, 1H), 2.84-2.74 (m, 1H), 2.47 (t, J=4.8 Hz, 4H), 1.92-1.91 (m, 1H), 1.64-1.57 (m, 2H), 1.30-1.23 (m, 3H).

(S)-8-(1-acryloyl-3-piperidinyl)methyl)-2-((2-methoxy-4-(4-methyl-1-piperazinyl)phenyl)amino)-7(8H)-pteridinone (Compound 17)

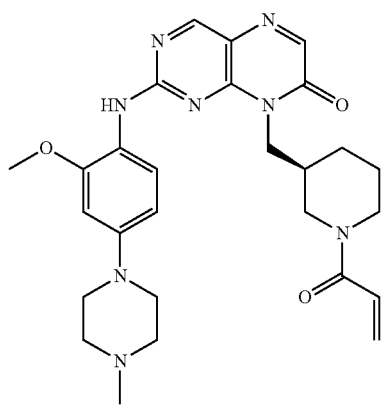 [SMILES: C=CC(=O)N1CCC[C@H](Cn2c(=O)cnc3cnc(Nc4ccc(N5CCN(C)CC5)cc4OC)nc32)C1]

orange solids, yield 54%. $^1$H NMR (400 MHz, DMSO-$d_6$): δ8.92 (s, 1H), 8.74 (s, 1H), 7.91-7.89 (m, 1H), 7.49-7.43 (m, 1H), 6.75 (dd, J=16.4, 10.4 Hz, 1H), 6.64 (s, 1H), 6.56-6.51 (m, 1H), 6.02 (d, J=16.4 Hz, 1H), 5.64-5.54 (m, 1H), 4.13-4.08 (m, 1H), 3.94-3.86 (m, 3H), 3.76 (s, 3H), 3.16 (br, 4H), 3.03-2.97 (m, 1H), 2.84-2.74 (m, 1H), 2.47 (t, J=4.8 Hz, 4H), 1.92 (br, 1H), 1.64-1.57 (m, 2H), 1.30-1.20 (m, 3H).

68

N-(3-(2-((4-((2-(dimethylamino)ethyl)(methyl)amino)-2-methoxyphenyl)amino)-7-oxo-8(7H)-pteridinyl)phenyl)acrylamide (Compound 18)

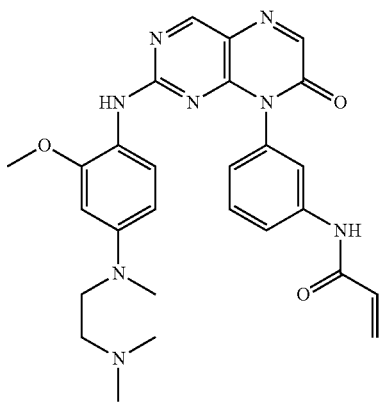 [SMILES: C=CC(=O)Nc1cccc(-n2c(=O)cnc3cnc(Nc4ccc(N(C)CCN(C)C)cc4OC)nc32)c1]

red solids, yield 61%. $^1$H NMR (400 MHz, DMSO-$d_6$): δ10.37 (s, 1H), 8.76 (s, 1H), 8.41 (br, 1H), 7.99 (s, 1H), 7.84-7.83 (m, 1H), 7.69 (t, J=2.0 Hz, 1H), 7.51 (t, J=8.0 Hz, 1H), 7.26-7.19 (m, 1H), 7.09 (d, J=8.0 Hz, 1H), 6.45 (dd, J=16.8, 10.4 Hz, 1H), 6.29-6.24 (m, 2H), 5.77 (dd, J=10.4, 2.0 Hz, 1H), 3.74 (s, 3H), 2.84 (s, 3H), 2.35-2.33 (m, 2H), 2.19 (s, 6H).

N-(3-(2-((4-((2-(dimethylamino)ethyl)(methyl)amino)-2-methoxyphenyl)amino)-6-isopropyl-7-oxo-8(7H)-pteridinyl)phenyl)acrylamide (Compound 19)

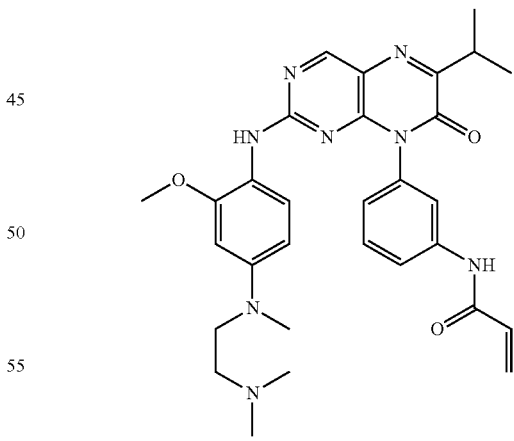

orange solids, yield 62%. $^1$H NMR (400 MHz, DMSO-$d_6$): δ10.37 (s, 1H), 8.72 (s, 1H), 8.21 (s, 1H), 7.84 (d, J=8.0 Hz, 1H), 7.69 (s, 1H), 7.51 (t, J=8.0 Hz, 1H), 7.26 (d, J=7.6 Hz, 1H), 7.09 (d, J=8.4 Hz, 1H), 6.45 (dd, J=16.8, 10.4 Hz, 1H), 6.29-6.24 (m, 2H), 5.87 (br, 1H), 5.76 (dd, J=10.4, 2.0 Hz, 1H), 3.75 (s, 3H), 3.43-3.38 (m, 1H), 2.84 (s, 3H), 2.34 (t, J=6.8 Hz, 2H), 2.19 (s, 6H), 1.24 (d, J=6.8 Hz, 6H).

N-(3-(2-((4-((2-(dimethylamino)ethyl)(methyl) amino)-2-methoxyphenyl)amino)-7-oxo-6-phenyl-8 (7H)-pteridinyl)phenyl)acrylamide (Compound 20)

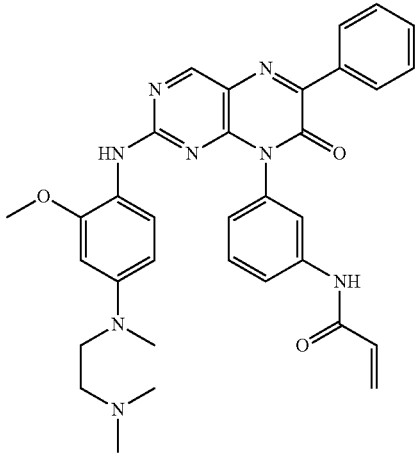 [SMILES: C=CC(=O)Nc1cccc(-n2c(=O)c(-c3ccccc3)nc3cnc(Nc4ccc(N(C)CCN(C)C)cc4OC)nc32)c1]

red solids, yield 64%. ¹H NMR (400 MHz, DMSO-d₆): δ10.39 (s, 1H), 8.83 (s, 1H), 8.38 (br, 1H), 8.21-8.18 (m, 2H), 7.87 (d, J=7.2 Hz, 1H), 7.75 (s, 1H), 7.53 (t, J=8.0 Hz, 1H), 7.49-7.47 (m, 3H), 7.28 (br, 1H), 7.15 (d, J=8.4 Hz, 1H), 6.46 (dd, J=16.8, 10.0 Hz, 1H), 6.29-6.25 (m, 2H), 5.83 (br, 1H), 5.76 (dd, J=10.0, 2.0 Hz, 1H), 3.76 (s, 3H), 3.35 (br, 2H), 2.85 (s, 3H), 2.35 (t, J=5.6 Hz, 2H), 2.20 (s, 6H).

(R)-8-((1-acryloyl-3-piperidinyl)methyl)-6-isopropyl-2-((2-methoxy-4-(4-methyl-1-piperazinyl)phenyl)amino)-7(8H)-pteridinone (Compound 21)

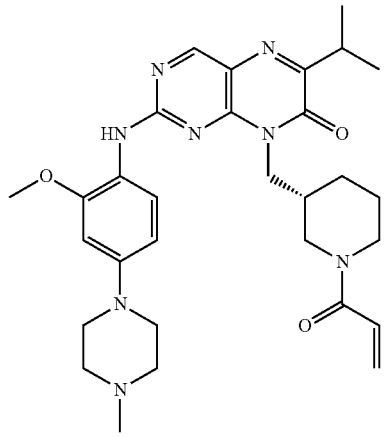 [SMILES: C=CC(=O)N1CCC[C@@H](Cn2c(=O)c(C(C)C)nc3cnc(Nc4ccc(N5CCN(C)CC5)cc4OC)nc32)C1]

yellow solids, yield 55%. ¹H NMR (400 MHz, DMSO-d₆): δ8.70 (br, 2H), 7.57-7.52 (m, 1H), 6.76 (dd, J=16.4, 10.4 Hz, 1H), 6.64 (s, 1H), 6.57-6.51 (m, 1H), 6.05-5.98 (m, 1H), 5.64-5.53 (m, 1H), 4.15-3.96 (m, 3H), 3.90-3.87 (m, 1H), 3.78 (s, 3H), 3.16 (br, 4H), 3.04-2.75 (m, 2H), 2.47 (t, J=3.6 Hz, 4H), 2.24 (s, 3H), 1.94 (br, 1H), 1.66-1.61 (m, 2H), 1.20 (d, J=6.8 Hz, 6H).

(R)-8-(1-acryloyl-3-piperidinyl)-2-((2-methoxy)-4-(4-methyl-1-piperazinyl)phenyl)amino)-7(8H)pteridinone (Compound 22)

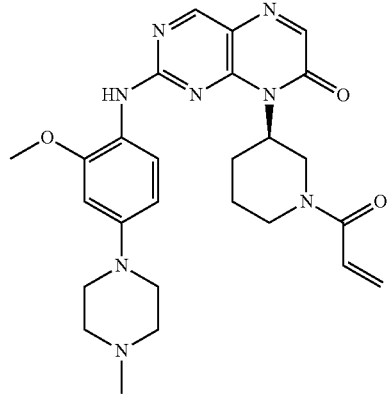 [SMILES: C=CC(=O)N1CCC[C@@H](n2c(=O)cnc3cnc(Nc4ccc(N5CCN(C)CC5)cc4OC)nc32)C1]

orange solids, yield 46%. ¹H NMR (400 MHz, DMSO-d₆): δ9.17 (s, 1H), 8.71 (s, 1H), 7.83 (s, 1H), 7.20 (br, 1H), 6.81 (br, 1H), 6.68-6.62 (m, 2H), 6.47 (br, 1H), 6.14-6.08 (m, 1H), 5.72-5.61 (m, 1H), 4.78-4.72 (m, 1H), 4.35-4.24 (m, 1H), 3.95-3.82 (m, 1H), 3.73 (s, 3H), 3.14 (br, 4H), 2.46 (br, 4H), 2.23 (s, 3H), 1.62 (br, 2H), 1.34-1.26 (m, 1H).

N-(2-((2-(dimethylamino)ethyl)(methyl)amino)-5-((6-isopropyl-8-methyl)-7-oxo-7,8-dihydrogen-2-pteridinyl)amino)-4-methoxyphenyl)acrylamide (Compound 23)

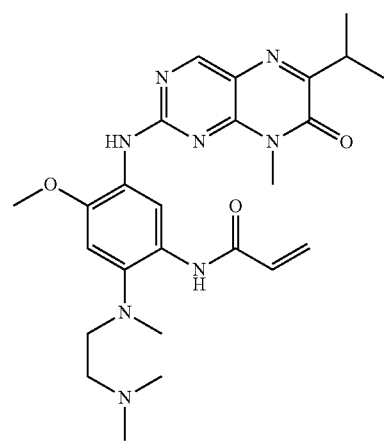 [SMILES: C=CC(=O)Nc1cc(Nc2ncc3nc(C(C)C)c(=O)n(C)c3n2)c(OC)cc1N(C)CCN(C)C]

yellow solids, yield 43%. ¹H NMR (400 MHz, DMSO-d₆): δ10.08 (s, 1H), 8.96 (s, 1H), 8.73 (s, 1H), 8.64 (s, 1H), 7.02 (s, 1H), 6.42 (dd, J=16.4, 10.0 Hz, 1H), 6.24 (d, J=16.4 Hz, 1H), 5.75 (d, J=10.4 Hz, 1H), 3.85 (s, 3H), 3.59 (s, 3H), 3.43-3.36 (m, 1H), 2.89 (br, 2H), 2.71 (s, 3H), 2.35 (br, 2H), 2.23 (s, 6H), 1.20 (d, J=6.8 Hz, 6H).

71

(S)-8-(1-acryloyl-3-pyrrolidinyl)-6-isopropyl-2-((3-methyl-4-(4-methyl-1-piperazinyl)phenyl)amino)-7(8H)-pteridinone (Compound 24)

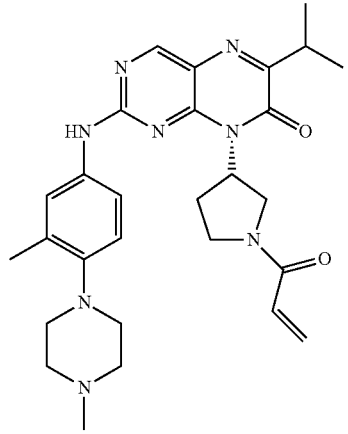

yellow solids, yield 81%. $^1$H NMR (400 MHz, DMSO-$d_6$): δ9.90 (s, 1H), 8.77 (s, 0.6H), 8.76 (s, 0.4H), 7.49-7.41 (m, 2H), 6.93 (t, J=7.2 Hz, 1H), 6.73-6.47 (m, 1H), 6.23-6.15 (m, 1H), 6.03-5.94 (m, 1H), 5.76-5.65 (m, 1H), 4.22 (t, J=8.8 Hz, 0.6H), 4.02-3.86 (m, 1.7H), 3.83-3.65 (m, 1.7H), 3.47-3.40 (m, 1H), 2.92-2.85 (m, 1H), 2.78 (br, 4H), 2.46 (br, 4H), 2.23 (s, 3H), 2.20 (s, 3H), 2.14-2.07 (m, 1H), 1.20 (d, J=6.4 Hz, 6H). HRMS (ESI) (m/z): [M+H]$^+$ calcd for $C_{28}H_{37}N_8O_2$ [M+H]$^+$ 517.3039; found, 517.3038.

(S)-8-(1-acryloyl-3-pyrrolidinyl)-2-((3-methyl-4-(4-methyl-1-piperazinyl)phenyl) amino)-6-phenyl-7(8H)-pteridinone (Compound 25)

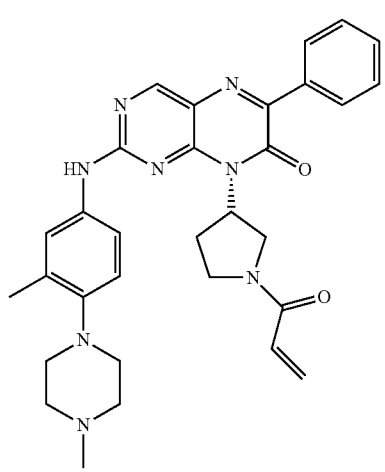

orange solids, yield 77%. $^1$H NMR (400 MHz, DMSO-$d_6$): δ10.09 (s, 1H), 8.88 (s, 1H), 8.13 (br, 2H), 7.52-7.49 (m, 5H), 6.98-6.96 (m, 1H), 6.74-6.48 (m, 1H), 6.23-6.15 (m, 1H), 6.13-6.02 (m, 1H), 5.73-5.65 (m, 1H), 4.28-4.24 (m, 0.5H), 4.12-3.90 (m, 1.7H), 3.85-3.67 (m, 1.8H), 3.52-3.44 (m, 1H), 2.94-2.89 (m, 1H), 2.82 (br, 4H), 2.28 (s, 3H), 2.22 (s, 3H). HRMS (ESI) (m/z): [M+H]$^+$ calcd for $C_{31}H_{35}N_8O_2$ [M+H]$^+$ 551.2883; found, 551.2880.

72

(S)-8-(1-acryloyl-3-pyrrolidinyl)-6-isopropyl-2-((2-methoxy-4-(4-methyl-1-piperazinyl)phenyl)amino)-7(8H)-pteridinone (Compound 26)

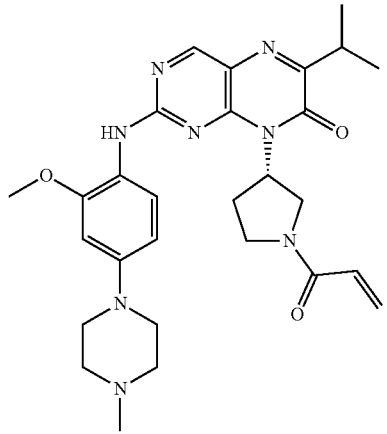 [SMILES: C=CC(=O)N1CC[C@H](n2c(=O)c(C(C)C)nc3cnc(Nc4ccc(N5CCN(C)CC5)cc4OC)nc32)C1]

orange solids, yield 54%. $^1$H NMR (400 MHz, DMSO-$d_6$): δ8.71 (s, 1H), 8.69 (s, 0.5H), 8.68 (s, 0.5H), 7.39 (t, J=7.6 Hz, 1H), 6.57 (s, 1H), 6.41 (d, J=8.8 Hz, 1H), 6.17 (dd, J=16.4 Hz, 10.8 Hz, 1H), 5.86-5.80 (m, 1H), 5.72-5.63 (m, 1H), 4.12 (t, J=8.8 Hz, 0.6H), 3.91-3.86 (m, 0.6H), 3.77 (s, 3H), 3.69-3.64 (m, 1H), 3.59 (br, 1H), 3.40-3.38 (m, 0.8H), 3.12 (br, 4H), 2.81-2.70 (m, 1H), 2.45 (br, 4H), 2.23 (s, 3H), 2.09-1.98 (m, 1H), 1.18 (d, J=6.4 Hz, 6H). HRMS (ESI) (m/z): [M+H]$^+$ calcd for 533.2989; found, 533.2994.

(S)-8-(1-acryloyl-3-pyrrolidinyl)-2-((2-methoxy-4-(4-methyl-1-piperazinyl)phenyl)amino)-6-phenyl-7(8H)-pteridinone (Compound 27)

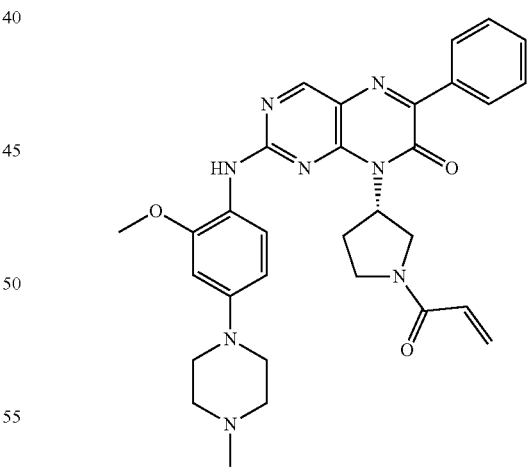

red solids, yield 63%. $^1$H NMR (400 MHz, DMSO-$d_6$): δ8.90 (s, 1H), 8.79 (s, 1H), 8.10 (br, 2H), 7.46 (br, 3H), 7.41-3.39 (m, 1H), 6.58-6.42 (m, 3H), 6.17 (dd, J=16.4 Hz, 10.4 Hz, 1H), 5.98-5.82 (m, 1H), 5.72-5.64 (m, 1H), 4.16 (t, J=8.8 Hz, 0.6H), 3.95-3.90 (m, 0.6H), 3.78 (s, 3H), 3.71 (t, J=9.6 Hz, 0.8H), 3.60 (br, 1H), 3.40-3.34 (m, 1H), 3.13 (br, 4H), 2.83-2.71 (m, 1H), 2.45 (br, 4H), 2.23 (s, 3H), 2.12-2.02 (m, 1H). HRMS (ESI) (m/z): [M+H]$^+$ calcd for $C_{31}H_{35}N_8O_3$ [M+H]$^+$ 567.2832; found, 567.2831.

(S,E)-8-(1-(4-(dimethylamino)-2-butenoyl)-3-pyrrolidinyl)-6-isopropyl-2-((3-methyl-4-(4-methyl-1-piperazinyl)phenyl)amino)-7(8H)-pteridinone (Compound 28)

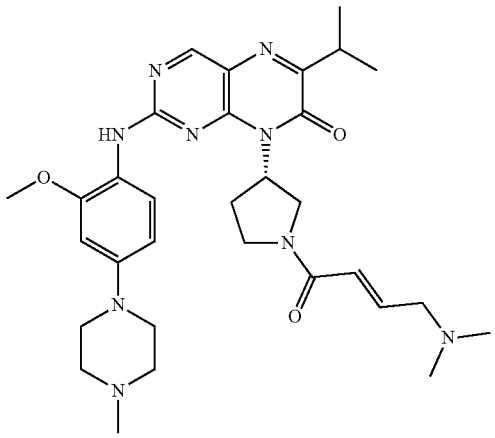

orange solids, yield 89%. ¹H NMR (400 MHz, CDCl₃) δ8.75 (s, 1H), 8.00 (s, 1H), 7.73 (s, 0.6H), 7.65 (s, 0.4H), 7.02-6.89 (m, 1H), 6.55-6.50 (m, 2H), 6.42-6.20 (m, 1H), 6.17-6.07 (m, 1H), 4.48-4.45 (m, 0.5H), 4.18-3.99 (m, 2H), 3.90 (s, 3H), 3.83 (t, J=8.8 Hz, 0.8H), 3.76-3.69 (m, 0.6H), 3.65-3.56 (m, 0.7H), 3.52-3.44 (m, 1H), 3.22-3.18 (m, 4H), 3.15 (t, J=6.0 Hz, 1H), 3.04 (d, J=5.6 Hz, 2H), 2.62-2.60 (br, 4H), 2.38 (s, 3H), 2.30 (s, 3H), 2.21 (s, 3H), 2.14-2.10 (m, 1H), 1.99 (s, 2H), 1.26 (t, J=6.0 Hz, 6H).

(S,E)-8-(1-(4-(dimethylamino)-2-butenoyl)-3-pyrrolidinyl)-2-((3-methyl-4-(4-methyl-1-piperazinyl)phenyl)amino)-6-phenyl-7(8H)-pteridinone (Compound 29)

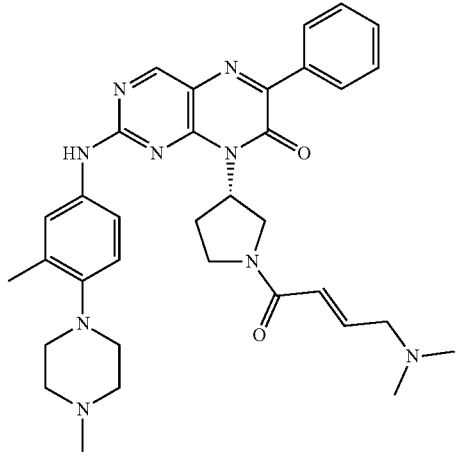

orange solids, yield 82%. ¹H NMR (400 MHz, DMSO-d₆): δ10.10 (s, 1H), 8.88 (s, 1H), 8.12 (s, 2H), 7.49 (br, 5H), 6.97 (d, J=8.4 Hz, 1H), 6.72-6.61 (m, 1H), 6.54-6.31 (m, 1H), 6.10-6.00 (m, 1H), 4.28-4.24 (m, 0.6H), 4.05-4.00 (m, 0.7H), 3.93-3.86 (m, 1.5H), 3.81-3.76 (m, 1.5H), 3.73-3.67 (m, 1H), 3.55 (br, 4H), 3.18 (d, J=6.8 Hz, 2H), 3.08 (d, J=5.2 Hz, 1H), 2.83 (br, 4H), 2.57 (s, 3H), 2.32 (s, 1.5H), 2.30 (s, 1.5H), 2.57 (s, 3H), 2.22 (s, 3H), 2.17 (s, 3H). HRMS (ESI) (m/z): [M+H]⁺ calcd for C₃₄H₄₂N₉O₂ [M+H]⁺ 608.3461; found, 608.3466.

(E)-8-(1-(4-(dimethylamino)-2-butenoyl)-4-piperidinyl)-2-((2-methoxy-4-(4-methyl-1-piperazinyl)phenyl)amino)-7(8H)pteridinone (Compound 30)

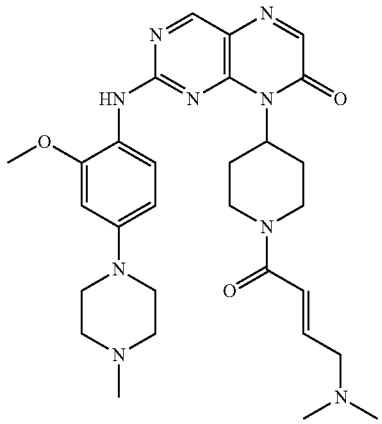

红色固体 (yield 71%). mp 157.3-157.6° C. ¹H NMR (400 MHz, DMSO-d₆): δ 8.86 (s, 1H), 8.72 (s, 1H), 7.83 (s, 1H), 7.54 (br, 1H), 6.64-6.62 (m, 3H), 6.47 (d, J=7.6 Hz, 1H), 5.27 (br, 1H), 4.61-4.58 (m, 1H), 4.21-4.18 (m, 1H), 3.79 (s, 3H), 3.14 (br, 4H), 3.05-3.04 (br, 2H), 2.57 (br, 4H), 2.46 (t, J=4.0 Hz, 4H), 2.23 (s, 3H), 2.16 (s, 6H), 1.67 (br, 2H). HRMS (ESI) (m/z): [M+H]⁺ calcd for C₂₉H₄₀N₉O₃, 562.3254; found, 562.3259.

(S,E)-8-(1-(4-(dimethylamino)-2-butenoyl)3-pyrrolidinyl)-2-((2-methoxy-4-(4-methyl-1-piperazinyl)phenyl)amino-6-phenyl-7(8H)pteridinone (Compound 31)

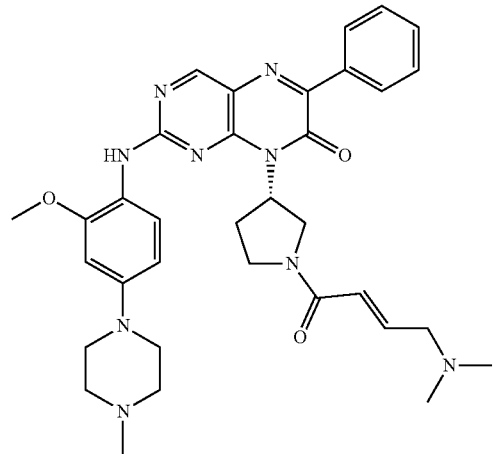

orange solids, yield 89%. mp 253.1-254.0° C. ¹H NMR (400 MHz, DMSO-d₆): δ9.92 (d, J=6.8 Hz, 1H), 8.80 (d, J=3.2 Hz, 1H), 8.12-8.11 (m, 2H), 7.31-7.67 (m, 1H), 7.47 (m, 3H), 7.42 (t, J=8.0 Hz, 1H), 7.71-6.62 (m, 1H), 6.59 (br, 1H), 6.46-6.42 (m, 1H), 4.19-4.10 (m, 2H), 3.94-3.89 (m, 1H), 3.71 (t, J=10.8 Hz, 1H), 4.60-3.59 (m, 1H), 3.79 (s, 3H), 3.14 (br, 4H), 3.09-3.03 (m, 1H), 3.00 (d, J=5.6, 1H), 2.87-2.74 (m, 1H), 2.47 (br, 4H), 2.24 (s, 3H), 2.19 (s, 3H), 2.13 (s, 3H). HPLC purity: 98.1%, Retention time=9.63 min. HRMS (ESI) (m/z): [M+H]⁺ calcd for C₃₄H₄₂N₉O₃ [M+H]⁺ 624.3411; found, 624.3413.

N-(3-(6-isopropyl-2-((3-methoxy-4-(4-methyl-1-piperazinyl)phenyl)amino)-7-oxo-8(7H)pteridinyl)phenyl)acrylamide (Compound 32)

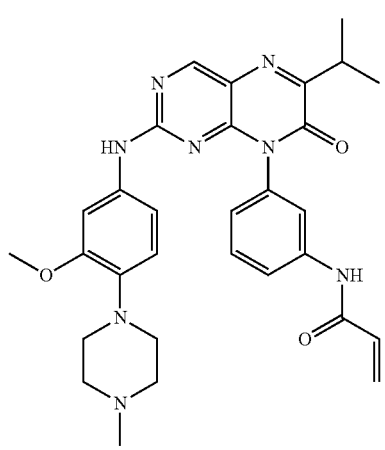 [SMILES: C=CC(=O)Nc1cccc(-n2c(=O)c(C(C)C)nc3cnc(Nc4ccc(N5CCN(C)CC5)c(OC)c4)nc32)c1]

黄色固体 (yield 69%). mp 249.0-249.5° C. ¹H NMR (400 MHz, DMSO-d₆): δ 10.42 (s, 1H), 9.83 (br, 1H), 8.82 (s, 1H), 7.87 (d, J=8.0 Hz, 1H), 7.73 (s, 1H), 7.53 (t, J=8.0 Hz, 1H), 7.12 (d, J=8.0 Hz, 1H), 7.04 (br, 1H), 6.96 (br, 1H), 6.49-6.42 (m, 2H), 6.26 (dd, J=16.8 Hz, 2.0 Hz, 1H), 5.77 (dd, J=10.0 Hz, 2.0 Hz, 1H), 3.55 (s, 3H), 3.44-3.39 (m, 1H), 2.82 (br, 4H), 2.42 (br, 4H), 2.21 (s, 3H), 1.25 (d, J=6.8 Hz, 6H). HRMS (ESI) (m/z): [M+H]⁺ calcd for C₃₀H₃₅N₈O₃, 555.2832; found, 555.2838.

N-(3-(2-((3-methoxy-4-(4-methyl-1-piperazinyl)phenyl)amino)-7-oxo-6-(trifluoromethyl)-8(7H)-pteridinyl)phenyl)acrylamide (Compound 33)

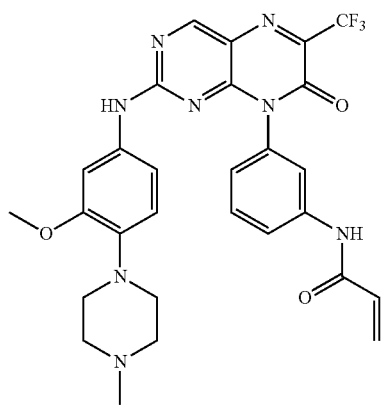 [SMILES: C=CC(=O)Nc1cccc(-n2c(=O)c(C(F)(F)F)nc3cnc(Nc4ccc(N5CCN(C)CC5)c(OC)c4)nc32)c1]

Brown solids (yield 59%). mp >300° C. ¹H NMR (400 MHz, DMSO-d₆): δ10.44 (s, 1H), 10.40 (s, 1H), 9.00 (s, 1H), 7.88 (d, J=7.2 Hz, 1H), 7.81 (s, 1H), 7.56 (t, J=8.0 Hz, 1H), 7.14 (d, J=8.0 Hz, 1H), 7.01 (d, J=7.2 Hz, 1H), 6.95 (s, 1H), 6.49-6.42 (m, 2H), 6.27 (d, J=16.4 Hz, 1H), 5.77 (d, J=10.4 Hz, 1H), 3.53 (s, 3H), 2.83 (br, 4H), 2.41 (br, 4H), 2.21 (s, 3H). HRMS (ESI) (m/z): [M+H]⁺ calcd for C₂₈H₂₈N₈O₃F₃, 581.2236; found, 581.2241.

(S)-8-(1-acryloyl-3-pyrrolidinyl)-2-((3-methyl-4-(4-methyl-1-piperazinyl)phenyl) amino)-7(8H)pteridinone (Compound 34)

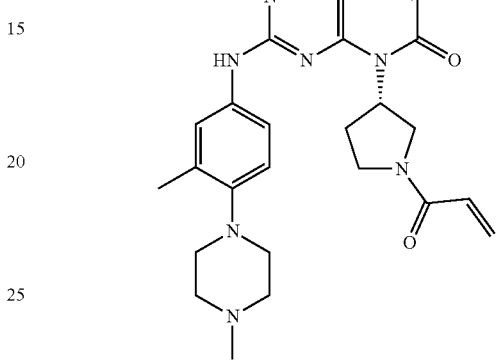

Yellow solids (yield 45%). mp 215.5-215.7° C. ¹H NMR (400 MHz, DMSO-d₆): δ10.08 (s, 1H), 8.81 (d, J=3.2 Hz, 1H), 7.89 (d, J=6.8 Hz, 1H), 7.47-7.42 (m, 2H), 6.93 (t, J=6.8 Hz, 1H), 6.72-6.46 (m, 1H), 6.22-6.6.14 (m, 1H), 5.98-5.88 (m, 1H), 5.75-5.64 (m, 1H), 4.20 (t, J=8.8, 1H), 4.00-3.64 (m, 4H), 3.47-3.40 (m, 1H), 2.78 (br, 4H), 2.45 (s, 3H), 2.23 (s, 3H), 2.20 (br, 4H). HRMS (ESI) (m/z): [M+H]⁺ calcd for C₂₅H₃₁N₈O₂, 475.2570; found, 475.2550.

(S)-8-(1-acryloyl-30pyrrolidinyl)-2-((3-methoxy-4 (4-methyl-1-piperazinyl)phenyl)amino)-6-phenyl-7 (8H)pteridinone (Compound 35)

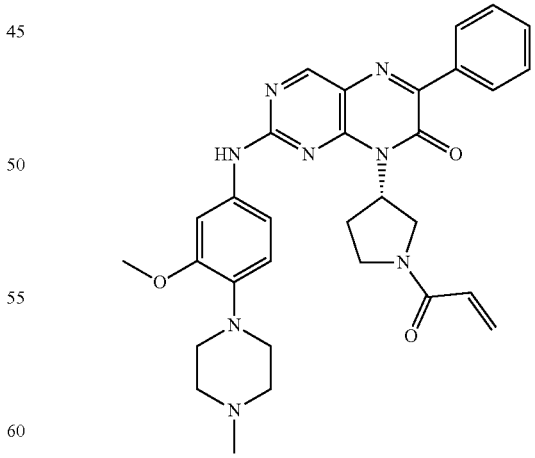

Orange solids (yield 40%). mp 208.3-208.8° C. ¹H NMR (400 MHz, DMSO-d₆): δ 10.10 (s, 1H), 8.88 (d, J=3.2, 1H), 8.13-8.12 (m, 2H), 7.48 (d, J=2.4 Hz, 1H), 7.47 (s, 1H), 7.34-7.27 (m, 2H), 6.81 (t, J=8.4 Hz, 1H), 6.74-6.48 (m, 1H), 6.23-6.15 (m, 1H), 6.12-6.04 (m, 1H), 5.76-5.65 (m, 1H), 4.25 (t, J=9.2, 1H), 4.13-3.76 (m, 3H), 3.76 (s, 3H), 3.74-3.67 (m, 1H), 3.51-3.44 (m, 1H), 2.91 (br, 4H), 2.44 (br, 4H), 2.21 (s, 3H). HRMS (ESI) (m/z): [M+H]$^+$ calcd for $C_{31}H_{35}N_8O_3$, 567.2832; found, 567.2835.

(S,E)-8-(1-(4-(dimethylamino)-2-butenoyl)3-pyrrolidinyl)-2-((3-methyl-4-(4-methyl-1-piperazinyl)phenyl)amino)-6-isopropyl-7(8H)pteridinone (Compound 36)

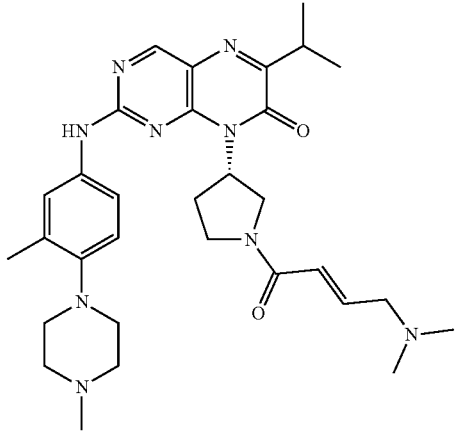

Red solids (yield 62%). mp 159.9-160.7° C. $^1$H NMR (400 MHz, DMSO-d$_6$): δ9.94 (s, 1H), 8.77 (d, J=3.6 Hz, 1H), 7.49-7.40 (m, 2H), 6.94 (d, J=8.4, 1H), 6.72-6.61 (m, 1H), 6.53 (d, J=15.2 Hz, 0.5H), 6.34 (d, J=15.2 Hz, 0.5H), 6.04-5.91 (m, 1H), 4.22 (t, J=8.4 Hz, 1H), 4.00-3.64 (m, 4H), 3.40-3.35 (m, 2H), 3.22 (t, J=6.4 Hz, 1H), 3.10 (d, J=6.0 Hz, 1H), 2.82 (br, 4H), 2.61 (br, 4H), 2.34 (d, 11.2 Hz, 3H), 2.28 (s, 3H), 2.20 (br, 4H), 2.19 (s, 3H), 1.20 (d, J=6.8 Hz, 6H). HRMS (ESI) (m/z): [M+H]$^+$ calcd for $C_{31}H_{44}N_9O_2$, 574.3618; found, 574.3584.

N-(3-(6-isopropyl-2-((2-methoxy-4-(4-methyl-1-piperazinyl)phenyl)amino)-7-oxo-8(7H)pteridinyl)phenyl)acrylamide (Compound 37)

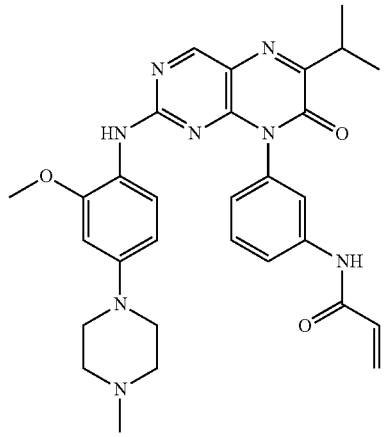 [SMILES: C=CC(=O)Nc1cccc(-n2c(=O)c(C(C)C)nc3cnc(Nc4ccc(N5CCN(C)CC5)cc4OC)nc32)c1]

Orange solids (yield 65%). mp 242.9-243.9° C. $^1$H NMR (400 MHz, DMSO-d$_6$): δ10.42 (s, 1H), 8.75 (s, 1H), 8.26 (s, 1H), 7.87 (d, J=7.2 Hz, 1H), 7.71 (s, 1H), 7.53 (t, J=8.0 Hz, 1H), 7.34 (d, J=8.8 Hz, 1H), 7.10 (d, J=8.8 Hz, 1H), 6.53 (d, J=2.0 Hz, 1H), 6.46 (dd, J=16.8 Hz, 10.0 Hz, 1H), 6.27 (dd, J=16.8 Hz, 2.0 Hz, 1H), 6.12-6.00 (m, 1H), 5.78 (dd, J=10.0 Hz, 2.0 Hz), 3.76 (s, 3H), 3.44-3.41 (m, 1H), 3.04 (br, 4H), 2.43 (t, J=4.8 Hz, 4H), 2.22 (s, 3H), 1.25 (d, J=6.8 Hz, 6H). HRMS (ESI) (m/z): [M+H]$^+$ calcd for $C_{30}H_{35}N_8O_3$, 555.2832; found, 555.2821.

N-(3-(2-((2-methoxy-5-methyl-4-(4-methyl-1-piperazinyl)phenyl)amino)-7-oxo-6-phenyl-8(7H)pteridinonyl)phenyl)acrylamide (Compound 38)

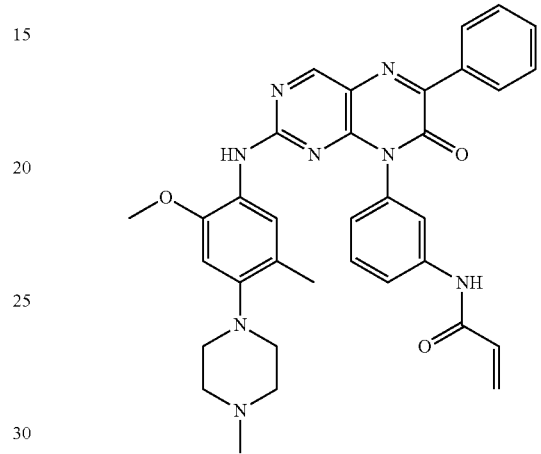

Yellow solids (yield 62%). mp 292.9-293.4° C. $^1$H NMR (400 MHz, DMSO-d$_6$): δ10.41 (s, 1H), 8.90 (s, 1H), 8.36 (br, 1H), 8.21-8.18 (m, 2H), 7.84 (d, J=8.0 Hz, 1H), 7.80 (s, 1H), 7.55 (t, J=8.0 Hz, 1H), 7.50-7.48 (m, 3H), 7.33 (s, 1H), 7.16 (d, J=7.6 Hz, 1H), 6.63 (s, 1H), 6.45 (dd, J=16.8 Hz, 10.0 Hz, 1H), 6.26 (dd, J=16.8 Hz, 1.6 Hz), 5.77 (dd, J=10.0 Hz, 1.6 Hz, 1H), 3.79 (s, 3H), 2.77 (br, 4H), 2.48 (br, 4H), 2.25 (s, 3H), 1.85 (br, 3H). HRMS (ESI) (m/z): [M+H]$^+$ calcd for $C_{34}H_{35}N_8O_3$, 603.2832; found, 603.2834.

N-(3-(6-isopropyl-2-((2-methoxy-5-methyl-4-(4-methyl-1-piperazinyl)phenyl)amino)-7-oxo-8(7H)pteridinyl)phenyl)acrylamide (Compound 39)

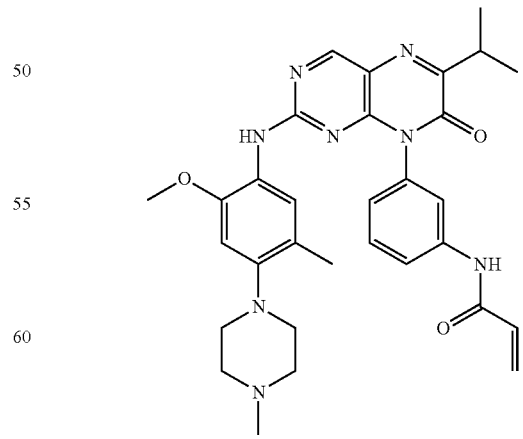

orange solids (yield 60%). mp 227.5-228.5° C. $^1$H NMR (400 MHz, DMSO-d$_6$): δ10.40 (s, 1H), 8.79 (s, 1H), 8.22 (s, 1H), 7.82 (d, J=8.0 Hz, 1H), 7.73 (s, 1H), 7.53 (t, J=8.0 Hz, 1H), 7.31 (s, 1H), 7.11 (d, J=7.6 Hz, 1H), 6.62 (s, 1H), 6.44 (dd, J=16.8 Hz, 10.0 Hz, 1H). 6.25 (dd, J=16.8 Hz, 0.8 Hz, 1H), 5.75 (d, J=10.0 Hz, 1H), 3.78 (s, 3H), 3.43-3.39 (m, 1H), 2.77 (br, 4H), 2.26 (s, 3H), 1.85 (br, 3H), 1.24 (d, J=6.8 Hz, 6H). HRMS (ESI) (m/z): [M+H]+ calcd for C31H37N8O3, 569.2989; found, 569.2989.

(S)-8-(1-acryloyl-3-pyrrolidinyl)-2-((4-(2-(dimethyl-amino)ethyl)(methyl)amino)-3-methylphenyl)amino)-6-phenyl-7(8H)pteridinone (Compound 40)

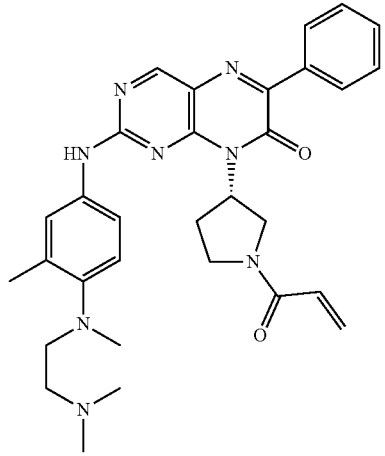 [SMILES: C=CC(=O)N1CC[C@H](n2c(=O)c(-c3ccccc3)nc3cnc(Nc4ccc(N(C)CCN(C)C)c(C)c4)nc32)C1]

red solids (yield 40%). mp 256.1-256.4° C. 1H NMR (400 MHz, DMSO-d6): δ10.08 (s, 1H), 8.88 (d, J=3.2 Hz, 1H), 8.13-8.12 (m, 2H), 7.52-7.45 (m, 5H), 7.02 (dd, J=8.4 Hz, 5.6 Hz, 1H), 6.74-6.49 (m, 1H), 6.23-6.15 (m, 1H), 6.12-6.02 (m, 1H), 5.75-5.65 (m, 1H), 4.28-4.23 (m, 1H), 4.15-4.12 (m, 1H), 3.94-3.68 (m, 3H), 3.52-3.44 (m, 1H), 2.90 (t, J=6.8 Hz, 2H), 2.61 (s, 3H), 2.35 (t, J=6.8 Hz, 2H), 2.22 (s, 3H), 2.13 (br, 6H). HRMS (ESI) (m/z): [M+H]+ calcd for C31H37N8O2, 553.3039; found, 553.3031.

(S)-8-(1-acryloyl-3-pyrrolidinyl)-2-((4-(2-(dimethyl-amino)ethyl)(methyl)amino)-3-methoxyphenyl)amino)-6-phenyl-7(8H)pteridinone (Compound 41)

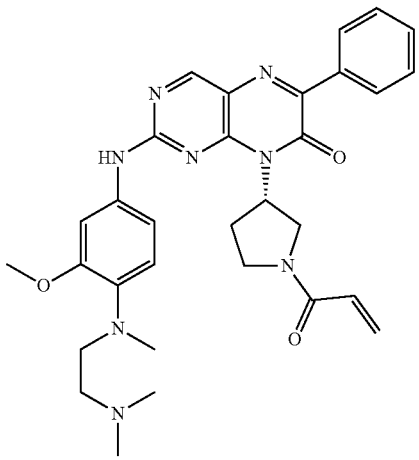 [SMILES: C=CC(=O)N1CC[C@H](n2c(=O)c(-c3ccccc3)nc3cnc(Nc4ccc(N(C)CCN(C)C)c(OC)c4)nc32)C1]

Dark red solids (yield 49%). mp 260.0-260.2° C. 1H NMR (400 MHz, DMSO-d6): δ10.09 (s, 1H), 8.88 (d, J=2.8 Hz, 1H), 8.131 (br, 2H), 7.49-7.48 (m, 3H), 7.34-7.25 (m, 2H), 6.81 (t, J=7.2 Hz, 1H), 6.76-6.49 (m, 1H), 6.23-6.05 (m, 2H), 5.75-5.65 (m, 1H), 4.25 (t, J=8.4 Hz, 1H). 4.06-3.82 (m, 3H), 3.77 (s, 3H), 3.74-3.67 (m, 1H), 3.05 (t, J=7.2 Hz, 2H), 2.94-2.79 (m, 1H), 2.68 (s, 3H), 2.36 (t, J=7.2 Hz, 2H), 2.13 (s, 6H). HRMS (ESI) (m/z): [M+H]+ calcd for C31H37N8O3, 569.2989; found, 569.2988.

N-(3-(2-((3-methoxy-4-(4-methyl-1-piperazinyl)phenyl)amino)-7-oxo-6-phenyl-8(7H)pteridinyl)phenyl)acrylamide (Compound 42)

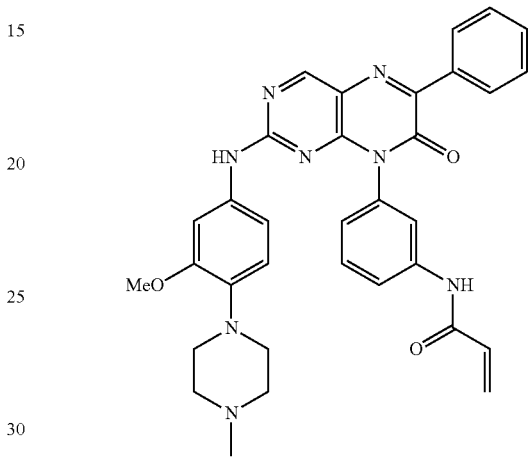

red solids (yield 81%). mp 264.7-265.5° C. 1H NMR (400 MHz, DMSO-d6): δ10.43 (s, 1H), 10.01 (s, 1H), 8.93 (s, 1H), 8.22-8.19 (m, 2H), 7.90 (d, J=7.6 Hz, 1H), 7.79 (s, 1H), 7.56 (t, J=8.0 Hz, 1H), 7.49 (t, J=3.2 Hz, 1H), 7.17 (d, J=8.4 Hz, 1H), 7.07 (br, 1H), 6.97 (br, 1H), 6.46 (dd, J=16.8 Hz, 10.0 Hz, 1H), 6.27 (dd, J=16.8 Hz, 1.6 Hz, 1H), 5.77 (dd, J=10.0 Hz, 1.6 Hz, 1H), 3.56 (s, 3H), 2.83 (br, 4H), 2.41 (br, 4H), 2.21 (s, 3H). HRMS (ESI) (m/z): [M+H]+ calcd for C33H33N8O3, 589.2676; found, 589.2642.

N-(3-(6-cyclohexyl-2-((2-methoxy-4-(4-methyl-1-piperazinyl)phenyl)amino)-7-oxo-8(7H)pteridinyl)phenyl)acrylamide (Compound 43)

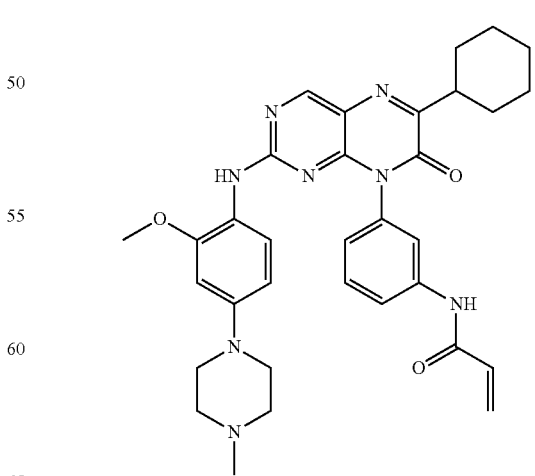

yellow solids (yield 82%). mp 268.9-269.4° C. 1H NMR (400 MHz, DMSO-d6): δ10.40 (s, 1H), 8.73 (s, 1H), 8.24 (s, 1H), 7.85 (d, J=8.0 Hz, 1H), 7.69 (t, J=1.6 Hz, 1H), 7.52 (t, J=8.0 Hz, 1H), 7.33 (d, J=9.2 Hz, 1H), 7.10-7.08 (m, 1H), 6.53 (d, J=2.4 Hz, 1H), 6.45 (dd, J=16.8 Hz, 10.0 Hz, 1H), 6.26 (dd, J=16.8 Hz, 2.0 Hz, 1H), 6.06 (br, 1H), 5.77 (dd, J=10.0 Hz, 2.0 Hz, 1H), 3.76 (s, 3H), 3.03 (br, 4H), 2.43 (t, J=4.8 Hz, 4H), 2.22 (s, 3H), 3.41 (d, J=12.0 Hz, 2H), 1.82 (d, J=12.0 Hz, 2H), 1.72 (d, J=12.0 Hz, 2H), 1.53-1.23 (m, 6H). HRMS (ESI) (m/z): [M+H]$^+$ calcd for $C_{33}H_{39}N_8O_3$, 595.3145; found, 595.3141.

(S)-8-(1-acryloyl-3-piperidinyl)methyl)-2-((2-methoxy-4-(4-methyl-1-piperazinyl)phenyl)amino)-6-phenyl-7(8H)pteridinone (Compound 44)

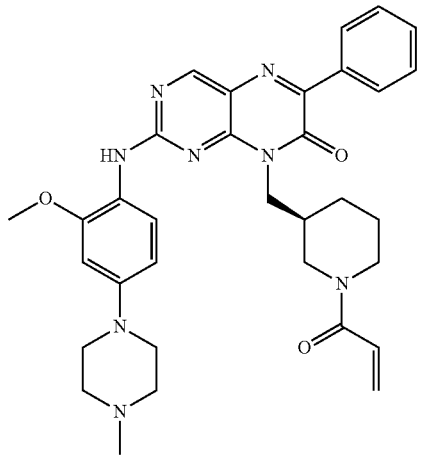 [SMILES: C=CC(=O)N1CCC[C@H](Cn2c(=O)c(-c3ccccc3)nc3cnc(Nc4ccc(N5CCN(C)CC5)cc4OC)nc32)C1]

red solids (yield 49%). mp 208.3-209.3° C. $^1$H NMR (400 MHz, DMSO-d$_6$): δ8.88 (s, 1H), 8.81 (s, 1H), 8.18-8.16 (m, 2H), 7.59-7.52 (m, 1H), 7.47 (t, J=3.2 Hz, 3H), 6.75 (dd, J=16.4 Hz, 10.0, 1H), 6.64 (s, 1H), 6.55 (dd, J=17.2 Hz, 8.8 Hz, 1H), 6.03 (d, J=16.4 Hz, 1H), 5.58 (dd, J=32.8 Hz, 10.0 Hz, 1H), 4.19-4.06 (m, 3H), 3.89-3.83 (m, 1H), 3.79 (s, 3H), 3.17 (br, 4H), 3.05-2.55 (m, 2H), 2.48 (t, J=4.8 Hz, 4H), 2.24 (s, 3H), 2.00 (br, 1H), 1.66 (br, 2H), 1.26-1.23 (m, 2H). HRMS (ESI) (m/z): [M+H]$^+$ calcd for $C_{33}H_{39}N_8O_3$, 595.3145; found, 595.3157.

(R)-8-(1-acryloyl-3-piperidinyl)-2-((2-methoxy-4-(4-methyl-1-piperazinyl)phenyl)amino)-6-phenyl-7(8H) pteridinone (Compound 45)

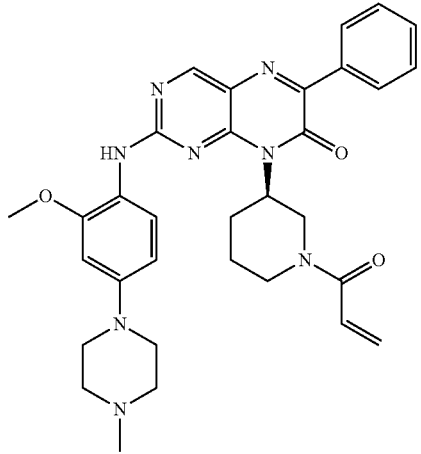 [SMILES: C=CC(=O)N1CCC[C@@H](n2c(=O)c(-c3ccccc3)nc3cnc(Nc4ccc(N5CCN(C)CC5)cc4OC)nc32)C1]

red solids (yield 38%). mp 134.9-135.1° C. $^1$H NMR (400 MHz, DMSO-d$_6$): δ9.17 (s, 1H), 8.79 (s, 1H), 8.11-8.09 (m, 2H), 7.77-7.46 (m, 3H), 7.24 (br, 1H), 6.84-6.63 (m, 2H), 6.49 (s, 1H), 6.06-6.19 (m, 1H), 5.67 (dd, J=37.2 Hz, 9.6 Hz, 1H), 5.00-4.27 (m, 3H), 3.75 (s, 3H), 3.14 (s, 4H), 2.49 (s, 4H), 2.24 (s, 3H), 1.69 (br, 2H), 1.35 (br, 1H), 1.23 (s, 1H). HRMS (ESI) (m/z): [M+H]$^+$ calcd for $C_{32}H_{37}N_8O_3$, 581.2989; found, 581.2972.

(R)-8-(1-acryloyl-3-piperidinyl)-6-cyclohexyl-2-((2-methoxy-4-(4-methyl-1-piperazinyl)phenyl)amino)-7 (8H)pteridinone (Compound 46)

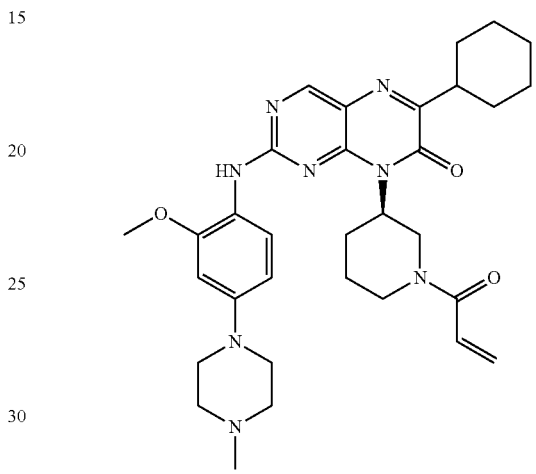

yellow solids (yield 53%). mp 94.2-94.7° C. $^1$H NMR (400 MHz, DMSO-d$_6$): δ8.96 (s, 1H), 8.65 (s, 1H), 7.23 (br, 1H), 6.83-6.61 (m, 2H), 6.47 (s, 1H), 6.15-6.08 (m, 1H), 5.66 (dd, J=36 Hz, 9.6 Hz, 1H), 4.84 (br, 1H), 4.29 (br, 1H), 3.95 (br, 1H), 3.72 (s, 3H), 3.13 (br, 4H), 2.46 (br, 4H), 2.23 (s, 3H), 1.81-1.63 (m, 7H), 1.44-1.23 (m, 9H). HRMS (ESI) (m/z): [M+H]$^+$ calcd for $C_{32}H_{43}N_8O_3$, 587.3458; found 587.3458.

N-(3-(2-((3-methyl-4-(4-methyl-1-piperazinyl)phenyl)amino)-7-oxy-6-phenyl-8(7H)pteridinyl)phenyl) acrylamide (Compound 47)

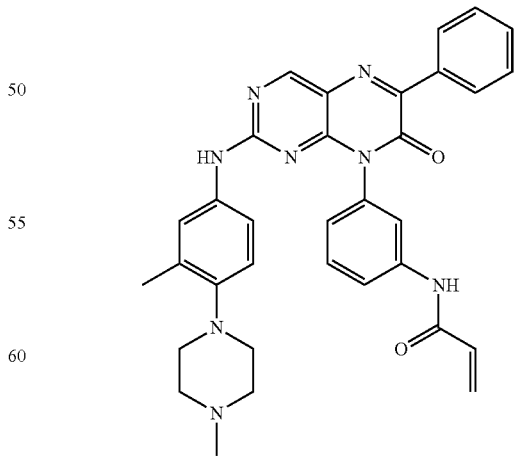

orange solids (yield 68%). mp 265.0-265.2° C. $^1$H NMR (400 MHz, DMSO-d$_6$): δ10.43 (s, 1H), 10.04 (s, 1H), 8.92 (s, 1H), 8.22-8.19 (m, 2H), 7.89 (d, J=8.0 Hz, 1H), 7.81 (s, 1H), 7.57 (t, J=8.0 Hz, 1H), 7.50-7.49 (m, 3H), 7.25 (s, 1H), 7.19 (s, 1H), 7.17 (s, 1H), 6.71 (br, 1H), 6.46 (dd, J=16.8 Hz, 10.4 Hz, 1H), 6.26 (dd, J=16.8 Hz, 1.6 Hz, 1H), 5.77 (dd, J=10.4 Hz, 1.6 Hz, 1H), 2.7 (br, 4H), 2.44 (br, 4H), 2.23 (s, 3H), 1.98 (s, 3H). HRMS (ESI) (m/z): [M+H]$^+$ calcd for $C_{33}H_{33}N_8O_2$, 573.2726; found, 573.2729.

N-(3-(2-((2-methoxy-4-(4-(4-methyl-1-piperazinyl)piperidinyl)phenyl)amino)-7-oxo-6-phenyl-8(7H)pteridinyl)phenyl)acrylamide (Compound 48)

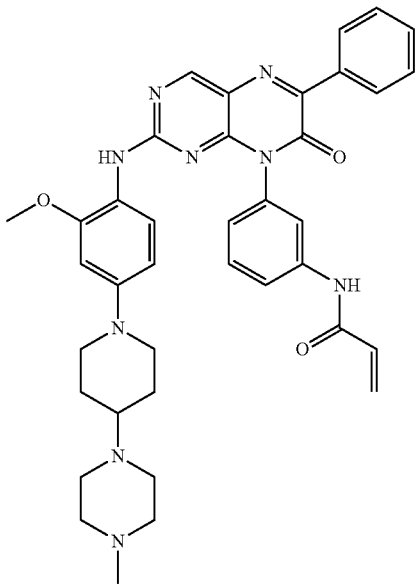 [SMILES: C=CC(=O)Nc1cccc(-n2c(=O)c(-c3ccccc3)nc3cnc(Nc4ccc(N5CCC(N6CCN(C)CC6)CC5)cc4OC)nc32)c1]

red solids (yield 40%). mp>300° C. $^1$H NMR (400 MHz, DMSO-d$_6$): δ 10.44 (s, 1H), 8.86 (s, 1H), 8.41 (s, 1H), 8.20-8.19 (m, 2H), 7.90 (br, 1H), 7.75 (s, 1H), 7.54 (t, J=8.0 Hz, 1H), 7.50-7.48 (m, 3H), 7.33 (d, J=6.4 Hz, 1H), 7.15 (d, J=8.0 Hz, 1H), 6.52 (br, 1H), 6.47 (dd, J=16.8 Hz, 10.0 Hz, 1H), 6.27 (dd, J=16.8 Hz, 1.6 Hz, 1H), 6.04 (br, 1H), 5.78 (dd, J=10.0 Hz, 1.6 Hz, 1H), 3.77 (s, 3H), 3.61 (d, J=8.4 Hz, 2H), 2.60-2.54 (m, 5H), 2.39-2.30 (m, 5H), 1.81 (d, J=11.6 Hz, 2H), 1.51-1.43 (m, 2H). HRMS (ESI) (m/z): [M+H]$^+$ calcd for $C_{38}H_{42}N_9O_3$, 672.3411; found, 672.3407.

8-(1-acryloyl-3-pyrrolidinyl)-2-((3-methyl-4-(4-methyl-1-piperazinyl)phenyl)amino)-6-phenyl-7(8H)pteridinone (Compound 49)

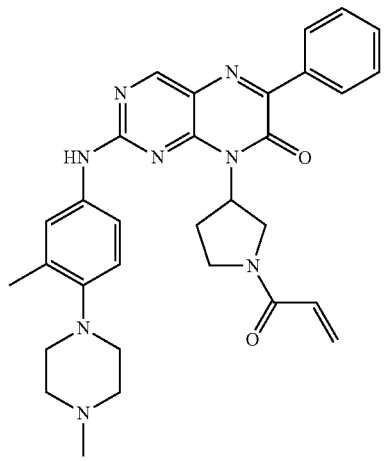 [SMILES: C=CC(=O)N1CCC(n2c(=O)c(-c3ccccc3)nc3cnc(Nc4ccc(N5CCN(C)CC5)c(C)c4)nc32)C1]

orange solids (yield 65%). $^1$H NMR (400 MHz, DMSO-d$_6$): δ10.08 (s, 1H), 8.87 (d, J=2.8 Hz, 1H), 8.13-8.11 (m, 2H), 7.51-7.46 (m, 5H), 6.97-6.93 (m, 1H), 6.70 (dd, J=16.8 Hz, 10.4 Hz, 1H), 6.51 (dd, J=16.8 Hz, 10.4 Hz, 1H), 6.23-6.15 (m, 1H), 6.11-6.01 (m, 1H), 5.75-5.65 (m, 1H), 4.25 (t, J=8.8 Hz, 1H), 4.06-3.68 (m, 3H), 3.52-3.45 (m, 1H), 2.95-2.86 (m, 1H), 2.79 (br, 4H), 2.46 (br, 4H), 2.23 (s, 3H), 2.21 (s, 3H), 2.17-2.12 (m, 1H). HRMS (ESI) (m/z): [M+H]$^+$ calcd for $C_{31}H_{35}N_8O_2$, 551.2883; found, 551.2883.

(S)-8-(1-acryloyl-3-pyrrolidinyl)-6-cyclohexyl-2-((2-methoxy-4-(4-methyl-1-piperazinyl)phenyl)amino)-7(8H)pteridinone (Compound 50)

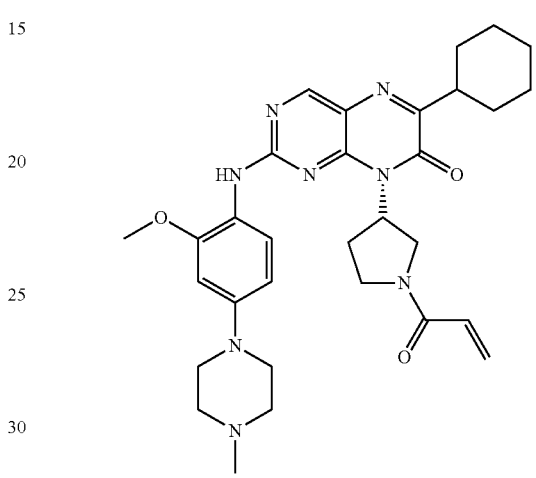

orange solids (yield 49%). mp 117.9-118.2° C. $^1$H NMR (400 MHz, DMSO-d$_6$): δ 8.71 (s, 1H), 8.66 (d, J=3.6 Hz, 1H), 7.39 (t, J=8.0 Hz, 1H), 6.63-6.59 (m, 0.5H), 6.57 (s, 1H), 6.49-6.45 (m, 0.5H), 6.41 (d, J=9.2 Hz, 1H), 6.20-6.13 (m, 1H), 5.82 (br, 1H), 5.73-5.63 (m, 1H), 4.11 (t, J=9.2 Hz, 0.5H), 3.87 (dd, J=12.0 Hz, 8.8 Hz, 0.5H), 3.69-3.58 (m, 2H), 3.18-3.04 (m, 5H), 2.80-2.65 (m, 1H), 2.45 (br, 4H), 2.23 (s, 3H), 2.09 (br, 0.5H), 1.99 (br, 0.5H), 1.81 (t, J=11.2 Hz, 4H), 1.70 (d, J=11.2 Hz, 1H), 1.45-1.16 (m, 6H). HRMS (ESI) (m/z): [M+H]$^+$ calcd for $C_{31}H_{41}N_8O_3$, 573.3302; found, 573.3304.

8-(3-aminophenyl)-2-((2-methoxy-4-(4-methyl-1-piperazinyl)phenyl)amino)-6-phenyl-7(8H)pteridinone (Compound 51)

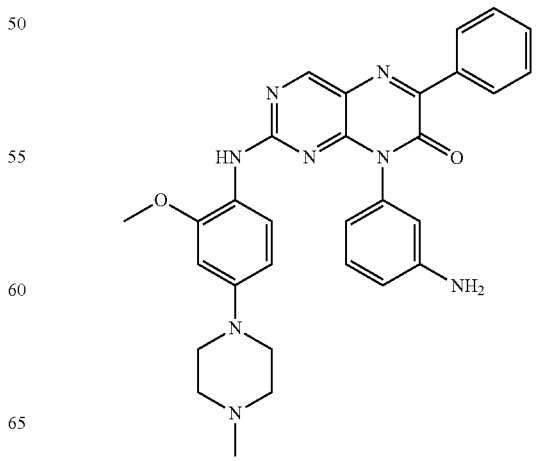

orange solids (yield 84%). mp 235.5-235.7° C. ¹H NMR (400 MHz, DMSO-d₆): δ 8.84 (s, 1H), 8.39 (br, 1H), 8.19-8.17 (m, 2H), 7.49-7.47 (m, 4H), 7.21 (t, J=8.0 Hz, 1H), 6.72 (d, J=7.2 Hz, 1H), 6.571-6.56 (m, 2H), 6.52 (d, J=8.0 Hz, 1H), 6.19 (br, 1H), 5.34 (s, 2H), 3.79 (s, 3H), 3.08 (br, 4H), 2.45 (t, J=4.4 Hz, 4H), 2.23 (s, 3H). HRMS (ESI) (m/z): [M+H]⁺ calcd for $C_{30}H_{31}N_8O_2$, 535.2570; found, 535.2569.

N-(3-(6-(4-fluorophenyl)-2-((2-methoxy-4-(4-methyl-1-piperazinyl)phenyl)amino)-7-oxo-8(7H)pteridinyl)phenyl)acrylamide (Compound 52)

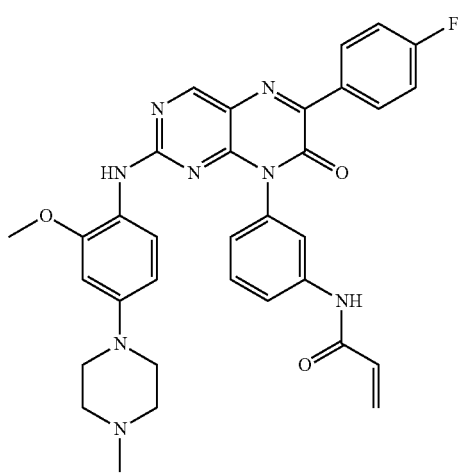 [SMILES: C=CC(=O)Nc1cccc(-n2c(=O)c(-c3ccc(F)cc3)nc3cnc(Nc4ccc(N5CCN(C)CC5)cc4OC)nc32)c1]

orange solids (yield 73%). mp 262.3-262.7° C. ¹H NMR (400 MHz, DMSO-d₆): δ 10.43 (s, 1H), 8.87 (s, 1H), 8.44 (s, 1H), 8.29 (dd, J=8.4 Hz, 6.0 Hz, 1H), 7.89 (br, 1H), 7.77 (s, 1H), 7.55 (t, J=8.0 Hz, 1H), 7.36-7.31 (m, 3H), 7.15 (d, J=8.4 Hz, 1H), 6.54 (s, 1H), 6.47 (dd, J=16.8 Hz, 10.0 Hz, 1H), 6.28 (dd, J=16.8 Hz, 1.6 Hz, 1H), 6.04 (br, 1H), 5.78 (dd, J=10.0 Hz, 1.6 Hz, 1H), 3.78 (s, 3H), 3.05 (br, 4H), 2.44 (t, J=4.4 Hz, 4H), 2.23 (s, 3H). HRMS (ESI) (m/z): [M+H]⁺ calcd for $C_{33}H_{32}N_8O_3F$, 607.2581; found, 607.2589.

(S)-8-(1-acryloyl-3-piperidinyl)methyl)-2-((2-methoxy-4-(4-methyl-1-piperazinyl)phenyl)amino)-6-phenyl-7(8H)pteridinone (Compound 53)

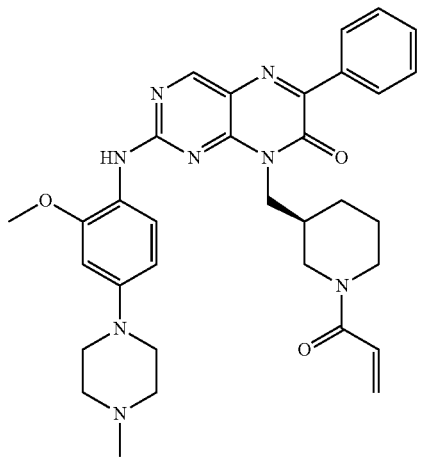 [SMILES: C=CC(=O)N1CCC[C@H](Cn2c(=O)c(-c3ccccc3)nc3cnc(Nc4ccc(N5CCN(C)CC5)cc4OC)nc32)C1]

red solids, yield 49%. mp 208.3-209.3° C. ¹H NMR (400 MHz, DMSO-d₆): δ 8.88 (s, 1H), 8.81 (s, 1H), 8.18-8.16 (m, 2H), 7.59-7.52 (m, 1H), 7.47 (t, J=3.2 Hz, 3H), 6.75 (dd, J=16.4 Hz, 10.0, 1H), 6.64 (s, 1H), 6.55 (dd, J=17.2 Hz, 8.8 Hz, 1H), 6.03 (d, J=16.4 Hz, 1H), 5.58 (m, 1H), 4.19-4.06 (m, 3H), 3.89-3.83 (m, 1H), 3.79 (s, 3H), 3.17 (br, 4H), 3.05-2.55 (m, 2H), 2.48 (t, J=4.8 Hz, 4H), 2.24 (s, 3H), 2.00 (br, 1H), 1.66 (br, 2H), 1.26-1.23 (m, 2H). HPLC purity: 95.1%, Retention time=15.82 min. HRMS (ESI) (m/z): [M+H]⁺ calcd for $C_{33}H_{39}N_8O_3$, 595.3145; found, 595.3157.

N-(3-(2-((2-methoxy-4-(4-methyl-1-piperazinyl)phenyl)amino)-6-(4-methoxyphenyl)-7-oxo-8(7H)pteridinyl)phenyl)acrylamide (Compound 54)

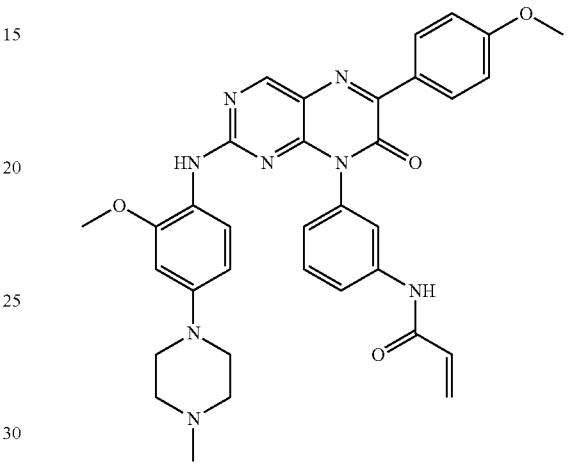

orange solids (yield 65%). mp 296.5-297.3° C. ¹H NMR (400 MHz, DMSO-d₆): δ 10.43 (s, 1H), 8.84 (s, 1H), 8.34 (s, 1H), 8.26 (d, J=8.8 Hz, 1H), 7.89 (d, J=7.2 Hz, 1H), 7.74 (s, 1H), 7.55 (t, J=8.0 Hz, 1H), 7.36 (d, J=8.4 Hz, 1H), 7.15 (d, J=8.4 Hz, 1H), 7.05 (d, J=9.2 Hz, 1H), 6.54 (s, 1H), 6.47 (dd, J=16.8 Hz, 10.0 Hz, 1H), 6.27 (dd, J=16.8 Hz, 1.6 Hz, 1H), 6.06 (br, 1H), 5.78 (d, J=10.0 Hz, 1.6 Hz, 1H), 3.84 (s, 3H), 3.78 (s, 3H), 3.05 (br, 4H), 2.44 (br, 4H), 2.23 (s, 3H). HRMS (ESI) (m/z): [M+H]⁺ calcd for $C_{34}H_{35}N_8O_4$, 619.2781; found, 619.2780.

N-(3-(6-(3,5-difluorophenyl)-2-((2-methoxy-4-(4-methyl-1-piperazinyl)phenyl)amino)-7-oxo-8(7H)pteridinyl)phenyl)acrylamide (Compound 55)

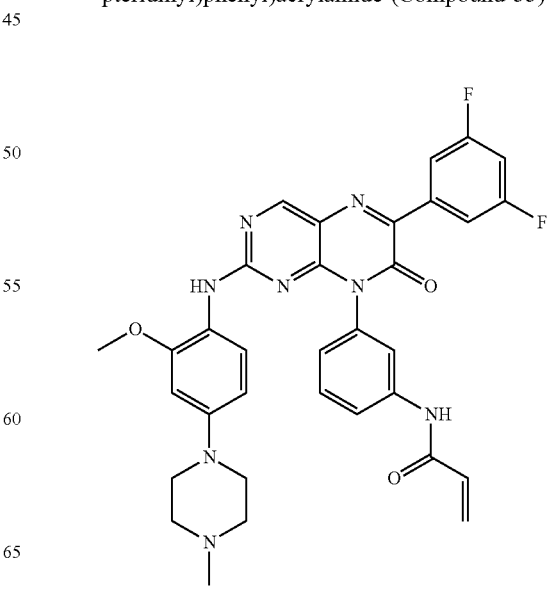

red solids (yield 64%). mp 291.2-291.4° C. ¹H NMR (400 MHz, DMSO-d₆): δ 10.43 (s, 1H), 8.92 (s, 1H), 8.57 (s, 1H), 7.96 (d, J=7.2 Hz, 1H), 7.87 (br, 1H), 7.77 (s, 1H), 7.54 (t, J=8.0 Hz, 1H), 7.43-7.39 (m, 1H), 7.33 (s, 1H), 7.14 (d, J=7.2 Hz, 1H), 6.54 (s, 1H), 6.47 (dd, J=16.8 Hz, 10.0, 1H), 6.27 (dd, J=16.8 Hz, 1.6 Hz, 1H), 6.00 (br, 1H), 5.78 (dd, J=10.0 Hz, 1.6 Hz, 1H), 3.77 (s, 3H), 3.05 (br, 4H), 2.43 (br, 4H), 2.22 (s, 3H). HRMS (ESI) (m/z): [M+H]⁺ calcd for C₃₃H₃₀N₈O₃F₂, 625.2487; found, 625.2482.

N-(3-(6-(3,4-difluorophenyl)-2-((2-methoxy-4-(4-methyl-1-piperazinyl)phenyl)amino)-7-oxo-8(7H)pteridinyl)phenyl)acrylamide (Compound 56)

Brown solids (yield 52%). Mp>300° C. ¹H NMR (400 MHz, DMSO-d₆): δ 10.42 (s, 1H), 8.88 (s, 1H), 8.45 (s, 1H), 7.89 (s, 1H), 7.82-7.81 (m, 2H), 7.76 (s, 1H), 7.55 (t, J=8.0 Hz, 1H), 7.41 (t, J=8.0 Hz, 1H), 7.36-7.34 (br, 1H), 7.16 (d, J=7.6 Hz, 1H), 7.08 (d, J=8.4 Hz, 1H), 6.54 (s, 1H), 6.47 (dd, J=16.8 Hz, 10.4 Hz, 1H), 6.28 (d, J=17.2 Hz, 1H), 6.04 (br, 1H), 5.80 (m, 1H), 3.82 (s, 3H), 3.78 (s, 3H), 3.05 (br, 4H), 2.44 (br, 4H), 2.23 (s, 3H). HRMS (ESI) (m/z): [M+H]⁺ calcd for C₃₄H₃₅N₈O₄, 619.2781; found, 619.2780.

8-(1-acryloyl-3-piperidinyl)-2-((2-methoxy-4-(4-methyl-1-piperazinyl)phenyl)amino)-6-phenyl-7(8H)pteridinone (Compound 58)

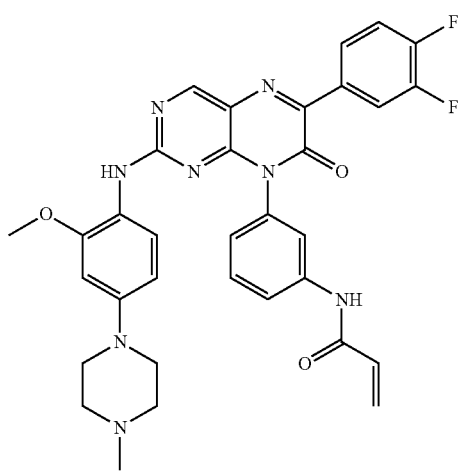

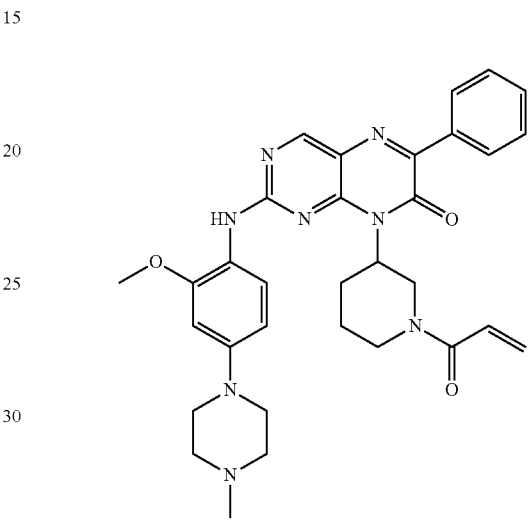

orange solids (yield 67%). Mp>300° C. ¹H NMR (400 MHz, DMSO-d₆): δ 10.43 (s, 1H), 8.89 (s, 1H), 8.50 (br, 1H), 8.28-8.23 (m, 1H), 8.15 (br, 1H), 7.87 (s, 1H), 7.77 (s, 1H), 7.61-7.52 (m, 2H), 7.34 (s, 1H), 7.14 (d, J=8.4 Hz, 1H), 6.54 (s, 1H), 6.47 (dd, J=16.8 Hz, 10.0 Hz, 1H), 6.27 (dd, J=16.8 Hz, 1.6 Hz, 1H), 6.02 (br, 1H), 5.78 (dd, J=10.0 Hz, 1.6 Hz, 1H), 3.77 (s, 3H), 3.05 (br, 4H), 2.43 (t, J=4.4 Hz, 4H), 2.22 (s, 3H). HRMS (ESI) (m/z): [M+H]⁺ calcd for C₃₃H₃₁N₈O₃F₂, 625.2487; found, 625.2478.

N-(3-(2-((2-methoxy-4-(4-methyl-1-piperazinyl)phenyl)amino)-6-(3-methoxyphenyl)-7-oxo-8(7H)pteridinyl)phenyl)acrylamide (Compound 57)

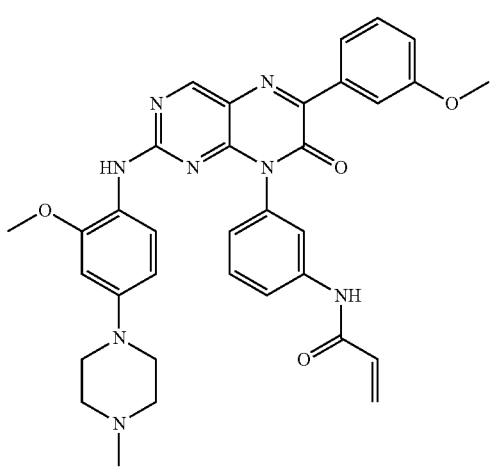

orange solids (yield 40%). mp ¹H NMR (400 MHz, DMSO-d₆): δ 9.19 (s, 1H), 8.78 (s, 1H), 8.11-8.09 (m, 2H), 7.47-7.46 (m, 3H), 7.22 (br, 1H), 6.88-6.63 (m, 2H), 6.49 (br, 1H), 6.06-6.19 (m, 1H), 5.67 (dd, J=36.8 Hz, 10 Hz, 1H), 4.91-3.99 (m, 3H), 3.74 (s, 3H), 3.14 (br, 4H), 2.47 (br, 4H), 2.24 (s, 3H), 1.69 (br, 2H), 1.35 (br, 1H), 1.23 (s, 1H). HRMS (ESI) (m/z): [M+H]⁺ calcd for C₃₂H₃₇N₈O₃, 581.2989; found, 581.2992.

Example 2

Assay on Bioactivity: Activity Test on Molecular Level (Kinase)

EGFR-TK catalyses transfer of one phosphate group of adenosine triphosphate (ATP) to polypeptide substrate, poly (Glu, Tyr)₄:₁, which is labeled with two fluorescent groups coumarin and fluorescein. Based on fluorescence energy resonance transfer (FRET) method, EGFR-TK catalyzes a reaction of ATP, resulting in two fluorescent groups approaching, exciting donator (coumarin) at 400 nM, releasing part of energy (emission wavelength at 445 nM), and transferring other part of energy to fluorescein (emission wavelength at 520 nM). Different compounds exhibited different inhibition-degrees on EGFR-TK, leading to different phosphorylation-degrees of substrate, so that the inhibition ratio of different compounds can be calculated by measuring the ratio of phosphorylation percentage of substrate catalyzed by an enzyme.

1. Experiment Steps:

2.5 μL of Test Compounds, 5 μL Kinase/Peptide Substrate Mixture, 2.5 μL ATP Solution were added into a 384-well plate, and the 10 μL of reaction system was shaken for 30 s and incubated at room temperature for 1 h. 5 μL of Development Solution was added and the 15 μL of reaction system was shaken for 30 s, and incubated at room temperature for 1 h. 5 μL of Stop Reagent was added, the reaction system in a total volume of 20 μL was shaken for 30 s, and a microplate reader was used to detect fluorescence signals at excitation wavelength of 400 nm and emission wavelength of 445 nm and 520 nm, respectively. The inhibitory rates of the compounds at 7 concentration gradients were determined and the $IC_{50}$ value for each compound was calculated by Origin 8.0 fitting curve. Positive controls were used during the experiment to confirm the feasibility of the reaction system, and each experiment was performed in triplicate.

2. Calculation Formula:

$$\text{Emission Ratio} = \frac{\text{Coumarin Emission (445 nm)}}{\text{Fluorescein Emission (520 nm)}}$$

$$\% \text{ Phosphorylation} = 1 - \frac{(\text{Emission Ration} \times F100\%) - C100\%}{(C0\% - C100\%) + \text{Emission Ration} \times (F100\% - F0\%)}$$

$$\% \text{ Inhibition} = \left(1 - \frac{\% \text{ Phos sample}}{\% \text{ Phos 0\% inhibition}}\right) \times 100$$

In Vitro Enzyme Activity Assay: Wild type and various mutant (T790M, L858/T790M) EGFR were purchased from Invitrogen. 10 concentration gradients from $5.1 \times 10^{-11}$ mol/L to $1.0 \times 10^{-6}$ mol/L were set for all compounds to be tested.

The concentration of different kinases was determined by optimization experiments and the corresponding concentrations were: EGFR (PV3872, Invitrogen) 0.287 μg/μL, EGFR-T790M (PV4803, Invitrogen) 0.174 μg/μL, EGFR-L858R/T790M (PV4879, Invitrogen) 0.055 μg/μL. Compounds were diluted in DMSO for three times from $5.1 \times 10^{-9}$ M to $1 \times 10^{-4}$ M. 4 μL of the compound was dissolved in 96 μL of water to obtain a 4× compound solution. 40 μM ATP was dissolved in 1.33× kinase buffer and the kinase/peptide mixture contained 2× kinase, 4 μM tyrosine tetrapeptide for use. The 10 μL kinase reaction consisted of 2.5 μL compound solution, 5 μL kinase/peptide mix, 2.5 μL ATP solution. 10 μL of kinase reaction included 2.5 μL, of compound solution, 5 μL of kinase/peptide mixture, 2.5 μL of ATP solution. 5 μL of phosphorylated peptide solution, instead of the kinase/peptide mixture, was used as a 100% phosphorylation control. 2.5 μL of 1.33× kinase buffer, instead of ATP solution was used as a 100% inhibition control and 2.5 μL of 4% DMSO, instead of compound solution was used as a 0% inhibition control. The plates were thoroughly mixed and incubated at room temperature for 1.5 hours. 5 μL of Development Solution was added into each well and then incubated for another 1 hour at room temperature, unphosphorylated peptides were cleaved during this period. Finally, 5 μL Stop Reagent was added to quench the reaction. The plates were measured with EnVision Multilabel Reader (Perkin Elmer). The experimental data were calculated using GraphPad Prism version 4.0. Each experiment was repeated more than 3 times.

Example 3

Cell Activity Test (Inhibitory Activity on Cell Proliferation)

Inhibition Analysis on Cell Proliferation and Growth: H1975 (non-small cell lung cancer cells, EGFRL858R/T790M), A431 (non-small cell lung cancer cells, EGFR wild type) cells were obtained from the ATCC. Cell proliferation activity was assessed by MTS assay. Cells were exposed to processing conditions for 72 hours and the number of cells used in each experiment for each cell line was adjusted based on absorbance values (absorbance values at 490 nm, 1.3-2.2). Six concentration gradients (0.1 nM-10 μM) were set for the compounds to be tested, wherein at least 6 sets of parallel controls for each concentration were used.

H1975, A431 cells were cultured in corresponding media, and cells were passaged at least twice after resuscitation and then used for experiments. Cells at Log phase were trypsinized and resuspended in culture medium. H1975 (1000 cells per well), A431 (2000 cells per well) were seeded in 96-well plates in a volume of 100 μL; and 6 sets of parallel controls and 7 columns were set. The plate was placed in a 37° C. 5% $CO_2$ incubator overnight. Compounds were dissolved in DMSO to a concentration of 10 μM per liter, and then the concentration was gradually diluted to 10 μM, 1 μM, 0.1 μM, 0.01 μM, 0.001 μM, 0.0001 μM per liter, respectively. 2 μL of the compound solution was added to 998 μL of medium, and the mixture was thoroughly mixed. 100 μL of the mixture was added to a 96-well plate. 2 μL of DMSO, instead of compound solution was used as a 0% inhibition control. After culturing for 68 hours, 20 μL of MTT (5 mg/mL) was added. After 4 hours, the supernatant was discarded and 150 μL of DMSO was added. After shaking for 10 minutes, the plate was read with Synergy HT (Bio TeK) (OD490). Data were calculated using GraphPad Prism version 4.0 and $IC_{50}$ values were obtained using a non-linear regression model of dose response curve.

Determination of solubility in water: About 2 mg of the compound to be tested was weighed into a 1.5 mL centrifuge tube and 1 mL of PBS buffer (20 mM, pH=6.8) was added, sonicated for 5 minutes (if the compound was completely dissolved, 2 mg of the compound was added again), and shaken overnight. The suspension was filtered through a 0.22 μm PVDF filter, and then diluted to an appropriate concentration with methanol (v=50%) and PBS (v=50%), and the absorbance was measured by a UV spectrophotometer. About 3 mg of compound was accurately weighed, and methanol was added for preparing a stock solution of 1 mg/mL. The above stock solution was taken and prepared into a solution at concentrations of 0.05, 0.04, 0.03, 0.02 and 0.01 mg/mL, respectively, PBS solution (v=50%) was added and the absorbance value was measured. Concentration c (mg/mL) as horizontal ordinate vs absorbance A as longitudinal coordinate was plotted, and a line was fitted for obtaining a standard curve (correlation coefficient greater than 0.998). The solubility of a compound in water was calculated from the standard curve.

Test results are shown in following Table 1.

TABLE 1

Kinase levels and selectivity, cellular level and selectivity, and partial solubility of Compound

| Number of compound | Structure of compound | Inhibitory activity of EGFR on kinase (IC$_{50}$, nM) | | Inhibitory activity on proliferation of cells (IC$_{50}$, μM) | | Solubility (pH 6.8, g/mL) |
|---|---|---|---|---|---|---|
| | | WT | T790M/L858R | H1975 | A431 | |
| 1 | | 250.5 | 129.0 | 12.16 | 13.75 | 1279.4 |
| 2 | | >10 uM | >10 uM | 18.25 | 89.61 | 11082 |
| 3 | | >10 uM | >10 uM | 33.67 | 60.62 | >11352 |

TABLE 1-continued

Kinase levels and selectivity, cellular level and selectivity, and partial solubility of Compound

| Number of compound | Structure of compound | Inhibitory activity of EGFR on kinase (IC$_{50}$, nM) | | Inhibitory activity on proliferation of cells (IC$_{50}$, μM) | | Solubility (pH 6.8, g/mL) |
|---|---|---|---|---|---|---|
| | | WT | T790M/L858R | H1975 | A431 | |
| 4 | | 4.5 | 3.9 | 0.009 | 0.94 | 1367 |
| 5 | | 2.4 | 0.6 | 0.006 | 0.82 | 122.4 |
| 6 | | 105.8 | 14.8 | 0.46 | 1.69 | 51.8 |

TABLE 1-continued

Kinase levels and selectivity, cellular level and selectivity, and partial solubility of Compound

| Number of compound | Structure of compound | Inhibitory activity of EGFR on kinase (IC$_{50}$, nM) | | Inhibitory activity on proliferation of cells (IC$_{50}$, μM) | | Solubility (pH 6.8, g/mL) |
|---|---|---|---|---|---|---|
| | | WT | T790M/L858R | H1975 | A431 | |
| 7 | | 45.2 | 9.5 | 0.197 | 20.52 | <25 |
| 8 | | 5.7 | 2.1 | 0.09 | 0.97 | 280.5 |
| 9 | | 23.4 | 20.8 | 1.04 | 2.81 | 162.7 |

TABLE 1-continued

Kinase levels and selectivity, cellular level and selectivity, and partial solubility of Compound

| Number of compound | Structure of compound | Inhibitory activity of EGFR on kinase (IC$_{50}$, nM) | | Inhibitory activity on proliferation of cells (IC$_{50}$, μM) | | Solubility (pH 6.8, g/mL) |
|---|---|---|---|---|---|---|
| | | WT | T790M/L858R | H1975 | A431 | |
| 10 | | 93.7 | 191.1 | 2.60 | 7.53 | 398.7 |
| 11 | | 2.2 | 7.3 | 0.20 | 8.09 | 48.6 |
| 12 | | 3.5 | 6.2 | 0.006 | 2.52 | 369.4 |

TABLE 1-continued
Kinase levels and selectivity, cellular level and selectivity, and partial solubility of Compound
| Number of compound | Structure of compound | Inhibitory activity of EGFR on kinase (IC$_{50}$, nM) | | Inhibitory activity on proliferation of cells (IC$_{50}$, μM) | | Solubility (pH 6.8, g/mL) |
|---|---|---|---|---|---|---|
| | | WT | T790M/L858R | H1975 | A431 | |
| 13 | 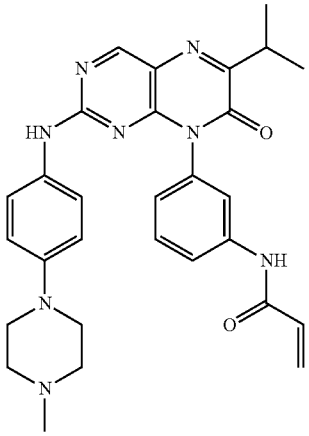 [SMILES: C=CC(=O)Nc1cccc(-n2c(=O)c(C(C)C)nc3cnc(Nc4ccc(N5CCN(C)CC5)cc4)nc32)c1] | 4.2 | 5.7 | 0.046 | 1.48 | 8.9 |
| 14 | 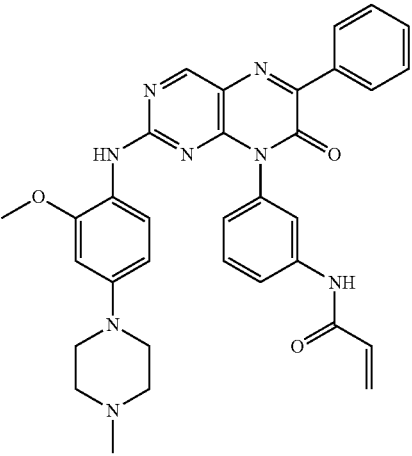 [SMILES: C=CC(=O)Nc1cccc(-n2c(=O)c(-c3ccccc3)nc3cnc(Nc4ccc(N5CCN(C)CC5)cc4OC)nc32)c1] | 10.5 | 1.0 | 0.014 | 4.18 | 9.7 |
| 15 | 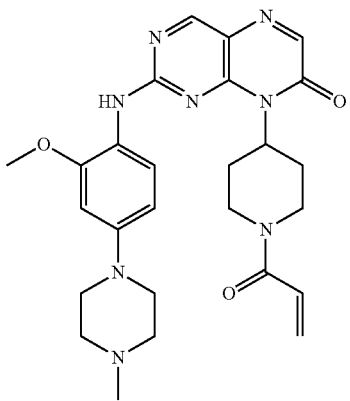 [SMILES: C=CC(=O)N1CCC(n2c(=O)cnc3cnc(Nc4ccc(N5CCN(C)CC5)cc4OC)nc32)CC1] | 2296 | 2250 | 3.60 | 8.13 | 514 |

TABLE 1-continued

Kinase levels and selectivity, cellular level and selectivity, and partial solubility of Compound

| Number of compound | Structure of compound | Inhibitory activity of EGFR on kinase (IC$_{50}$, nM) | | Inhibitory activity on proliferation of cells (IC$_{50}$, μM) | | Solubility (pH 6.8, g/mL) |
|---|---|---|---|---|---|---|
| | | WT | T790M/L858R | H1975 | A431 | |
| 16 | | 4704 | >10000 | >10 | >10 | 956 |
| 17 | | 2190 | 191 | 1.42 | >10 | 957 |
| 18 | | 47 | 1.0 | 0.06 | 1.66 | 208.2 |

TABLE 1-continued
Kinase levels and selectivity, cellular level and selectivity, and partial solubility of Compound
| Number of compound | Structure of compound | Inhibitory activity of EGFR on kinase (IC$_{50}$, nM) | | Inhibitory activity on proliferation of cells (IC$_{50}$, μM) | | Solubility (pH 6.8, g/mL) |
|---|---|---|---|---|---|---|
| | | WT | T790M/L858R | H1975 | A431 | |
| 19 | 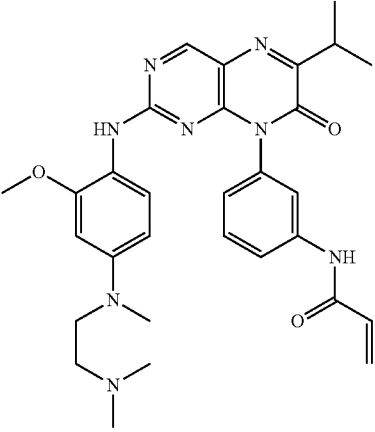 [SMILES: C=CC(=O)Nc1cccc(-n2c(=O)c(C(C)C)nc3cnc(Nc4ccc(N(C)CCN(C)C)cc4OC)nc32)c1] | 174.2 | 14.1 | 1.16 | 3.41 | 90.7 |
| 20 | 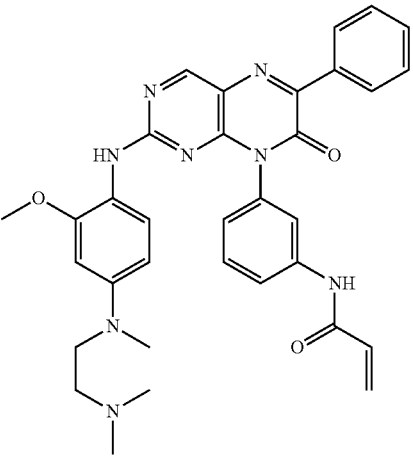 [SMILES: C=CC(=O)Nc1cccc(-n2c(=O)c(-c3ccccc3)nc3cnc(Nc4ccc(N(C)CCN(C)C)cc4OC)nc32)c1] | 15.0 | 1.3 | 0.040 | 6.0 | 7.4 |
| 21 | 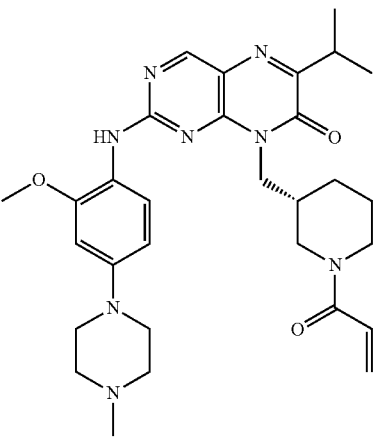 [SMILES: C=CC(=O)N1CCC[C@@H](Cn2c(=O)c(C(C)C)nc3cnc(Nc4ccc(N5CCN(C)CC5)cc4OC)nc32)C1] | 2880 | 251 | 4.49 | >10 | 72.2 |

TABLE 1-continued

Kinase levels and selectivity, cellular level and selectivity, and partial solubility of Compound

| Number of compound | Structure of compound | Inhibitory activity of EGFR on kinase (IC$_{50}$, nM) | | Inhibitory activity on proliferation of cells (IC$_{50}$, μM) | | Solubility (pH 6.8, g/mL) |
|---|---|---|---|---|---|---|
| | | WT | T790M/L858R | H1975 | A431 | |
| 22 | | >10000 | 6897 | >10 | >10 | 3232 |
| 23 | | 1730 | 939 | 1.85 | 3.20 | 1689 |
| 24 | | 700 | 576 | 2.49 | 3.1 | 2918 |

TABLE 1-continued
Kinase levels and selectivity, cellular level and selectivity, and partial solubility of Compound
| Number of compound | Structure of compound | Inhibitory activity of EGFR on kinase (IC$_{50}$, nM) | | Inhibitory activity on proliferation of cells (IC$_{50}$, μM) | | Solubility (pH 6.8, g/mL) |
|---|---|---|---|---|---|---|
| | | WT | T790M/L858R | H1975 | A431 | |
| 25 | 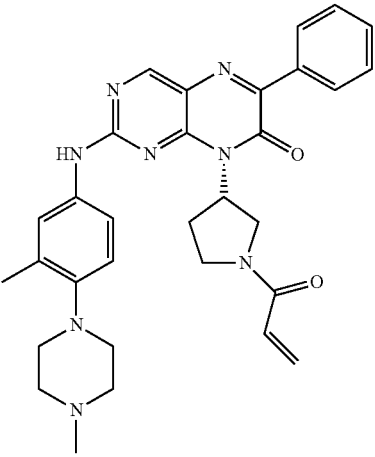 | 65.2 | 1.5 | 0.016 | 1.75 | 56.67 |
| 26 | 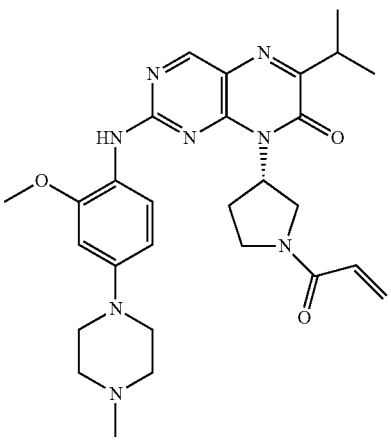 [SMILES: C=CC(=O)N1CC[C@H](n2c(=O)c(C(C)C)nc3cnc(Nc4ccc(N5CCN(C)CC5)cc4OC)nc32)C1] | 1302 | 559 | 3.23 | 9.5 | 10515 |
| 27 | 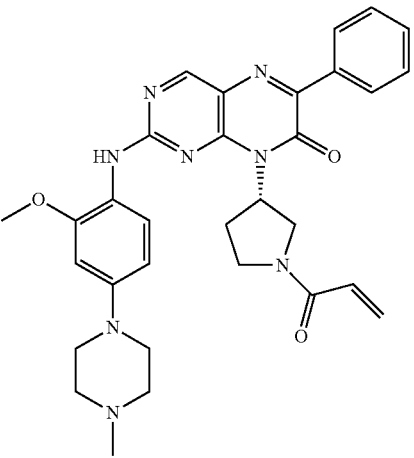 [SMILES: C=CC(=O)N1CC[C@H](n2c(=O)c(-c3ccccc3)nc3cnc(Nc4ccc(N5CCN(C)CC5)cc4OC)nc32)C1] | 53.7 | 3.8 | 0.116 | 1.85 | 263.5 |

TABLE 1-continued

Kinase levels and selectivity, cellular level and selectivity, and partial solubility of Compound

| Number of compound | Structure of compound | Inhibitory activity of EGFR on kinase (IC$_{50}$, nM) | | Inhibitory activity on proliferation of cells (IC$_{50}$, μM) | | Solubility (pH 6.8, g/mL) |
|---|---|---|---|---|---|---|
| | | WT | T790M/L858R | H1975 | A431 | |
| 28 | | >10000 | >10000 | 8.38 | >10 | 3969 |
| 29 | | 177 | 791 | 3.09 | 1.6 | 437.5 |
| 30 | | >1000 | >1000 | 8.689 | >10 | >10 |

TABLE 1-continued

Kinase levels and selectivity, cellular level and selectivity, and partial solubility of Compound

| Number of compound | Structure of compound | Inhibitory activity of EGFR on kinase (IC$_{50}$, nM) | | Inhibitory activity on proliferation of cells (IC$_{50}$, μM) | | Solubility (pH 6.8, g/mL) |
|---|---|---|---|---|---|---|
| | | WT | T790M/L858R | H1975 | A431 | |
| 31 | | 522.3 | 9.0 | 2.155 | >10 | 63.3 |
| 32 | | 1.3 | 7.1 | 0.033 | 2.753 | <10 |
| 33 | | 33.0 | 1.3 | 0.230 | 3.682 | 24.5 |

TABLE 1-continued

Kinase levels and selectivity, cellular level and selectivity, and partial solubility of Compound

| Number of compound | Structure of compound | Inhibitory activity of EGFR on kinase (IC$_{50}$, nM) | | Inhibitory activity on proliferation of cells (IC$_{50}$, μM) | | Solubility (pH 6.8, g/mL) |
|---|---|---|---|---|---|---|
| | | WT | T790M/L858R | H1975 | A431 | |
| 34 | | 86.7 | 895.9 | 0.831 | >10 | 223.1 |
| 35 | | 20.1 | 17.5 | 0.378 | 0.225 | 63.3 |
| 36 | | >1000 | >1000 | 2.196 | 9.601 | 737 |

TABLE 1-continued

Kinase levels and selectivity, cellular level and selectivity, and partial solubility of Compound

| Number of compound | Structure of compound | Inhibitory activity of EGFR on kinase (IC$_{50}$, nM) | | Inhibitory activity on proliferation of cells (IC$_{50}$, μM) | | Solubility (pH 6.8, g/mL) |
|---|---|---|---|---|---|---|
| | | WT | T790M/L858R | H1975 | A431 | |
| 37 | | 26.0 | 4.9 | 0.074 | 3.235 | <10 |
| 38 | | 2.8 | 0.6 | 0.165 | 2.345 | <10 |
| 39 | | 130.3 | 82.2 | 0.572 | 3.844 | <10 |

TABLE 1-continued

Kinase levels and selectivity, cellular level and selectivity, and partial solubility of Compound

| Number of compound | Structure of compound | Inhibitory activity of EGFR on kinase (IC$_{50}$, nM) | | Inhibitory activity on proliferation of cells (IC$_{50}$, μM) | | Solubility (pH 6.8, g/mL) |
|---|---|---|---|---|---|---|
| | | WT | T790M/L858R | H1975 | A431 | |
| 40 | | >10000 | 73.1 | 1.052 | 1.377 | >10 |
| 41 | | 5346.8 | 38.6 | 1.186 | 1.263 | >10 |
| 42 | | 527.6 | 47.5 | 0.003 | 0.328 | <10 |

TABLE 1-continued
Kinase levels and selectivity, cellular level and partial solubility of Compound
| Number of compound | Structure of compound | Inhibitory activity of EGFR on kinase (IC$_{50}$, nM) | | Inhibitory activity on proliferation of cells (IC$_{50}$, μM) | | Solubility (pH 6.8, g/mL) |
| --- | --- | --- | --- | --- | --- | --- |
| | | WT | T790M/L858R | H1975 | A431 | |
| 43 | 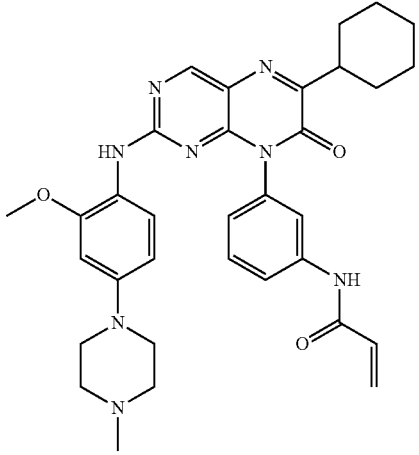 [SMILES: C=CC(=O)Nc1cccc(-n2c(=O)c(C3CCCCC3)nc3cnc(Nc4ccc(N5CCN(C)CC5)cc4OC)nc32)c1] | 7.7 | 0.6 | 0.112 | 0.433 | <10 |
| 44 | 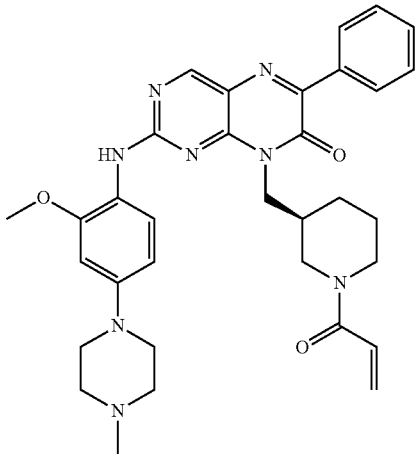 [SMILES: C=CC(=O)N1CCC[C@H](Cn2c(=O)c(-c3ccccc3)nc3cnc(Nc4ccc(N5CCN(C)CC5)cc4OC)nc32)C1] | 343.1 | >1000 | 1.559 | 1.809 | <10 |
| 45 | 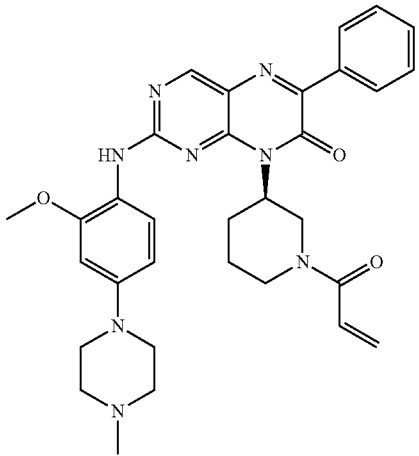 [SMILES: C=CC(=O)N1CCC[C@@H](n2c(=O)c(-c3ccccc3)nc3cnc(Nc4ccc(N5CCN(C)CC5)cc4OC)nc32)C1] | >1000 | >1000 | 1.775 | 4.276 | <10 |

TABLE 1-continued

Kinase levels and selectivity, cellular level and selectivity, and partial solubility of Compound

| Number of compound | Structure of compound | Inhibitory activity of EGFR on kinase (IC$_{50}$, nM) | | Inhibitory activity on proliferation of cells (IC$_{50}$, μM) | | Solubility (pH 6.8, g/mL) |
|---|---|---|---|---|---|---|
| | | WT | T790M/L858R | H1975 | A431 | |
| 46 | | >10000 | 13.3 | 2.160 | 2.392 | 43.2 |
| 47 | | 0.5 | 0.2 | 0.018 | 1.733 | <10 |

TABLE 1-continued

Kinase levels and selectivity, cellular level and selectivity, and partial solubility of Compound

| Number of compound | Structure of compound | Inhibitory activity of EGFR on kinase (IC$_{50}$, nM) | | Inhibitory activity on proliferation of cells (IC$_{50}$, μM) | | Solubility (pH 6.8, g/mL) |
|---|---|---|---|---|---|---|
| | | WT | T790M/L858R | H1975 | A431 | |
| 48 | | 361.6 | 20.8 | 0.031 | 0.640 | <10 |
| 49 | | 19.2 | 14.2 | 0.368 | 0.287 | <10 |

TABLE 1-continued
Kinase levels and selectivity, cellular level and selectivity, and partial solubility of Compound
| Number of compound | Structure of compound | Inhibitory activity of EGFR on kinase (IC$_{50}$, nM) | | Inhibitory activity on proliferation of cells (IC$_{50}$, μM) | | Solubility (pH 6.8, g/mL) |
|---|---|---|---|---|---|---|
| | | WT | T790M/L858R | H1975 | A431 | |
| 50 | 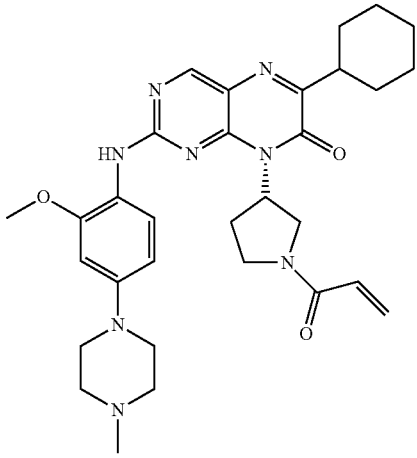 | 2.7 | 86.9 | 1.244 | 1.112 | 719 |
| 51 | 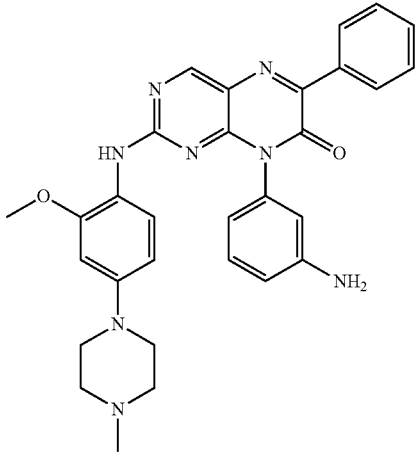 [SMILES: COc1cc(N2CCN(C)CC2)ccc1Nc1ncc2nc(-c3ccccc3)c(=O)n(-c3cccc(N)c3)c2n1] | 16.6 | 250.6 | 5.338 | 2.060 | <10 |
| 52 | 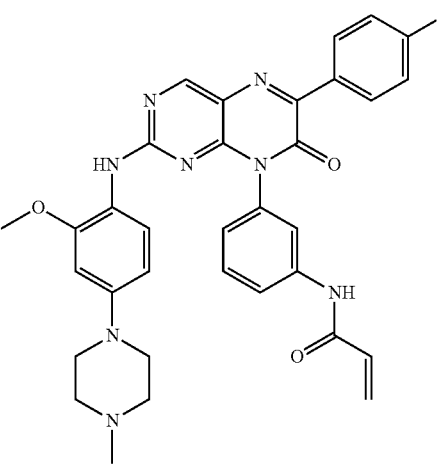 | 1.3 | 0.6 | 0.044 | 1.462 | <10 |

TABLE 1-continued

Kinase levels and selectivity, cellular level and selectivity, and partial solubility of Compound

| Number of compound | Structure of compound | Inhibitory activity of EGFR on kinase (IC$_{50}$, nM) | | Inhibitory activity on proliferation of cells (IC$_{50}$, μM) | | Solubility (pH 6.8, g/mL) |
|---|---|---|---|---|---|---|
| | | WT | T790M/L858R | H1975 | A431 | |
| 53 | | 9.6 | 74.2 | 0.479 | 0.593 | <10 |
| 54 | | 1.5 | 3.5 | 1.065 | 4.096 | <10 |
| 55 | | 6.6 | 6.1 | 0.262 | 1.299 | <10 |

TABLE 1-continued

Kinase levels and selectivity, cellular level and selectivity, and partial solubility of Compound

| Number of compound | Structure of compound | Inhibitory activity of EGFR on kinase (IC$_{50}$, nM) | | Inhibitory activity on proliferation of cells (IC$_{50}$, μM) | | Solubility (pH 6.8, g/mL) |
|---|---|---|---|---|---|---|
| | | WT | T790M/L858R | H1975 | A431 | |
| 56 | | 1.6 | 1.7 | 0.228 | 1.203 | <10 |
| 57 | | 2.8 | 1.8 | 0.225 | 1.369 | <10 |
| 58 | | | | | | <10 |

TABLE 1-continued

Kinase levels and selectivity, cellular level and selectivity, and partial solubility of Compound

| Number of compound | Structure of compound | Inhibitory activity of EGFR on kinase (IC$_{50}$, nM) | | Inhibitory activity on proliferation of cells (IC$_{50}$, μM) | | Solubility (pH 6.8, g/mL) |
|---|---|---|---|---|---|---|
| | | WT | T790M/L858R | H1975 | A431 | |
| AZD9291 | | 236 | 12.1 | 0.016 | 1.9 | 3.50 |

The solubility of AZD9291 was tested at pH 7.4 (*J. Med. Chem.*, 2014, 57: 8249-8267)

Inhibition Screening Test on Tyrosine Kinase Activity of Compound 53 (Before and After Resolution)

| Number of compound | Structure of compound | Inhibitory IC$_{50}$ means (nM) ± SD value on tyrosine kinase activity | | Inhibitory IC$_{50}$ means (μM) ± SD value on tumor cell growth activity | |
|---|---|---|---|---|---|
| | | EGFR | EGFR/T790 M/L858R | A431 | NCI-H1975 |
| 53 | | 9.6 | 74.2 | 0.593 | 0.479 |

-continued

| Number of compound | Structure of compound | Inhibitory IC$_{50}$ means (nM) ± SD value on tyrosine kinase activity | | Inhibitory IC$_{50}$ means (μM) ± SD value on tumor cell growth activity | |
|---|---|---|---|---|---|
| | | EGFR | EGFR/T790 M/L858R | A431 | NCI-H1975 |
| 53-1 (R) | | 272.5 ± 38.0 | 294.8 ± 85.0 | 5.314 ± 1.037 | >10 |
| 53-2 (S) | | 8.0 ± 0.8 | 15.2 ± 2.3 | >10 | 0.062 ± 0.012 |

Example 4

1. H1975 Cell Xenograft Tumor Assay: Pharmacodynamic Evaluation in Animals

Purpose of experiment: H1975 transplanted BALB/c nude mice were orally administered (PO) with a substance to be tested for 14 consecutive days. The body weight and tumor size of nude mice were observed and recorded. The changes of physiological activity of nude mice after administration were observed for evaluating antineoplastic efficacy.

1.1 Preparation of H1975 Cell

H1975 cells were obtained from Shanghai Institute of Materia Medica. Cells were cultured in 1640+10% FBS (Gibco) at 37° C. in a constant-temperature carbon dioxide incubator with 5% $CO_2$ concentration. Cells were fluid-changed and passaged for one time every 2-3 days and expanded. When the desired amount of cells was achieved, transplantation of cells was performed. Before transplantation, cell viability should be maintained above 90%, serum-free 1640 medium was used for suspending cells, and the cell concentration in suspension was 20 million/ml.

1.2 Modeling of H1975 Xenograft Tumor 40 male BALB/c nude mice, aged 4-5 weeks and weighing 17-23 g, were purchased from Shanghai Bikai, placed in an animal room environment for 2-3 days, and then seeded with cells. Cell suspension was subcutaneously injected at forelimb of the nude mouse rich in capillaries, and each mouse was injected with 0.1 mL of cell suspension.

Experimental conditions in animal room:
Laboratory temperature: 23±3° C.
Laboratory humidity: 30-60%
12 hours day-night rhythm In about 2-3 weeks, xenograft tumor can be found, and mice were grouped and administered with a drug when average size of tumor reaching 300 mm$^3$.

1.3 Formulation of Substance to be Tested

Appropriate amount of a substance to be tested was weighed, suspended in 14 mL of DMSO-PEG400 saline solution (DMSO:PEG400:saline=1:30:69) respectively, formulated according to the following table, suspended or dissolved by ultrasonic wave, filled into vials and sealed, and reserved in a 4° C. refrigerator for further use.

| Experiment group | Weighing (mg) | Actual concentration (mg/ml) | Dose (mg/kg) |
|---|---|---|---|
| 1 | 0 | 0 | 0 |
| 2 | 17.5 | 1.25 | 5 |
| 3 | 35 | 2.5 | 10 |
| 4 | 87.5 | 6.25 | 25 |
| 5 | 175 | 12.5 | 50 |
| 6 | 350 | 25 | 100 |

1.4 Dosage and Mode of Administration

The mice were administered with a dosage of 0.1 ml/25 g through oral gavage once a day, and the mice were observed for their status and abnormalities. The length and width of a tumor and body weight of a mouse were recorded at least twice a week. The tumor size is calculated as V=0.5*length*width*width.

FIG. 1 shows pharmacodynamic evaluation of a series of compounds: after orally administered to nude mice of H1975 cell xenograft model for 14 days, Compound 14 exhibited superior efficacy over CO-1686.

Figure 2:
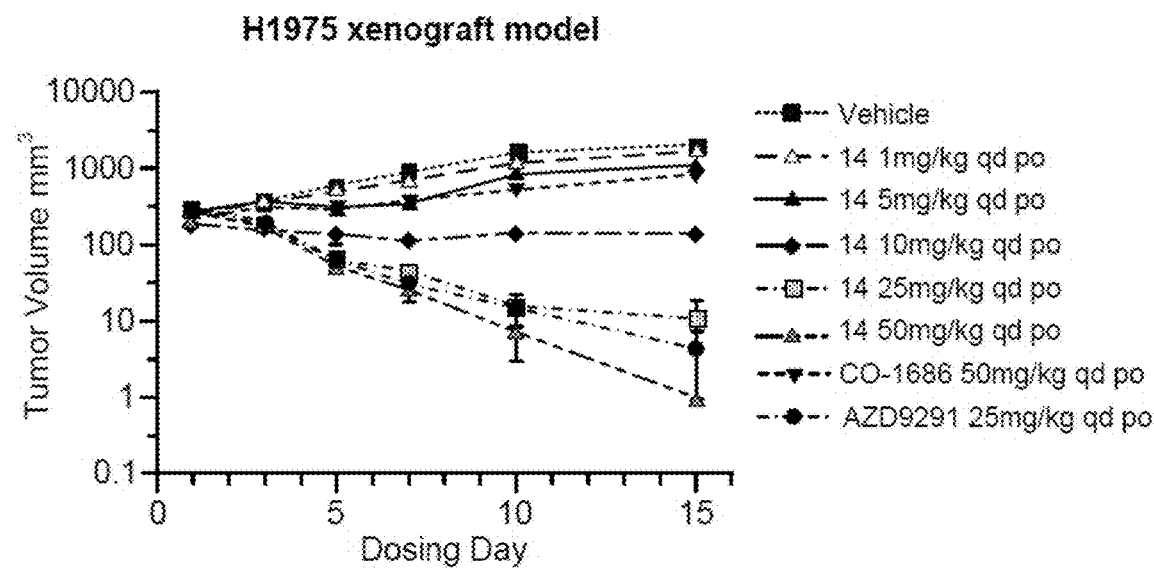
FIG. 2 shows pharmacodynamics comparison between Compound 14 and CO-1686 and AZD9291: Compound 14 (10 mg/kg) exhibited better efficacy over CO-1686 (50 mg/kg), Compound 14 (25 mg/kg) exhibited comparable efficacy to AZD9291 (25 mg/kg), both of which can effectively reduce the size of a tumor, and the mice still live and the tumor did not recur after administration was stopped for 1 month.

FIG. 2 shows pharmacodynamics comparison between Compound 14 and CO-1686 and AZD9291: Compound 14 (10 mg/kg) exhibited better efficacy over CO-1686 (50 mg/kg), Compound 14 (25 mg/kg) exhibited comparable efficacy to AZD9291 (25 mg/kg), both of which can effectively reduce the size of a tumor, and the mice still live and the tumor did not recur after administration was stopped for 1 month.

2. A431 Cell Xenograft Tumor Assay:

Purpose of experiment: A431 xenograft tumor BALB/c nude mice were orally administered (PO) with a substance to be tested for 14 consecutive days. The body weight and tumor size of nude mice were observed and recorded. The changes of physiological activity of nude mice after administration were observed for evaluating antineoplastic efficacy.

2.1 Preparation of A431 Cell

A431 cells belong to our laboratory, and in October 2015 confirmed by STR experiment. Cells were cultured in 1640+ 10% FBS (Gibco) at 37° C. in a constant-temperature carbon dioxide incubator with 5% $CO_2$ concentration. Cells were fluid-changed and passaged for one time every 2-3 days and expanded. When the desired amount of cells was achieved, transplantation of cells was performed. Before transplantation, cell viability should be maintained above 90%, serum-free 1640 medium was used for suspending cells, and the cell concentration in suspension was 20 million/ml.

2.2 Modeling of A431 Xenograft Tumor 40 male BALB/c nude mice, aged 4-5 weeks and weighing 17-23 g, were purchased from Shanghai Bikai, placed in an animal room environment for 2-3 days, and then seeded with cells. Cell suspension was subcutaneously injected at forelimb of the nude mouse rich in capillaries, and each mouse was injected with 0.1 mL of cell suspension.

Experimental conditions in animal room:
Laboratory temperature: 23±3° C.
Laboratory humidity: 30-60%
12 hours day-night rhythm In about 2-3 weeks, xenograft tumor can be found, and mice were grouped and administered with a drug when average size of tumor reaching 500 $mm^3$.

2.3 Formulation of Substance to be Tested

Appropriate amount of a substance to be tested was weighed, suspended in 14 mL of DMSO-PEG400 saline solution (DMSO:PEG400:saline=1:30:69) respectively, formulated according to the following table, suspended or dissolved by ultrasonic wave, filled into vials and sealed and reserved in a 4° C. refrigerator for further use.

| Experiment group | Weighing (mg) | Actual concentration (mg/ml) | Dose (mg/kg) |
|---|---|---|---|
| 1 | 0 | 0 | 0 |
| 2 | 17.5 | 1.25 | 5 |
| 3 | 35 | 2.5 | 10 |
| 4 | 87.5 | 6.25 | 25 |
| 5 | 175 | 12.5 | 50 |
| 6 | 350 | 25 | 100 |

2.4 Dosage and Mode of Administration

The mice were administered with a dosage of 0.1 ml/25 g through oral gavage once a day, and the mice were observed for their status and abnormalities. The length and width of a tumor and body weight of a mouse were recorded at least twice a week. The tumor size is calculated as V=0.5*length*width*width.

Figure 3:
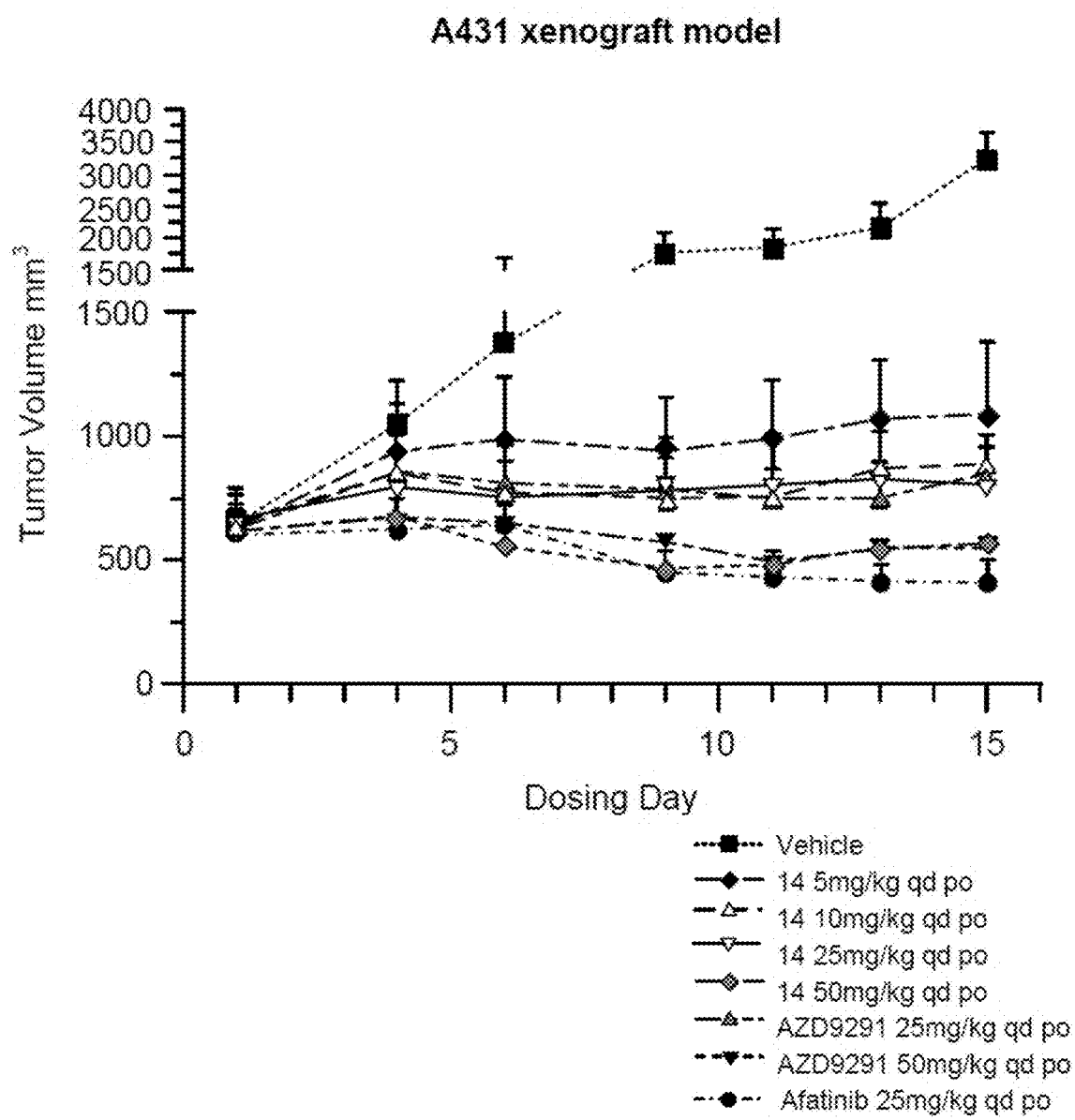
FIG. 3 shows that compound 14 exhibited better selectivity on wild-type EGFR. Nude mice of EGFR wild-type A431 cell xenograft model were administered for 14 days by oral administration, compound 14 (25 mg/kg) exhibited performance comparable to the same dose of AZD9291, that is, the size of the tumor did not substantially change, and the selectivity was significantly better than afatinib (a medicament of $2^{nd}$ generation).

FIG. 3 shows that compound 14 exhibited better selectivity on wild-type EGFR. Nude mice of EGFR wild-type A431 cell xenograft model were administered for 14 days by oral administration, compound 14 (25 mg/kg) exhibited performance comparable to the same dose of AZD9291, that is, the size of the tumor did not substantially change, and the selectivity was significantly better than afatinib (a medicament of $2^{nd}$ generation).

Example 4

1. Acute Toxicity Evaluation of Compound: 10 times and higher dose of AZD9291 were selected for Acute toxicity test in ICR mice. In contrast, ZW-W-33 at 100 mg/kg, 250 mg/kg, and 500 mg/kg showed comparable toxicity to the same dose of AZD9291 with a slight decrease in body weight.

Figure 4A:
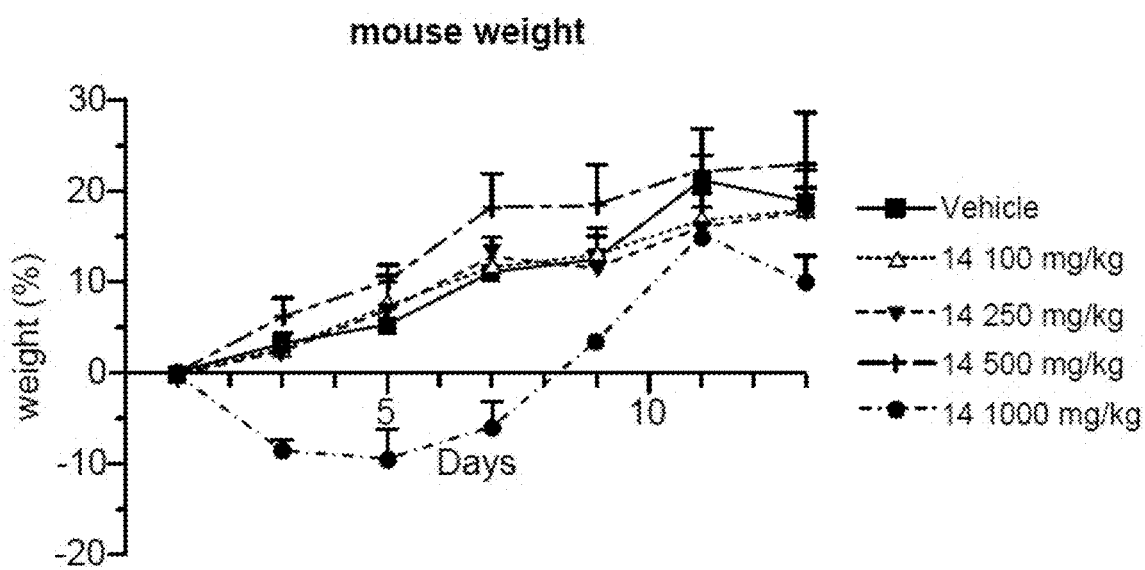
FIG. 4 shows the toxicity assessment of Compound 14 and AZD9291.
Figure 4B:
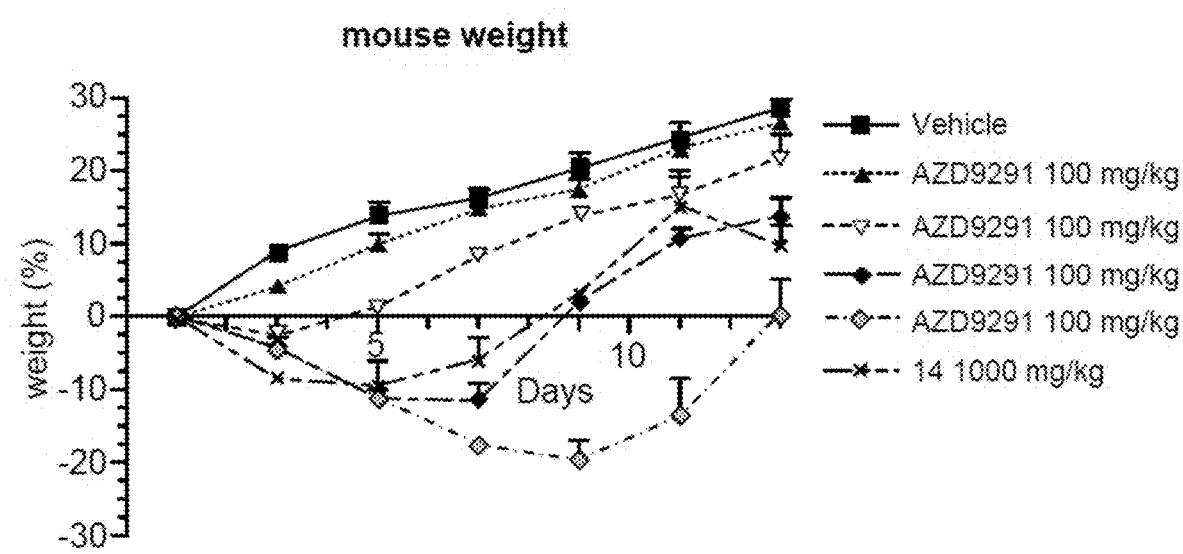
Figure 5A:
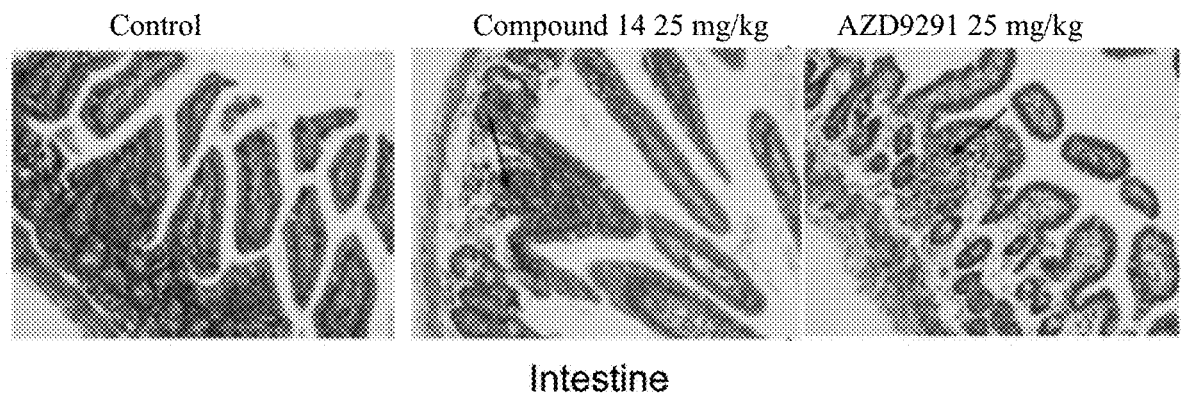
FIG. 5A: intestine tissue; left panel (Control) shows the normal tissue structure, no pathological change; middle panel (Compound 14) shows the mucosal inflammatory cell focal infiltration, as indicated by the black arrow; and right panel (AZD9291) shows the inflammatory cell focal infiltration seen in tissue, as indicated by the black arrow.
Figure 5B:
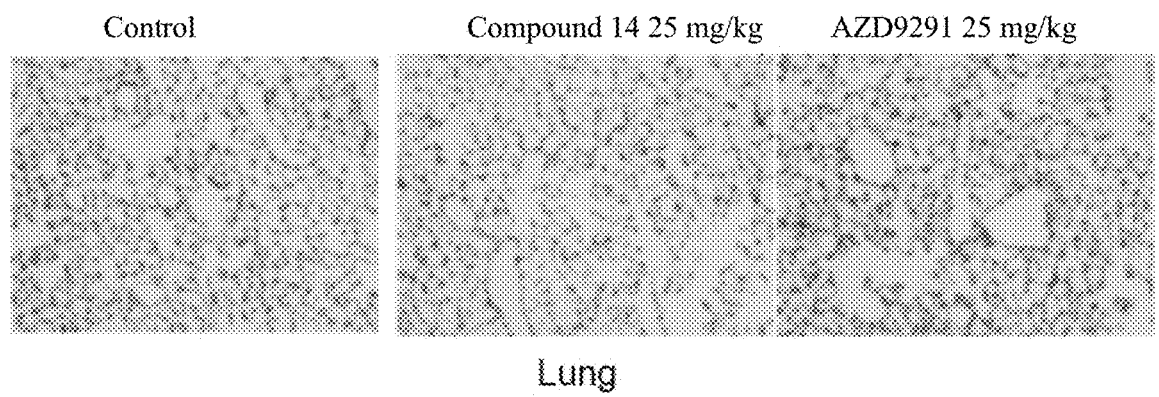
FIG. 5B: lung tissue; left panel (Control) shows the normal tissue structure; middle panel (Compound 14) shows the normal tissue structure, no pathological change; and right panel (AZD9291) shows the pulmonary congestion, interstitial edema.
Figure 5C:
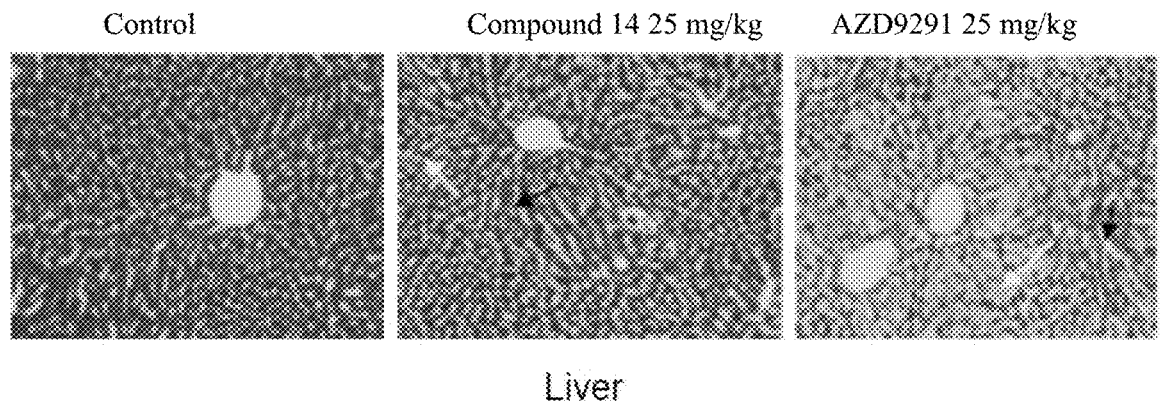
FIG. 5C: liver tissue; left panel (Control) shows the normal tissue structure, no pathological change; middle panel (Compound 14) shows 1) the extensive hepatic sinusoids dilatation in the entire tissue, as indicated by the black arrow, and 2) visible mild fatty degeneration in liver tissue, with small droplets of lipid, as indicated by the yellow arrow; and right panel (AZD9291) shows 1) more severe liver injury, extensive hepatic sinusoids dilatation, as indicated by the black arrow, and 2) visible necrosis in liver tissue, as indicated by the yellow arrow.
Figure 5D:
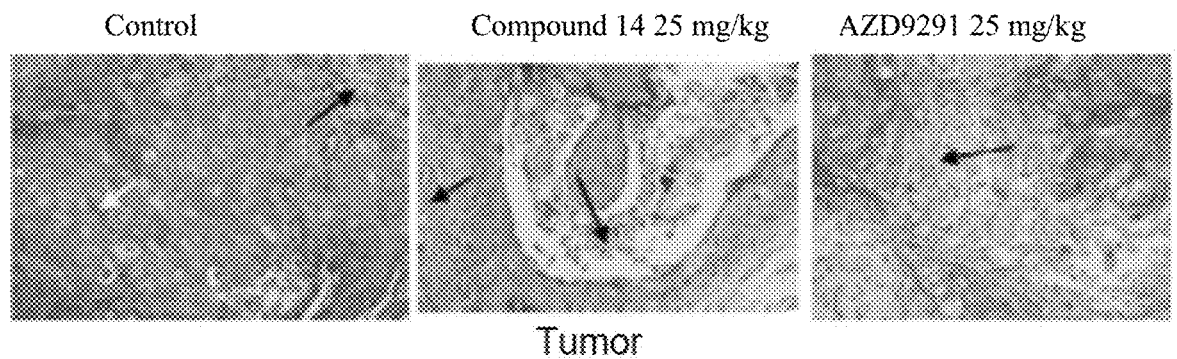
FIG. 5D: tumor tissue; left panel (Control) shows 1) some part of nucleus shrinking in the tissue, as indicated by the yellow arrow, and 2) a slight necrosis of cells in the entire of tissue, as indicated by the black arrows; middle panel (Compound 14) shows moderate necrosis of cells in the entire tissues, as indicated by the black arrow; and right pane (AZD9291) shows moderate necrosis of cells in the entire tissues, as indicated by the black arrow.
Figure 5E:
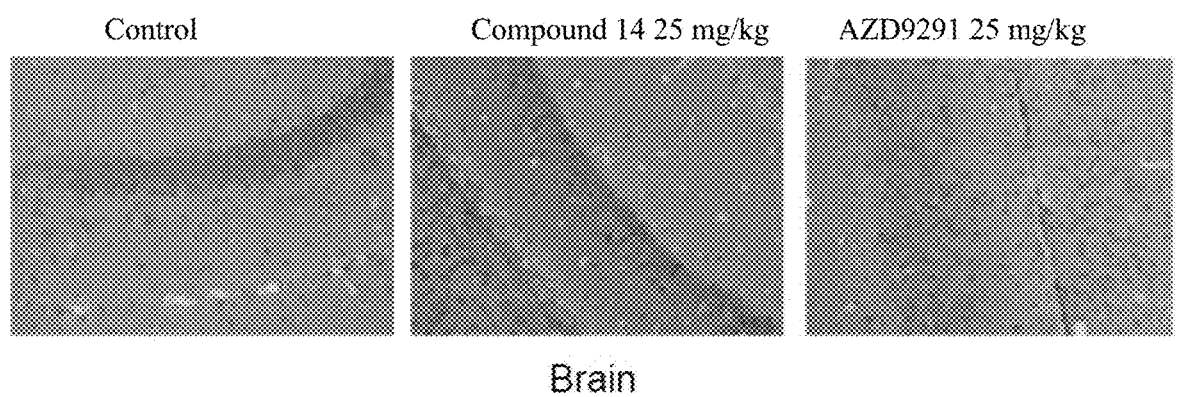
FIG. 5E: brain tissue; left panel (Control) shows the normal tissue structure, no pathological change; middle panel (Compound 14) shows the normal tissue structure, no pathological change; and right panel (AZD9291) shows the normal tissue structure, no pathological change.
Figure 5F:
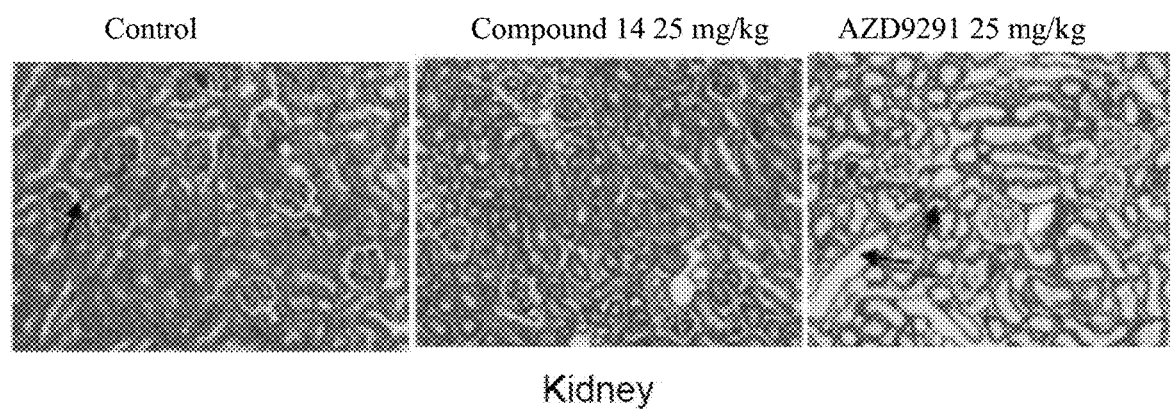
FIG. 5F: kidney tissue; left panel (Control) shows a part of glomerular wall in the tissue thickening, as shown by the black arrow; middle (Compound 14) shows 1) a part of glomerular wall in the tissue thickening, as shown by the black arrow, and 2) no significant abnormality; and right pane (AZD9291) shows 1) extensive kidney tubular lumen expansion in tissue, as shown by the black arrow, 2) part of glomerular wall thickening, as shown by the yellow arrow, and 3) visible transparent tube.
Figure 5G:
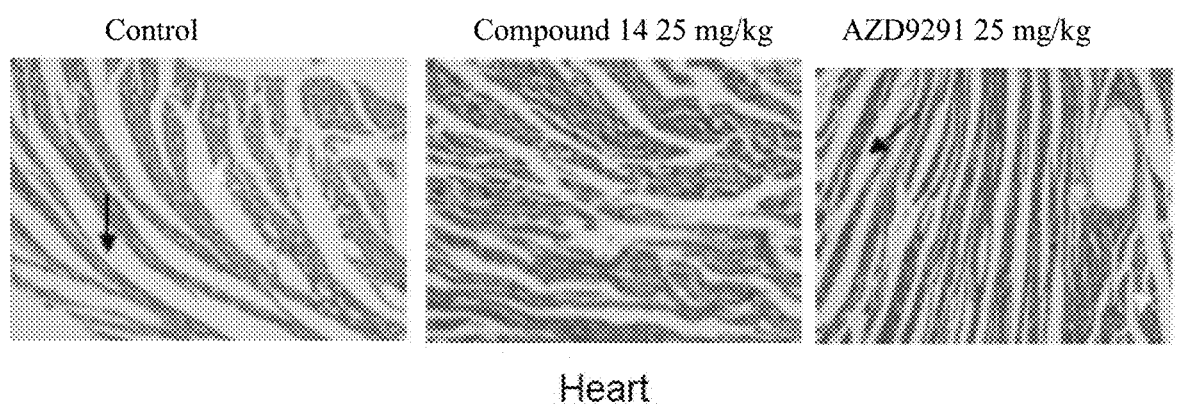
FIG. 5G: heart tissue; left panel (Control) shows 1) moderate expansion of myocardial fiber gap in the tissue, as indicated by the black arrow, 2) vacuoles formed in the cytoplasm of the myocardial fibers, as indicated by the yellow arrows; middle panel (compound 14) shows moderate expansion of myocardial fiber gap in the tissue; and right panel (ADZ9291) shows 1) moderate expansion of myocardial fiber gap in the tissue, as indicated by the black arrow, 2) vacuoles formed in the cytoplasm of the myocardial fibers, as indicated by the yellow arrows.

FIG. 4 shows the toxicity assessment of Compound 14 and AZD9291.

2. FIG. 5 shows the pathological analysis of tumor-bearing mice after 14 consecutive days of administration.

Conclusion: after long-term (14 days) administration of continuous treatment dose, no obvious pathological change was observed in all organs, and side effects were comparable to those of the same dose of positive drug AZD9291.

All references mentioned in the present application are incorporated herein by reference, as if each reference was individually incorporated by reference. In addition, it should be understood that after reading the above teachings of the present invention, those skilled in the art can make various modifications or changes to the present invention, and such equivalent forms also fall within the scope of the appended claims of the present application.

The invention claimed is:
1. A compound of formula I or a pharmaceutical acceptable salt thereof:

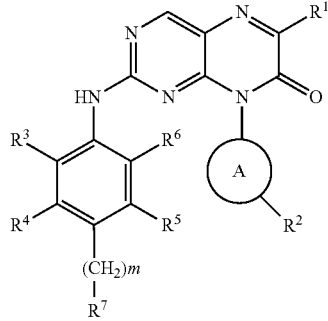

wherein,
R$^1$ is independently selected from the group consisting of substituted or unsubstituted phenyl, and optionally substituted C$_3$-C$_8$ cycloalkyl;
A is a divalent radical -A'-;
A' is a benzene ring, or a five- or six-membered nitrogen-containing heterocycle;
R$^2$ is independently selected from the group consisting of C$_2$-C$_4$ alkenyl substituted acylamino and substituted or unsubstituted C$_2$-C$_4$ alkenyl substituted acyl;
m is 0;
R$^7$ is independently selected from the group consisting of:

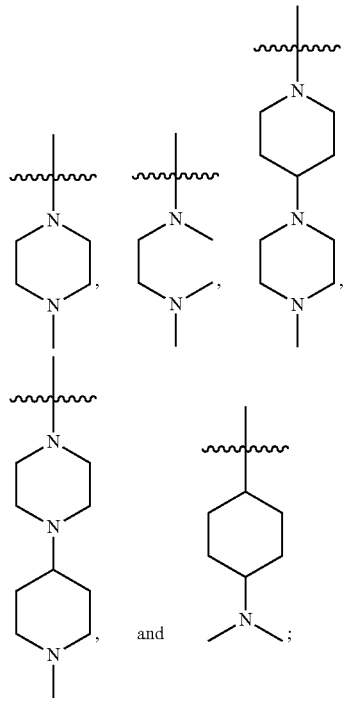

and
R$^3$, R$^4$, R$^5$ and R$^6$ are independently selected from the group consisting of H, substituted or unsubstituted C$_1$-C$_6$ alkoxy, and substituted or unsubstituted C$_1$-C$_6$ alkyl;
provided that when R$^1$ is H and m is 0, R$^3$, R$^4$, R$^5$ and R$^6$ are not each H; and when R$^1$ is H, m is 0, A' is a benzene ring and R$^7$ is

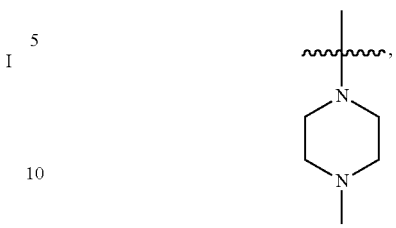

if one of R$^3$ and R$^6$ is a methoxy, the other is not H.

2. A compound or a pharmaceutical acceptable salt thereof selected from the group consisting of:

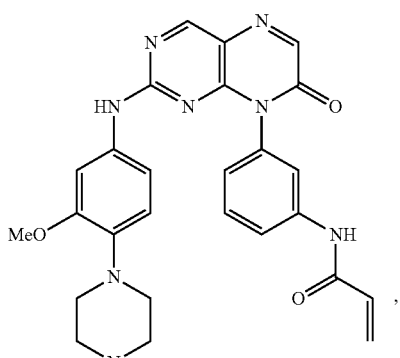

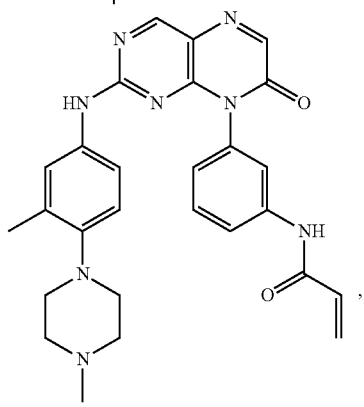

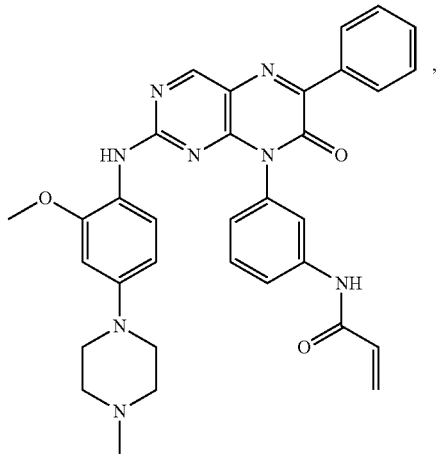

139
-continued
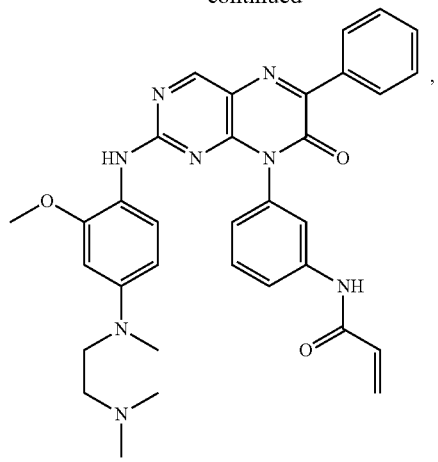
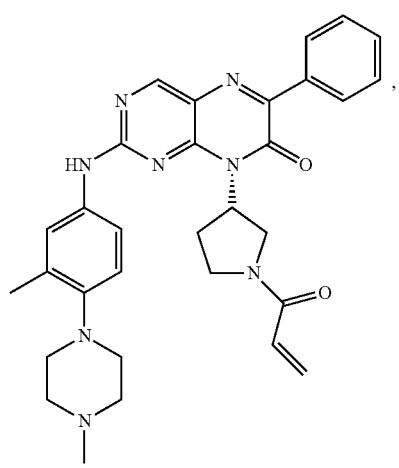
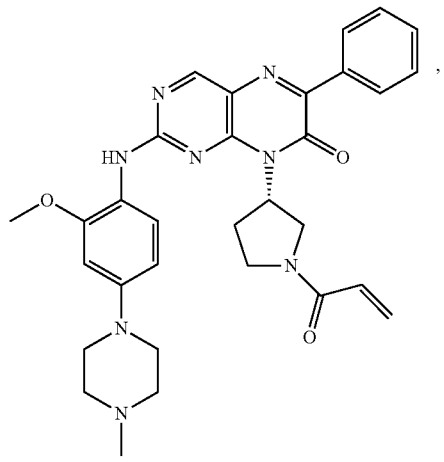
140
-continued
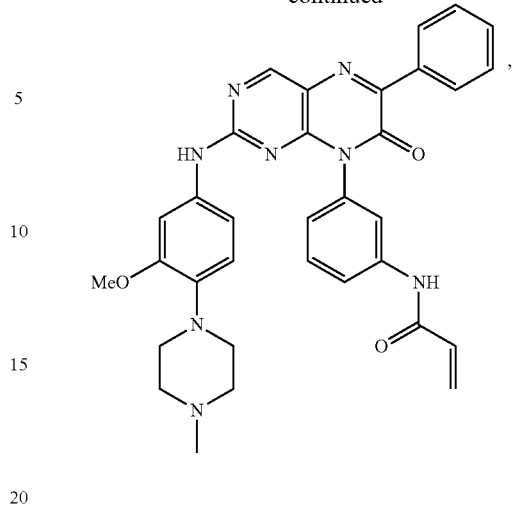
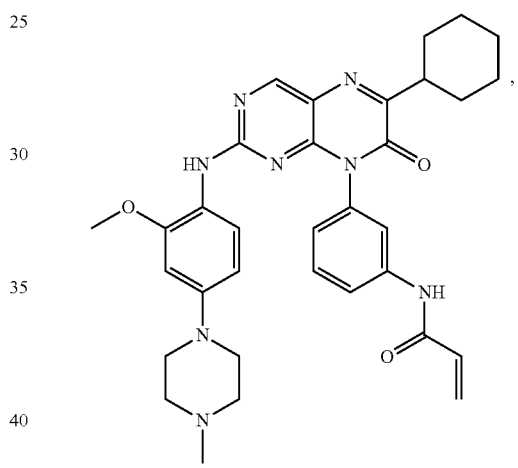
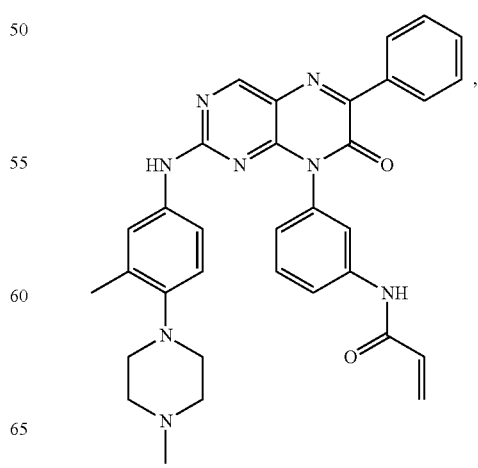

141
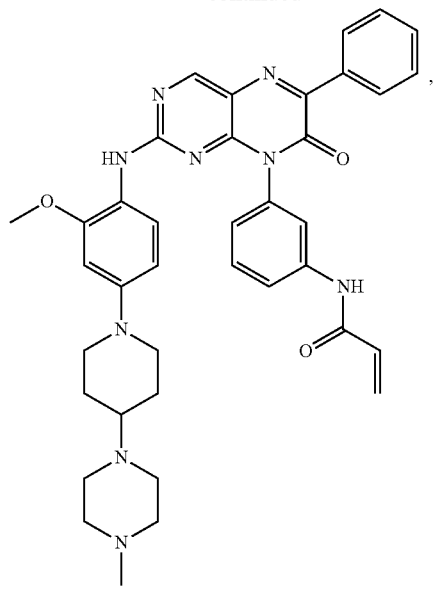
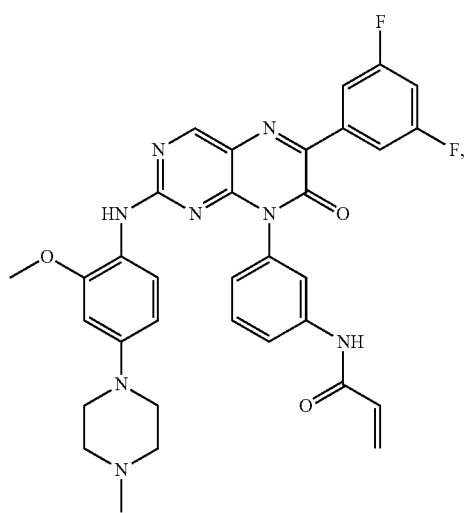
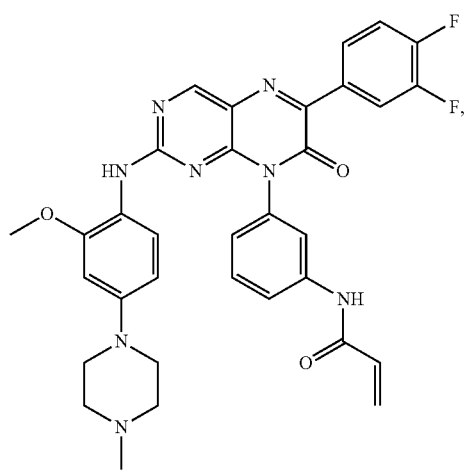
142
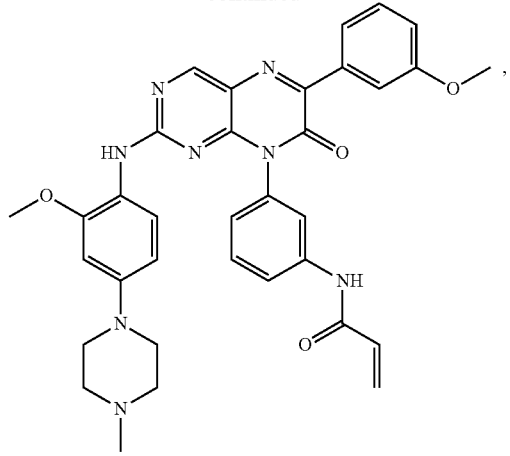
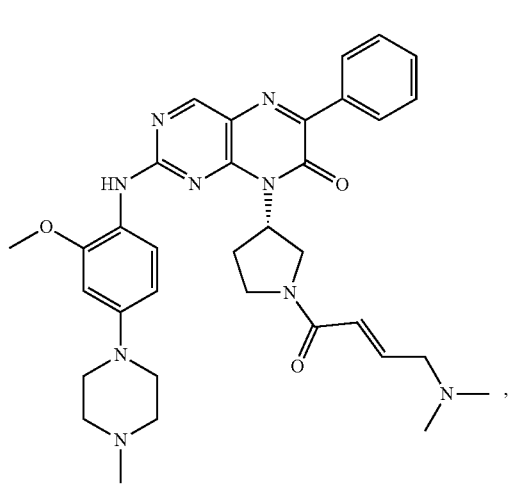
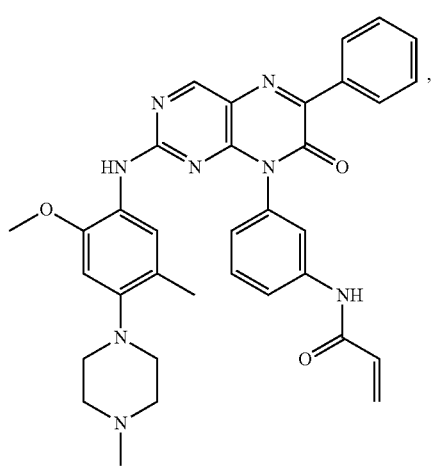

143
-continued
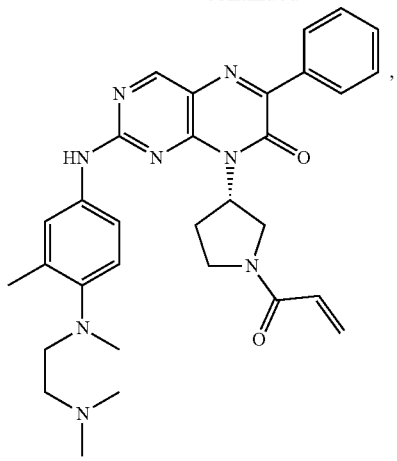
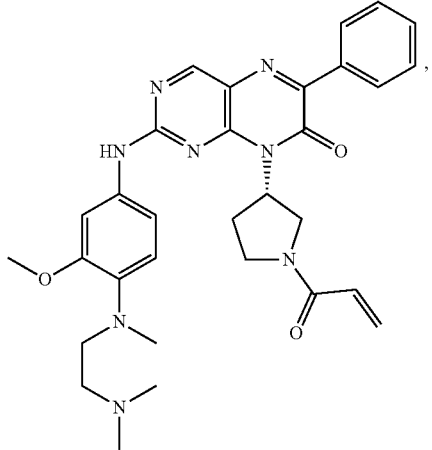
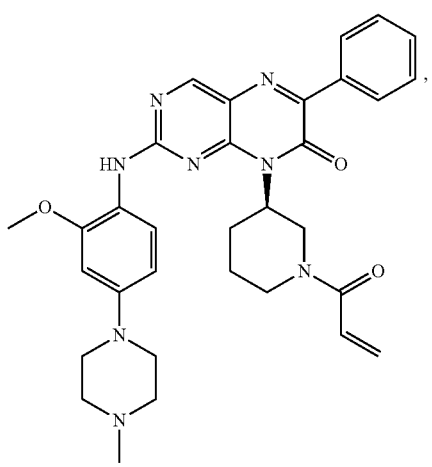
144
-continued
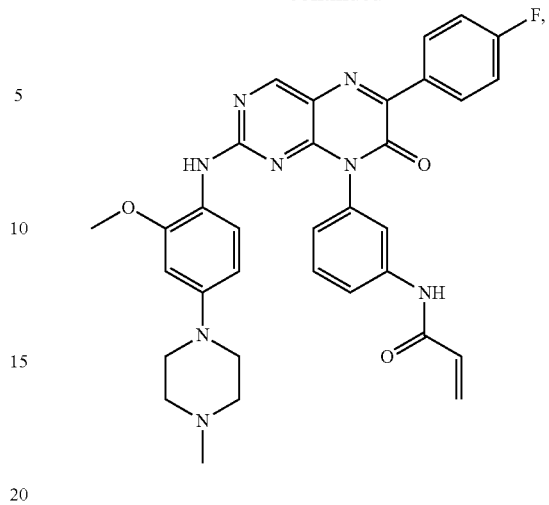
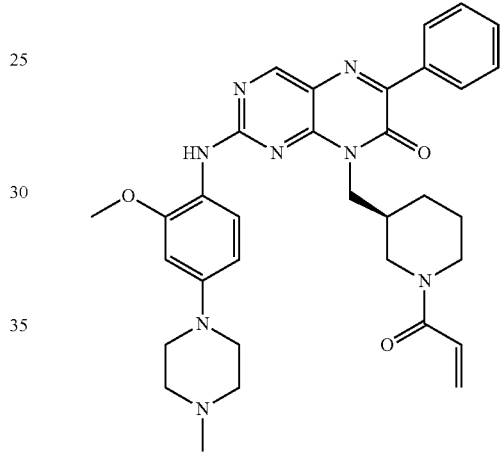
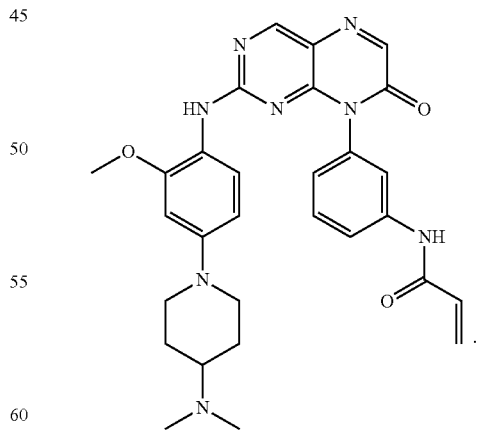
, and
3. The compound of claim 1, wherein
R¹ is substituted or unsubstituted phenyl;
R² is independently $C_2$-$C_4$ alkenyl substituted acylamino, or $C_2$-$C_4$ alkenyl substituted acyl;

$R^7$ is:
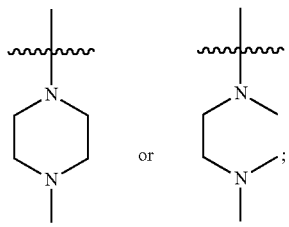
or
and
$R^3$, $R^4$, $R^5$ and $R^6$ are independently selected from the group consisting of H, substituted or unsubstituted $C_1$-$C_3$ alkoxy, and substituted or unsubstituted $C_1$-$C_3$ alkyl.
4. A compound or a pharmaceutical acceptable salt thereof selected from the group consisting of:
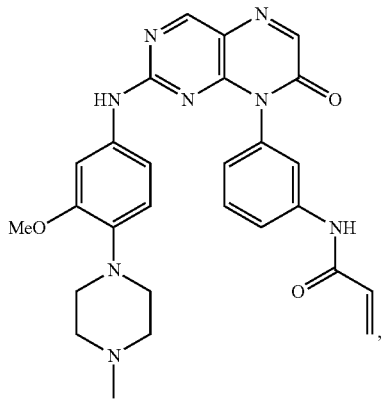
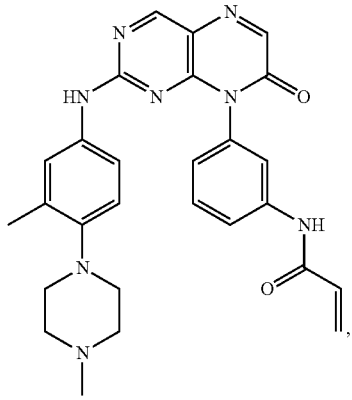
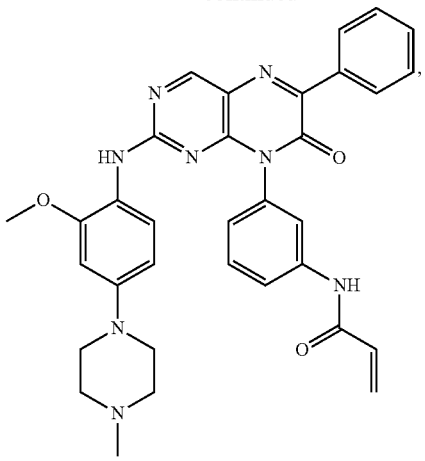
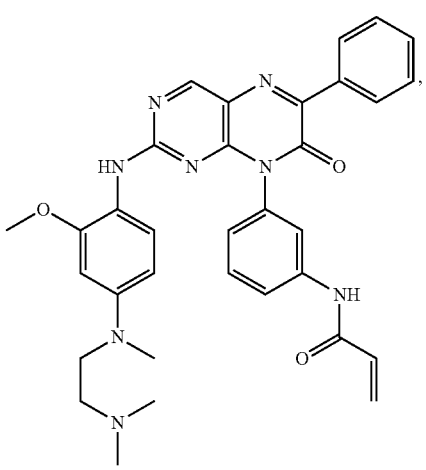
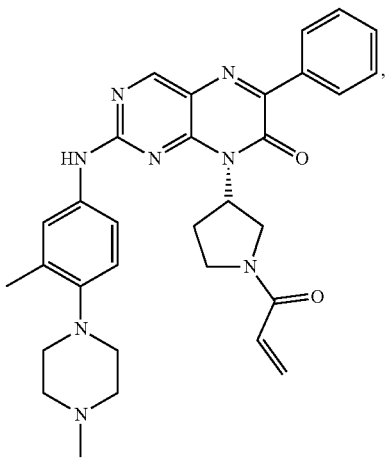

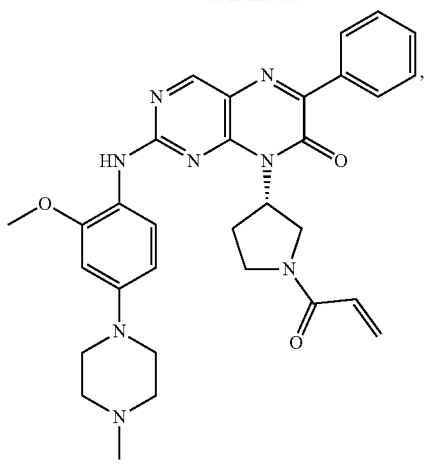

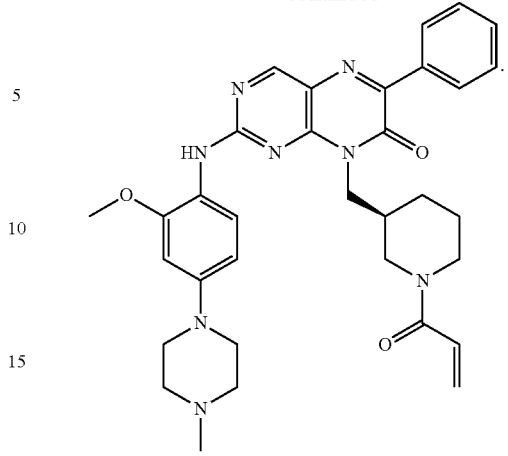

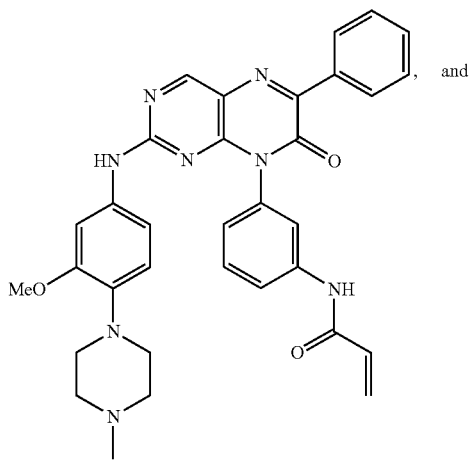
, and

5. The compound of claim 1, wherein $R^3$, $R^4$, $R^5$ and $R^6$ are independently selected from the group consisting of substituted or unsubstituted $C_1$-$C_3$ alkoxy and substituted or unsubstituted $C_1$-$C_3$ alkyl.

6. The compound of claim 1, wherein the substituted phenyl is halogen or $C_{1-4}$ alkoxy substituted phenyl.

7. A pharmaceutical composition, comprising the compound or a pharmaceutical acceptable salt thereof of claim 2 and a pharmaceutically acceptable carrier or excipient.

8. A method for inhibiting EGFR comprising administering to a patient in need thereof an effective amount of the compound of claim 2.

9. A method for treating EGFR-mediated diseases comprising administering to a patient in need thereof an effective amount of the compound of claim 2.

10. The method of claim 9, wherein the EGFR-mediated disease is cancer.

11. The method of claim 10, wherein the cancer is selected from the group consisting of non-small cell lung cancer, small cell lung cancer, lung adenocarcinoma, lung squamous cell carcinoma, breast cancer, prostate cancer, glioblastoma, ovarian cancer, squamous cell carcinoma of head and neck, cervical cancer, esophageal cancer, liver cancer, kidney cancer, pancreas cancer, colon cancer, skin cancer, leukemia, lymphoma, stomach cancer, multiple myeloma, and solid tumors.

* * * * *